US011767507B2

(12) United States Patent
Chung

(10) Patent No.: US 11,767,507 B2
(45) Date of Patent: Sep. 26, 2023

(54) METHODS FOR EFFICIENT GENERATION OF GABAERGIC INTERNEURONS FROM PLURIPOTENT STEM CELLS

(71) Applicant: THE MCLEAN HOSPITAL CORPORATION, Belmont, MA (US)

(72) Inventor: Sangmi Chung, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 15/034,699

(22) PCT Filed: Nov. 5, 2014

(86) PCT No.: PCT/US2014/064085

§ 371 (c)(1),
(2) Date: May 5, 2016

(87) PCT Pub. No.: WO2015/069736

PCT Pub. Date: May 14, 2015

(65) Prior Publication Data

US 2016/0272940 A1 Sep. 22, 2016

Related U.S. Application Data

(60) Provisional application No. 62/053,535, filed on Sep. 22, 2014, provisional application No. 61/901,541, filed on Nov. 8, 2013.

(51) Int. Cl.
*C12N 5/0793* (2010.01)
*A61K 35/30* (2015.01)

(52) U.S. Cl.
CPC ............ *C12N 5/0619* (2013.01); *A61K 35/30* (2013.01); *C12N 2501/115* (2013.01); *C12N 2501/119* (2013.01); *C12N 2501/13* (2013.01); *C12N 2501/155* (2013.01); *C12N 2501/41* (2013.01); *C12N 2501/415* (2013.01); *C12N 2506/02* (2013.01); *C12N 2506/08* (2013.01); *C12N 2506/45* (2013.01)

(58) Field of Classification Search
CPC ............ C12N 5/0619; C12N 2501/115; C12N 2501/119; C12N 2501/13; C12N 2501/155; C12N 2501/41; C12N 2501/415; C12N 2506/02; C12N 2506/08; C12N 2506/45
See application file for complete search history.

(56) References Cited

U.S. PATENT DOCUMENTS 4,353,888 A 10/1982 Sefton
4,744,933 A 5/1988 Rha et al.
4,749,620 A 6/1988 Rha et al.
4,814,274 A 3/1989 Shioya et al.
5,084,350 A 1/1992 Chang et al.
5,089,272 A 2/1992 Shioya et al.
5,843,780 A 12/1998 Thomson
5,945,577 A 8/1999 Stice et al.
5,994,619 A 11/1999 Stice et al.
6,200,806 B1 3/2001 Thomson
6,235,970 B1 5/2001 Stice et al.
7,029,913 B2 4/2006 Thomson
7,615,374 B2 11/2009 Vodyanyk et al.
8,684,921 B2 4/2014 Osorio
9,382,515 B2 7/2016 Jaenisch et al.
10,093,904 B2 10/2018 Jaenisch et al.
10,100,279 B2 * 10/2018 Nicholas .............. C12N 5/0618
2008/0233610 A1 9/2008 Thomson et al.
2009/0047263 A1 2/2009 Yamanaka et al.
2009/0068742 A1 3/2009 Yamanaka
2009/0081784 A1 3/2009 Vodyanyk et al.
(Continued)

FOREIGN PATENT DOCUMENTS

CA 2683056 10/2008
CA 2688539 12/2008
(Continued)

OTHER PUBLICATIONS

Liu et al., Cell. Mol. Life Sci., 68:3995-4008, published online Jul. 24, 2011.*
Mak et al., Stem Cells International, ID: 1400427, 2012 but published online Oct. 2011.*
Liu et al, Nature Protocols, 8(9):1670-1679, published online Aug. 8, 2013.*
Ni et al., Dev Brain Res., 152:159-169, 2004.*
(Continued)

*Primary Examiner* — Kimberly Ballard
*Assistant Examiner* — Stacey N MacFarlane
(74) *Attorney, Agent, or Firm* — Fish & Richardson P.C.

(57) ABSTRACT

Enhanced methods for the generation of medial ganglionic eminence (MGE) cells from pluripotent stem cells are provided that involve an additional step of contacting the cells with an activator of FGF8 signaling while differentiating Pax6+ cells progenitor cells into MGE cells with an activator of sonic hedgehog, and optionally a Wnt inhibitor. The activator of FGF8 signaling shifts the differentiation of the population of cells to NKX2.1+ MGE cells, rather than to CopuTFII+ caudal ganglionic eminence (CGE) cells. Methods for treatment of neurological disorders, such as epilepsy, by transplant of MGE cells, or GABAergic interneurons derived from human pluripotent stem cells, into a subject in need of treatment are also provided. Human pluripotent stem cell derived MGE cells when transplanted successfully suppress spontaneous seizures, e.g. in epilepsy. We also have developed a method to purify MGE cells and maturing interneurons from differentiated pluripotent stem cells using cell surface marker and molecular beacon technology.

19 Claims, 30 Drawing Sheets

Specification includes a Sequence Listing.

(56) References Cited

U.S. PATENT DOCUMENTS

| | | | |
|---|---|---|---|
| 2009/0191159 | A1 | 7/2009 | Sakurada et al. |
| 2009/0227032 | A1 | 9/2009 | Yamanaka et al. |
| 2009/0246875 | A1 | 10/2009 | Yamanaka et al. |
| 2009/0299763 | A1 | 12/2009 | Sakurada |
| 2009/0304646 | A1 | 12/2009 | Sakurada et al. |
| 2009/0324559 | A1 | 12/2009 | Sakurada et al. |
| 2010/0015705 | A1 | 1/2010 | Vodyanyk et al. |
| 2010/0062533 | A1 | 3/2010 | Yamanaka |
| 2010/0105100 | A1 | 4/2010 | Sakurada et al. |
| 2010/0184051 | A1 | 7/2010 | Hochedlinger et al. |
| 2011/0044961 | A1 | 2/2011 | Giorgetti et al. |
| 2012/0148549 | A1 | 6/2012 | Anderson et al. |
| 2015/0307839 | A1 | 10/2015 | Küppers-Munther et al. |
| 2015/0361393 | A1 * | 12/2015 | Nicholas .............. C12N 5/0619 435/366 |
| 2016/0115448 | A1 | 4/2016 | Studer et al. |
| 2021/0340502 | A1 | 11/2021 | Chung |

FOREIGN PATENT DOCUMENTS

| | | |
|---|---|---|
| EP | 1970446 | 9/2008 |
| WO | WO 99/20741 | 4/1999 |
| WO | WO 2001/051616 | 4/2002 |
| WO | WO 2007/069666 | 6/2007 |
| WO | WO 2008/118820 | 10/2008 |
| WO | WO 2008/124133 | 10/2008 |
| WO | WO 2008/151058 | 12/2008 |
| WO | WO 2009/006997 | 1/2009 |
| WO | WO 2010/108665 | 9/2010 |
| WO | WO 2012/106367 | 8/2012 |
| WO | 2013/067362 A1 | 5/2013 |
| WO | WO 2017/083705 | 5/2017 |

OTHER PUBLICATIONS

Ten Burge et al., Nature Cell Biology, (13):1070-76, Sep. 2011.*

Maroof et al., Cell Stem Cell, 12:559-572, May 2013.*

Close et al., Neuron 93:1035-1048, (Year: 2017).*

Storm et al., Development 133:1831-1844, (Year: 2006).*

Batista-Brito, et al., Neuron 63(4):466-481, Aug. 27, 2009 (Year: 2009).*

Storm et al., "Dose-dependent functions of Fgf8 in regulating telencephalic patterning centers, Development", 133:1831-1844, 2006 (Year: 2006).*

Kanatani et al., "COUP-TFII is preferentially expressed in the caudal ganglionic eminence and is involved in the caudal migratory stream", The Journal of Neuroscience, 28(50):13582-13591 (2008).

Liu et al., "Medial ganglionic eminence-like cells derived from human embryonic stem cells correct learning and memory deficits", Nat Biotechnol, 32:440-447 (2013).

Maroof et al., "Directed differentiation and funcitonal maturation fo cortical inerneurons from human embryonic stem cells", Cell Stem Cell, 12:559-572 (2013).

Nicholas et al., "Functional maturation of hPSC0 Derived forebrain interneurons requires an extended timelines and mimics human neural development", Cell Stem Cell, 12:573-586 (2013).

Aguilar-Valles et al., "Alterations in cognitive function and behavioral response to amphetamine induced by prenatal inflammation are dependent on the stage of pregnancy," Psychoneuroendocrinology, 2011, 36(5):634-648.

Alvarez-Dolado et al., "Cortical inhibition modified by embryonic neural precursors grafted into the postnatal brain," J Neurosci., 2006, 26:7380-7389.

Aoto et al., "Mouse GLB regulates Fgf8 expression and apoptosis in the developing neural tube, face, and limb bud," Dev Biol., 2002, 251:320-332.

Arber et al., "Cortical interneurons from human pluripotent stem cells: prospects for neurological and psychiatric disease," Frontiers in Cellular Neuroscience, 2013, 7:10, 11 pages.

Bao et al., Fluorescent probes for live-cell RNA detection, Annu Rev. Biomed. Engin., 2009, 11:25-47.

Baraban et al, "Reduction of seizures by transplantation of cortical GABAergic interneuron precursors into K v 1.1 mutant mice," Proc Natl Acad Sci USA., 2009, 106(36):15472-15477.

Bellin et al, "Induced pluripotent stem cells: the new patient?" Nat Rev Mol Cell Biol., 2012, 13:713-726.

Bjarkam et al, "Safety and function of a new clinical intracerebral microinjection instrument for stem cells and therapeutics examined in the Gottingen minipig," Stereotactic and Functional Neurosurgery, 2009, 88:56-63.

Borello et al, "FGF15 promotes neurogenesis and opposes FGF8 function during neocortical development," Neural Development, 2008, 3:17, 19 pages.

Braz et al, "Forebrain GABAergic neuron precursors integrate into adult spinal cord and reduce injury-induced neuropathic pain," Neuron, 2012, 74(4):663-675.

Brennand et al, "Modelling schizophrenia using human induced pluripotent stem cells," Nature, 2011, 473:221-225.

Brooks-Kayal et al, "Issues related to symptomatic and disease-modifying treatments affecting cognitive and neuropsychiatric comorbidities of epilepsy," Epilepsia, 2013, 54(Suppl. 4):44-60.

Cambray et al, "Activin induces cortical interneuron identity and differentiation in embryonic stem cell-derived telencephalic neural precursors," Nature Communications, 2012, 3:841, 11 pages.

Castiglioni et al, "Induced pluripotent stem cell lines from Huntington's disease mice undergo neuronal differentiation while showing alterations in the lysosomal pathway," Neurobiol Dis, 2012, 46:30-40.

Chambers et al, "Highly efficient neural conversion of human ES and iPS cells by dual inhibition of SMAD signaling," Nat Biotechnol, 2009, 27:275-280.

Chen et al, "Human pluripotent stem cell culture: considerations for maintenance, expansion, and therapeutics," Cell Stem Cell, 2014, 14:13-26.

Chiang et al, "Cyclopia and defective axial patterning in mice lacking Sonic hedgehog gene function," Nature, 1996, 383:407-413.

Chung et al, "ES cell-derived renewable and functional midbrain dopaminergic progenitors," PNAS, 2011, 108(23):9703-9708.

Chung et al, "Wnt1-1mx1a forms a novel autoregulatory loop and controls midbrain dopaminergic differentiation synergistically with the SHH-FoxA2 pathway," Cell Stem Cell., 2009, 5(6):646-658.

Cossart et al, "Dendritic but not somatic GABAergic inhibition is decreased in experimental epilepsy," Nature Neuroscience, 2001, 4:52-62.

Cramer et al, "Adverse effects of antiepileptic drugs: a brief overview of important issues," Expert Rev Neurother, 2010, 10(6):885-891.

Crossley et al, "The mouse Fgf8 gene encodes a family of polypeptides and is expressed in regions that direct outgrowth and patterning in the developing embryo," Development, 1995, 121(2):439-451.

Curia et al, "The pilocarpine model of temporal lobe epilepsy," J Neurosci Methods, 2008, 172(2):143-157.

Danjo et al, "Subregional specification of embryonic stem cell-derived ventral telencephalic tissues by timed and combinatory treatment with extrinsic signals," J Neurosci, 2011, 31(5):1919-1933.

De Lanerolle et al, "Hippocampal interneuron loss and plasticity in human temporal lobe epilepsy," BrainRes,, 1989, 495:387-395.

Doischer et al, "Postnatal differentiation of basket cells from slow to fast signaling devices," J Neurosci, 2008, 28(48):12956-12968.

Egawa et al, "Drug screening for ALS using patient-specific induced pluripotent stem cells," Sci Transl Med, 2012, 4(145):145ra104, 9 pages.

Engel et al, "A Proposed Diagnostic Scheme for People with Epileptic Seizures and with Epilepsy: Report of the ILAE Task Force on Classification and Terminology," Epilepsia, 2001, 42(6):796-803.

Engel et al, "Epilepsy in the world today: medical point of view," Epilepsia, 2002, 43(s6):12-13.

(56) References Cited

OTHER PUBLICATIONS

Faux et al, "Differential gene expression in migrating cortical interneurons during mouse forebrain development," J Comp Neurol, 2010, 518:1232-1248.
Fine et al, "Modulation of experimentally induced epilepsy by intracerebral grafts of fetal GABAergic neurons," Neuropsychologia, 1990, 28(6):627-634.
Flames et al, "Delineation of multiple subpallial progenitor domains by the combinatorial expression of transcriptional codes," J Neurosci, 2007, 27(36):9682-9695.
Fuccillo et al, "Temporal requirement for hedgehog signaling in ventral telencephalic patterning," Development, 2004, 131(20):5031-5040.
Fukuchi-Shimogori et al, "Neocortex Patterning by the Secreted Signaling Molecule FGF8," Science. 2001, 294:1071-1074.
Garel et al, "Molecular regionalization of the neocortex is disrupted in Fgf8 hypomorphic mutants," Development, 2003, 130(9):1903-1914.
Gemel et al, "Structure and sequence of human FGF8," Genomics, 1996, 35:253-257.
Gilman et al, "Diverse types of genetic variation converge on functional gene networks involved in schizophrenia," Nat Neurosci, 2012, 15:1723-1728.
Gimeno et al, "Expression of chick Fgf19 and mouse Fgf15 orthologs is regulated in the developing brain by Fgf8 and Shh," Developmental Dynamics, 2007, 236:2285-2297.
Groticke et al, "Behavioral alterations in the pilocarpine model of temporal lobe epilepsy in mice," Exp Neurol, 2007, 207:329-349.
Gulacsi et al, "Shh maintains Nkx2.1 in the MGE by a Gli3-independent mechanism," Cereb Cortex, 2006, 16:i89-i95.
Gunhaga et al, "Sonic hedgehog signaling at gastrula stages specifies ventral telencephalic cells in the chick embryo," Development, 2000, 127:3283-3293.
Gunhaga et al, "Specification of dorsal telencephalic character by sequential Wnt and FGF signaling," Nat Neurosci, 2003, 6:701-707.
Hattiangady et al, "Grafting of striatal precursor cells into hippocampus shortly after status epilepticus restrains chronic temporal lobe epilepsy," Exp Neurol, 2008, 212(2):468-481.
Hebert et al., "Targeting of cre to the Foxg1 (BF-1) Locus Mediates 1oxP Recombination in the Telencephalon and Other Developing Head Structures," Developmental Biology, 2000, 222:296-306.
Hebert et al., "The genetics of early telencephalon patterning: some assembly required," Nat Rev Neurosci., 2008, 9:678-685.
Helmstaedter, "Temporal lobe resection—does the prospect of seizure freedom outweigh the cognitive risks?" Nat Clin Pract Neuro, 2008, 4(2):66-67.
Hirsch et al., "Deficit of quantal release of GABA in experimental models of temporal lobe epilepsy," Nature Neuroscience, 1999, 2(6):499-500.
Houart et al., "Establishment of the telencephalon during gastrulation by local antagonism of Wnt signaling," Neuron, 2002, 35:255-265.
Hu et al., "Differentiation of human oligodendrocytes from pluripotent stem cells," Nature Protocols, 2009, 4(11):1614-1622.
Hunt et al., "GABA progenitors grafted into the adult epileptic brain control seizures and abnormal behavior," Nature Neuroscience, 2013, 16:692-697.
Ishibashi et al., "A sonic hedgehog-dependent signaling relay regulates growth of diencephalic and mesencephalic primordia in the early mouse embryo," Development, 2002, 129:4807-4819.
Itasaki et al., "Wise, a context-dependent activator and inhibitor of Wnt signalling," Development, 2003,130(18):4295-4305.
Jensen, "Epilepsy in 2013: Progress across the spectrum of epilepsy research," Nat Rev Neurol., 2014, 10:63-64.
Johnson et al., "Functional Neural Development from Human Embryonic Stem Cells: Accelerated Synaptic Activity via Astrocyte Coculture," The Journal of Neuroscience, 2007, 27(12):3069-3077.
Kim et al., "Efficient Specification of Interneurons from Human Pluripotent Stem Cells by Dorsoventral and Rostrocaudal Modulation," Stem Cells, 2014, 32:1789-1804.
Kobayashi et al., "Reduced inhibition of dentate granule cells in a model of temporal lobe epilepsy," J Neurosci., 2003, 23(6):2440-2452.
Krantz et al., "Cornelia de Lange syndrome is caused by mutations in NIPBL, the human homolog of *Drosophila melanogaster* Nipped-B," Nature Genetics, Jun. 2004, 36(6):631-635.
Krencik et al., "Specification of transplantable astroglial subtypes from human pluripotent stem cells," Nat Biotechnol., 2011, 29(6):528-534.
Kriks et al., "Dopamine neurons derived from human ES cells efficiently engraft in animal models of Parkinson's disease," Nature, 2011, 480:547-551.
Krupnik et al., "Functional and structural diversity of the human Dickkopf gene family," Gene, 1999, 238(2):301-313.
Le Magueresse et al., "GABAergic Intereurons Shape the Functional Maturation of the Cortex," Neuron, 2013, 77:388-405.
Lee et al., "Large-scale screening using familial dysautonomia induced pluripotent stem cells identifies compounds that rescue IKBKAP expression," Nat Biotechnol., 2012, 30:1244-1248.
Leksell et al., "A new fixation device for the Leksell stereotaxic system," J. Neurosurg., 1987, 66(4):626-629.
Leksell et al., "Stereotaxis and nuclear magnetic resonance," J. Neural. Neurosurg. Psychiatry, 1985, 48:14-18.
Leksell et al., "Stereotaxis and tomography a technical note," Acta. Neurochir., 1980, 52:1-7.
Li et al., "Coordination of sonic hedgehog and Wnt signaling determines ventral and dorsal telencephalic neuron types from human embryonic stem cells," Development, 2009, 136:4055-4063.
Li et al., "Prenatal immune challenge is an environmental risk factor for brain and behavior change relevant to schizophrenia: evidence from MRI in a mouse model," PLoS One, 2009, 4(7):e6354, 9 pages.
Lin et al., "RNA-Seq of human neurons derived from iPS cells reveals candidate long non-coding RNAs involved in neurogenesis and neuropsychiatric disorders," PLoS One, 2011, 6(9):e23356, 12 pages.
Liodis et al., "Lhx6 activity is required for the normal migration and specification of cortical interneuron subtypes," J Neurosci., 2007, 27(12):3078-3089.
Loscher et al., "Seizure suppression in kindling epilepsy by grafts of fetal GABAergic neurons in rat substantia nigra," J Neurosci Res., 1998, 51:196-209.
Ma et al., "Subcortical origins of human and monkey neocortical interneurons," Nat Neurosci., 2013, 16:1588-1597.
Madrazo et al., "Open Microsurgical Autograft of Adrenal Medulla to the Right Caudate Nucleus in Two Patients with Intractable Parkinson's Disease," New Engl. J. Med., 1987, 316(14):831-834.
Maisano et al., "Differentiation and functional incorporation of embryonic stem cell-derived GABAergic interneurons in the dentate gyrus of mice with temporal lobe epilepsy," J Neurosci, 2012, 32(1):46-61.
Mallon et al., "StemCellDB: the human pluripotent stem cell database at the National Institutes of Health," Stem Cell Research, 2013, 10:57-66.
Marco et al., "Inhibitory neurons in the human epileptogenic temporal neocortex. An immunocytochemical study," Brain, 1996, 119(Pt 4):1327-1347.
Mariani et al., "Modeling human cortical development in vitro using induced pluripotent stem cells," PNAS, 2012, 109(31):12770-12775.
Martinez-Cerdeno et al., "Embryonic MGE precursor cells grafted into adult rat striatum integrate and ameliorate motor symptoms in 6-OHDA-lesioned rats," Cell Stem Cell, 2010, 6:238-250.
Matsui et al., "Regeneration of the damaged central nervous system through reprogramming technology: Basic concepts and potential application for cell replacement therapy," Exp Neurol., 2014, 260(5):12-18.
Mazzuferi et al., "Rapid epileptogenesis in the mouse pilocarpine model: video—EEG, pharmacokinetic and histopathological characterization," Exp Neurol., 2012, 238:156-167.
Meechan et al., "Cxcr4 regulation of interneuron migration is disrupted in 22q11.2 deletion syndrome," PNAS, 2012, 109(45):18601-18606.

(56) References Cited

OTHER PUBLICATIONS

Momoy-Contreras et al., "Using Chemical Approaches to Understand RNA Structure and Function in Biology," J. Nucleic Acids, 2011, 2011:741723, 16 pages.
Muller et al., "Behavioral and cognitive alterations, spontaneous seizures, and neuropathology developing after a pilocarpine-induced status epilepticus in C57BL/6 mice," Exp Neurol., 2009, 219:284-297.
Nordstrom et al., "Progressive induction of caudal neural character by graded Wnt signaling," Nat Neurosci., 2002, 5(6):525-532.
Okaty et al., "Transcriptional and electrophysiological maturation of neocortical fastspiking GABAergic interneurons," J Neurosci., 2009, 29: 7040-7052.
Parekh et al., "Preclinical Development of Human Inhibitory Interneuron Cell Therapy (NTX-001) for Chronic Focal Epilepsy (2470)," Neurology, Apr. 2021, 96(15 Supplement), Abstract, 4 pages.
PCT International Preliminary Report on Patentability in International Appln. No. PCT/US2014/064085, dated May 19, 2016, 8 pages.
PCT International Search Report and Written Opinion in International Appln. No. PCT/US2014/064085, dated Feb. 23, 2015, 11 pages.
Penn et al., "The Adrenal Medullary Transplant Operation for Park in son's Disease: Clinical Observations in Five Patients," Neurosurgery, 1988, 22:999-1004.
Piper et al., "The neurodevelopmental hypothesis of schizophrenia: convergent clues from epidemiology and neuropathology," Psychiatr Clin North Am., 2012, 35(3):571-584.
Rallu et al., "Dorsoventral patterning is established in the telencephalon of mutants lacking both Gli3 and Hedgehog signaling," Development, 2002, 129:4963-4974.
Rice et al., "Status epilepticus causes long-term NMDA receptor-dependent behavioral changes and cognitive deficits," Epilepsia, 1998, 39:1148-1157.
Ruiz et al., "Hedgehog-Gli signalling and the growth of the brain," Nat Rev Neurosci., 2002, 3:24-33.
Shibley et al., "Pilocarpine-induced status epilepticus results in mossy fiber sprouting and spontaneous seizures in C57BL/6 and CD-1 mice," Epilepsy Res., 2002, 49:109-120.
Southwell et al., "Cortical plasticity induced by inhibitory neuron transplantation," Science, 2010, 327:1145-1148.
Spreafico et al., "Cortical dysplasia: an immunocytochemical study of three patients," Neurology, 1998, 50:27-36.
Sussel et al., "Loss of Nkx2.1 homeobox gene function results in a ventral to dorsal molecular respecification within the basal telencephalon: evidence for a transformation of the pallidum into the striatum," Development, 1999, 126:3359-3370.
Tamamaki et al., "Green fluorescent protein expression and colocalization with calretinin parvalbumin, and somatostatin in the GAD67-GFP knock-in mouse," J Comp Neural., 2003, 467:60-79.
Walia et al., "Side effects of antiepileptics—a review," Pain Practice, 2004, 4(3):194-203.
Wang et al., "Human iPSC-derived oligodendrocyte progenitor cells can myelinate and rescue a mouse model of congenital hypomyelination," Cell Stem Cell, 2013, 12:252-264.
Wichterle et al., "Young neurons from medial ganglionic eminence disperse in adult and embryonic brain," Nat Neurosci., 1999, 2:461-466.
Wieser, "ILAE Commission Report. Mesial temporal lobe epilepsy with hippocampal sclerosis," Epilepsia, 2004, 45(6):695-714.
Wonders et al., "The origin and specification of cortical interneurons," Nat Rev Neurosci., 2006, 7:687-696.
Xu et al., "De novo gene mutations highlight patterns of genetic and neural complexity in schizophrenia," Nat Genet, 2012, 44:1365-1369.
Xu et al., "Feeder-free growth of undifferentiated human embryonic stem cells," Nat. Biotechnol., 2001, 19:971-974.
Xu et al., "Temporal and spatial gradients of FGF8 and Fgf1 7 regulate proliferation and differentiation of midline cerebellar structures," Development, 2000, 127(9):1833-1843.
Yu et al., "Therapeutic translation of aspics for treating neurological disease," Cell Stem Cell, 2013, 12:678-688.
Ahn et al., "Differentiation of human pluripotent stem cells into Medial Ganglionic Eminence vs. Caudal Ganglionic Eminence cells," Methods, May 2016, 101:103-112, 10 pages.
Amariglio et al., "Donor-derived brain tumor following neural stem cell transplantation in an ataxia telangiectasia patient," PLoS Medicine, Feb. 2009, 6(2):e1000029, 11 pages.
Bagley et al., "Fused cerebral organoids model interactions between brain regions," Nature Methods, Jul. 2017, 14(7):743-751, 12 pages.
Bandler et al., "Cortical interneuron specification: the juncture of genes, time and geometry," Current Opinion in Neurobiology, Feb. 2017, 42:17-24.
Berkowitz et al., "Glioproliferative Lesion of the Spinal Cord as a Complication of "Stem-Cell Tourism"," The New England Journal of Medicine, Jul. 2016, 375(2):196-198, 3 pages.
Buchanan et al., "Cryopreservation of stem cells using trehalose: evaluation of the method using a human hematopoietic cell line," Stem Cells and Development, Jul. 2004, 13(3):295-305.
Carvalho and Irizarry, "A framework for oligonucleotide microarray preprocessing," Bioinformatics, Aug. 2010, 26(19):2363-2367.
Colasante et al., "Rapid Conversion of Fibroblasts into Functional Forebrain GABAergic Interneurons by Direct Genetic Reprogramming," Cell Stem Cell, Dec. 2015, 17(6):719-734.
Cunningham et al., "hPSC-derived maturing GABAergic interneurons ameliorate seizures and abnormal behavior in epileptic mice," Cell Stem Cell, Nov. 2014, 15(5):559-573.
Donegan et al., "Stem cell-derived interneuron transplants as a treatment for schizophrenia: preclinical validation in a rodent model," Molecular Psychiatry, Oct. 2017, 22(10):1492-1501, 10 pages.
Franco and Cedazo-Minguez, "Successful therapies for Alzheimers disease: why so many in animal models and none in humans?," Frontiers in Pharmacology, Jun. 2014, 5(146): 13 pages.
Gautier et al., "affy—analysis of Affymetrix GeneChip data at the probe level," Bioinformatics, Feb. 2004, 20(3):307-315.
Goldman, "Stem and Progenitor Cell-Based Therapy of the Central Nervous System: Hopes, Hype, and Wishful Thinking," Cell Stem Cell, Feb. 2016, 18(2):174-188.
Hoffman et al., "Transcriptional signatures of schizophrenia in hiPSC-derived NPCs and neurons are concordant with post-mortem adult brains," Nature Communications, Dec. 2017, 8(2225): 15 pages.
Hong et al., "Functional analysis of various promoters in lentiviral vectors at different stages of in vitro differentiation of mouse embryonic stem cells," Mol Ther, Sep. 2007, 15(9):1630-1639.
International Preliminary Report on Patentability in International Appln. No. PCT/US2019/053089, dated Apr. 8, 2021, 7 pages.
International Search Report and Written Opinion in International Appln. No. PCT/US2019/053089, dated Dec. 20, 2019, 9 pages.
Irizarry et al., "Exploration, normalization, and summaries of high-density oligonucleotide array probe level data," Biostatistics, Apr. 2003, 4(2):249-264.
Kauffmann et al., "arrayQualityMetrics—a bioconductor package for quality assessment of microarray data," Bioinformatics, Dec. 2008, 25(3):415-416.
Kemp et al., "Improving and accelerating the differentiation and functional maturation of human stem cell-derived neurons: role of extracellular calcium and GABA," The Journal of Physiology, Nov. 2016, 594(22):6583-6594.
Kikuchi et al., "Human iPS cell-derived dopaminergic neurons function in a primate Parkinson's disease model," Nature, Aug. 2017, 548(7669):592-596, 18 pages.
Lee et al., "Cryopreservation in trehalose preserves functional capacity of murine spermatogonial stem cells," PLoS One, 2013, 8(1):e54889, 9 pages.
Louvi and Artavanis-Tsakonas, "Notch signalling invertebrate neural development," Nature reviews Neuroscience, Mar. 2006, 7(2):93-102.
Marín, "Interneuron dysfunction in psychiatric disorders," Nature Reviews Neuroscience, Jan. 2012, 13(2):107-120.
Monzel et al., "Derivation of Human Midbrain-Specific Organoids from Neuroepithelial Stem Cells," Stem Cell Reports, May 2017, 8(5):1144-1154.

(56) References Cited

OTHER PUBLICATIONS

Morozov et al., "Introduction to integral discriminants," Journal of High Energy Physics, 2009, 40 pages.
Ni et al., "Large-scale generation and characterization of homogenous populations of migratory cortical interneurons from human pluripotent stem cells," Molecular Therapy Methods and Clinical Development, Jun. 2019, 13:414-430.
Ogawa et al., "Glioblastoma Model Using Human Cerebral Organoids," Cell Reports, Apr. 2018, 23(4):1220-1229.
Qian et al., "Brain-Region-Specific Organoids Using Mini-bioreactors for Modeling ZIKV Exposure," Cell, May 2016, 165(5):1238-1254, 18 pages.
Rhee et al., "Protein-based human iPS cells efficiently generate functional dopamine neurons and can treat a rat model of Parkinson disease," The Journal of Clinical Investigation, May 2011, 121(6):2326-2335.
Rigamonti et al., "Large-Scale Production of Mature Neurons from Human Pluripotent Stem Cells in a Three-Dimensional Suspension Culture System," Stem Cell Reports, Jun. 2016, 6(6):993-1008.
Rosen et al., "Type 1 astrocytes inhibit myelination by adult rat oligodendrocytes in vitro," The Journal of Neuroscience, Oct. 1989, 9(10):3371-3379.
Saxena et al., "Trehalose-enhanced isolation of neuronal sub-types from adult mouse brain," BioTechniques, Jun. 2012, 52(6):381-385.
Schwartz et al., "Phase I study of PD 0332991, a cyclin-dependent kinase inhibitor, administered in 3-week cycles (Schedule 2/1)," British Journal of Cancer, Jun. 2011, 104(12):1862-1868.
Southwell et al., "Interneurons from embryonic development to cell-based therapy," Science, Apr. 2014, 344(6180):1240622, 10 pages.
Sun et al., "Direct Induction and Functional Maturation of Forebrain GABAergic Neurons from Human Pluripotent Stem Cells," Cell Reports, Aug. 2016, 16(7):1942-1953.
Tabar and Studer, "Pluripotent stem cells in regenerative medicine: challenges and recent progress," Nature Reviews Genetics, Jan. 2014, 15:82-92.
Takahashi and Yamanaka, "Induction of pluripotent stem cells from mouse embryonic and adult fibroblast cultures by defined factors," Cell, Aug. 2006, 126(4):663-676.
Telezhkin et al., "Forced cell cycle exit and modulation of GABAA, CREB, and GSK3beta signaling promote functional maturation of induced pluripotent stem cell-derived neurons," American Journal of Physiology Cell Physiology, Dec. 2015, 310:C520-541.
Thomsen et al., "Cognitive improvement by activation of alpha7 nicotinic acetylcholine receptors: from animal models to human pathophysiology," Current Pharmaceutical Design, Jan. 2010, 16(3):323-343.
Tischfield et al., "Atypical PKC and Notch Inhibition Differentially Modulate Cortical Interneuron Subclass Fate from Embryonic Stem Cells," Stem Cell Reports, May 2017, 8(5):1135-1143.
Wang et al., "Lingo-1 shRNA and Notch signaling inhibitor DAPT promote differentiation of neural stem/progenitor cells into neurons," Brain Research, Mar. 2016, 1634:34-44, 11 pages.
Wonders and Anderson, "Cortical interneurons and their origins," The Neuroscientist, Jun. 2005, 11(3):199-205.
Xiang et al., "Fusion of Regionally Specified hPSC-Derived Organoids Models Human Brain Development and Interneuron Migration," Cell Stem Cell, Sep. 2017, 21(3):383-398.e7.
Yang et al., "Generation of pure GABAergic neurons by transcription factor programming," Nature Methods, Jun. 2017, 14(6):621-628, 10 pages.
Yoon and Gaiano, "Notch signaling in the mammalian central nervous system: insights from mouse mutants," Nat Neurosci, Jun. 2005, 8(6):709-715.
Zhao et al., "Stem cell therapies for retinal diseases: recapitulating development to replace degenerated cells," Development, Apr. 2017, 144(8):1368-1381.
Zhu et al., "Cortical GABAergic Interneuron/Progenitor Transplantation as a Novel Therapy for Intractable Epilepsy," Frontiers in Cellular Neuroscience, Jun. 2018, 12(167): 9 pages.

* cited by examiner

SEQUENCE LISTING

<160> NUMBER OF SEQ ID NOS: 44

<210> SEQ ID NO 1
<211> LENGTH: 140
<212> TYPE: PRT
<213> ORGANISM: Homo sapiens

<400> SEQUENCE: 1

Met Ala Glu Asp Gly Asp Pro Phe Ala Lys Leu Ile Val Glu Thr Asp
1               5                   10                  15

Thr Phe Gly Ser Arg Val Arg Val Arg Gly Ala Glu Thr Gly Leu Tyr
            20                  25                  30

Ile Cys Met Asn Lys Lys Gly Lys Leu Ile Ala Lys Ser Asn Gly Lys
        35                  40                  45

Gly Lys Asp Cys Val Phe Thr Glu Ile Val Leu Glu Asn Asn Tyr Thr
    50                  55                  60

Ala Leu Gln Asn Ala Lys Tyr Glu Gly Trp Tyr Met Ala Phe Thr Arg
65                  70                  75                  80

Lys Gly Arg Pro Arg Lys Gly Ser Lys Thr Arg Gln His Gln Arg Glu
                85                  90                  95

Val His Phe Met Lys Arg Leu Pro Arg Gly His His Thr Thr Glu Gln
            100                 105                 110

Ser Leu Arg Phe Glu Phe Leu Asn Tyr Pro Pro Phe Thr Arg Ser Leu
        115                 120                 125

Arg Gly Ser Gln Arg Thr Trp Ala Pro Glu Pro Arg
    130                 135                 140

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
atacctcttc cagccagac                                                   19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gctcgccatt gaaaaccatc 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
acctgtctgc taaagaaacc 20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ggggatgggg gagtaaaaaa taac 24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
caaccagacg gagaatgatg 20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gctgaagact tggaggatta g 21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
taggtaacaa gcgactgggg 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gggctgaaaa taggaaaagg c 21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
aaggcaagga aaggctctgg 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ccgttcaagt caaacatccg 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tcttctcaca gacttcggc 19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
catttgtttt ctaaggcggg 20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
atacaaaccc cgaccgaaac gcac 24

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ccgccatctg tcttcatac 19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
aacaccactt tgtctctgag 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggtagtttgg cacacctaac 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gcagtatgat gtctcctacg 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtattcagcc agttccagg 19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
tgctggagac aaagatgggg ac 22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
attgggtgtt cagggcagag ag 22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcaggatgaa atgaggcttg 20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
caggatgtga aagtcttcca g 21

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gctgcgacac tacatcaac 19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ctcatttccc atcaccacat tg 22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tcctgccaac cgaagagaac 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tagccactcc tgtctgtgtc 20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ctctttacag ggcaccttc 19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ggtcttctga gatgttactg c 21

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
agcaactgat gaggtctcg 19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
caccaggata cacaacacc 19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aaatcgtagg tgttggctc 19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gatacccagt ttgaggttcc 20

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
cgcgatcaaa cccatttgaa tcaccaaaga tcgcg 35

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 35
cgcgatcggc caggttgtta agaagatcgc g 31

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 36
cgcgatcgaa gcggtgaggc agagcggatc gcg 33

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 37
cgcgatcccc ggcgtcctct cacgatcgcg 30

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 38
cgcgatcatg gtgccgtagt ccgaggatcg cg 32

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic probe

<400> SEQUENCE: 39
cgcgatccag acactgagaa cggagtcgat cgcg 34

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 40
cgcgatcgat tcggcggcgg ctggatcgcg 30

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
cgcgatcgcc ttcccactgc ctccggatcg cg 32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 42
cgcgatcacc acatcgggct tcgctggatc gcg 33

<210> SEQ ID NO 43
<211> LENGTH: 2267
<212> TYPE: DNA
<213> ORGANISM: Homo sapiens

<400> SEQUENCE: 43
ctcgagctcc ccacttcctg ggcttctggg gctggggtct tagcatcttc tcccaggcct 60
cccctccccc ataggtggct gccctggggc cagggaaccg aagtcctggg ggggtgagag 120
gggcaggtgg ggagacgggt ggccagactg gtgggcagga ggccagagca ggccaggctc 180
tgggcccctc tctctgtctt tctgcgttgg ggcccagccc tccgtagaca accatgtgtc 240
actgctgcct gggaaggaca ggaagttgcc gggtgggctg cgagttgtga gggattagag 300
agcgggtgcc caggcagggg ggtggggctg cggctcctgc ccacctcgcc atctgctggg 360
gtgcccacct gctgtctggg gccgctcgcc ctctgcctct gctggggggg ctctgtaacg 420
tggtgtctgg ctcccctacc tgcagagcaa cggcaaaggc aaggactgcg tcttcacgga 480
gattgtgctg gagaacaact acacagcgct gcagaatgcc aagtacgagg gctggtacat 540
ggccttcacc cgcaagggcc ggccccgcaa gggctccaag acgcggcagc accagcgtga 600
ggtccacttc atgaagcggc tgccccgggg ccaccacacc accgagcaga gcctgcgctt 660
cgagttcctc aactacccgc ccttcacgcg cagcctgcgc ggcagccaga ggacttgggc 720
cccgagcccc cgatagtgct gcctggccct ccccacaatg ccagaccgca gagaggctca 780
tcctgtaggg cacccaaaac tcaagcaaga tgagctgtgc gctgctctgc aggctgggga 840
ggtgctgggg gagccctggg ttccggttgt tgatattgtt tgctgttggg tttttgctgt 900 ttttttttt ttttttttt ttaaaacaaa agagaggctc tatttttgta ttccacttgg 960

```
ctgtggtgtc tgtcttctta actctcagaa agctccatta gtggcctaga ctgggattcc   1020

ggctgggggt ttgcgggggt ggggggcttt ctctagcctg tgctgctgag gccccagtac   1080

ctccagggcc agttggctgg gcagccaggg actccactgc acccccaggt ggggcaggga   1140

ggaaaggact gtgacatagg gcagtcctct tagaagtggg tatcagactg gtggctatta   1200

aatgattgaa atatttattt aacttgcata ttaaaaatgt gtgctggaga gtgagtcctg   1260

ccggggtcag cccctccctc caaccttgcc ccagctggtg ggcggctggg agacgcagat   1320

gaccaggtgc cagctctgac cacagcctcc ctccagccta aagacacctg cctgtcaacc   1380

atccccatca ctgtcacttg aggggttttc ctgcaaggac agaagcaggg aaaggggcaa   1440

gaagaggctc ttagctagtc cttggagctc tcagatgtgt acctcctagc actttacaga   1500

ggtcattgct aacacttccc caggccacct cagggccaga aataatggat gtgctagggc   1560

tagagctgta atcatggatt taatcctctt aaaaagtgct tctctgagtg cctaggtcca   1620

tgtgggagac aggttggaga ttccagaact tgctctttct gagactcagg ctccagaaaa   1680

tgaaagaaaa gagcagctgc cagggtccaa ggtgggggca tattggaggg ggaccaccaa   1740

gactggtgtt gacaatggtg atgtgggaca agtgttaacc ttgggtgata tggtgagata   1800

gctgtgggca gaaagcactg agctgaggtg cggcgaggag cctggggaac tgtcttccag   1860

gaagaggctg cccacctcgg aggatgggct ggcgggagag gagctgggca ccggatggca   1920

ccagaaggga agctcatagg cctagcgcag aactaaaggc agtcatagcc ttggggagaa   1980

gcaggaggcc gtatgtggag ggagggaggg ctgctgtggg agtggtggag caggtcatgg   2040

tgtgggcaga gaagggaatg ggcaagggtg caggtgtgtg tttgcgtgtg gactggtgag   2100

actggtgtcc tgccacaccg agggagagcc caggccccac ggcagtttcc tgagtgcaga   2160

gctggcccag gcttcatcgc tgaggcctcc cattagggct gctcctgctt ccttccttgt   2220

ggatgccctg ggctggtccc acagcccagc tactgagcca gtctaga                 2267
```

<210> SEQ ID NO 44
<211> LENGTH: 2197
<212> TYPE: DNA
<213> ORGANISM: Homo sapiens

<400> SEQUENCE: 44

```
ctgacagaca cgtagaccaa cagtgcggcc ccagggttcg tccccagact cgctcgctca     60

tttgttggcg actggggctc agcgcagcga agcccgatgt ggtccggagg cagtgggaag    120

gcgcggggct gggaggccgc ggcgggaggg aggagcagcc ccggcaggct cagccgccgc    180

cgaatcatgt cgatgagtcc aaagcacacg actccgttct cagtgtctga catcttgagt    240

cccctggagg aaagctacaa gaaagtgggc atggagggcg gcggcctcgg ggctccgctg    300

gcggcgtaca ggcagggcca ggcggcaccg ccaacagcgg ccatgcagca gcacgccgtg    360

gggcaccacg gcgccgtcac cgccgcctac cacatgacgg cggcgggggt gccccagctc    420

tcgcactccg ccgtgggggg ctactgcaac ggcaacctgg gcaacatgag cgagctgccg    480

ccgtaccagg acaccatgag gaacagcgcc tctggccccg gatggtacgg cgccaaccca    540

gacccgcgct tccccgccat ctcccgcttc atgggcccgg cgagcggcat gaacatgagc    600

ggcatgggcg gcctgggctc gctgggggac gtgagcaaga acatggcccc gctgccaagc    660

gcgccgcgca ggaagcgccg ggtgctcttc tcgcaggcgc aggtgtacga gctggagcga    720

cgcttcaagc aacagaagta cctgtcggcg ccggagcgcg agcacctggc cagcatgatc    780

cacctgacgc ccacgcaggt caagatctgg ttccagaacc accgctacaa aatgaagcgc    840
```

-continued

```
caggccaagg acaaggcggc gcagcagcaa ctgcagcagg acagcggcgg cggcgggggc    900
ggcgggggca ccgggtgccc gcagcagcaa caggctcagc agcagtcgcc gcgacgcgtg    960
gcggtgccgg tcctggtgaa agacggcaaa ccgtgccagg cgggtgcccc cgcgccgggc   1020
gccgccagcc tacaaggcca cgcgcagcag caggcgcagc accaggcgca ggccgcgcag   1080
gcggcggcag cggccatctc cgtgggcagc ggtggcgccg gccttggcgc acacccgggc   1140
caccagccag gcagcgcagg ccagtctccg gacctggcgc accacgccgc cagccccgcg   1200
gcgctgcagg gccaggtatc cagcctgtcc cacctgaact cctcgggctc ggactacggc   1260
accatgtcct gctccacctt gctatacggt cggacctggt gagaggacgc cgggccggcc   1320
ctagcccagc gctctgcctc accgcttccc tcctgcccgc cacacagacc accatccacc   1380
gctgctccac gcgcttcgac ttttcttaac aacctggccg cgtttagacc aaggaacaaa   1440
aaaaccacaa aggccaaact gctggacgtc tttctttttt tcccccccta aaatttgtgg   1500
gttttttttt ttaaaaaaag aaaatgaaaa acaaccaagc gcatccaatc tcaaggaatc   1560
tttaagcaga gaagggcata aaacagcttt ggggtgtctt tttttggtga ttcaaatggg   1620
ttttccacgc tagggcgggg cacagattgg agagggctct gtgctgacat ggctctggac   1680
tctaaagacc aaacttcact ctgggcacac tctgccagca aagaggactc gcttgtaaat   1740
accaggattt tttttttttt ttgaagggag gacgggagct ggggagagga aagagtcttc   1800
aacataaccc acttgtcact gacacaaagg aagtgccccc tccccggcac cctctggccg   1860
cctaggctca gcggcgaccg ccctccgcga aaatagtttg tttaatgtga acttgtagct   1920
gtaaaacgct gtcaaaagtt ggactaaatg cctagttttt agtaatctgt acattttgtt   1980
gtaaaaagaa aaaccactcc cagtccccag cccttcacat tttttatggg cattgacaaa   2040
tctgtgtata ttatttggca gtttggtatt tgcggcgtca gtctttttct gttgtaactt   2100
atgtagatat ttggcttaaa tatagttcct aagaagcttc taataaatta tacaaattaa   2160
aaagattctt tttctgatta aaaaaaaaaa aaaaaaa                            2197
```

METHODS FOR EFFICIENT GENERATION OF GABAERGIC INTERNEURONS FROM PLURIPOTENT STEM CELLS

CROSS-REFERENCE TO RELATED APPLICATIONS

This application is a 35 U.S.C. § 371 National Phase Entry Application of International Application No. PCT/US14/64085 filed Nov. 5, 2014, which designates the U.S. and claims benefit under 35 U.S.C. 119(e) of U.S. Provisional Patent Application Ser. No. 61/901,541 filed on Nov. 8, 2013, and U.S. Provisional Patent Application Ser. No. 62/053,535 filed on Sep. 22, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 11, 2014, is named 063476-080192-PCT_SL.txt and is 16,870 bytes in size.

FIELD OF INVENTION

One aspect of the present invention relates to an enhanced method for the generation of medial ganglionic eminence (MGE) cells from pluripotent stem cells. The method comprises a step of contacting the differentiating cells with an activator of FGF8 signaling. Another aspect of the present invention relates to the suppression of seizures in a subject by transplantation of MGE cells, or GABAergic interneurons, that are derived from human pluripotent stem cells. Also provided are methods for the isolation of MGE cells and interneurons from differentiation progenies of pluripotent stem cells.

BACKGROUND

During early development, cortical interneuron progenitors arise from the ventral telencephalic area such as Medial Ganglionic Eminence (MGE) and Caudal Ganglionic Eminence (CGE) (Wonders C P, Anderson S A. Nat Rev Neurosci. 2006, 7: 687-696). Among these, MGE progenitors mostly generate parvalbumin-expressing interneurons or somatostatin-expressing interneurons comprising about 65% of the entire cortical interneuron population, whereas CGE cells mostly generate calretinin-expressing interneurons (Tamamaki N, et al. J Comp Neurol. 2003, 467:60-79).

GABAergic interneurons regulate cortical neural networks by providing inhibitory inputs, and their malfunction, resulting in failure to intricately regulate neural circuit balance, is implicated in brain diseases such as Schizophrenia, Autism and Epilepsy. During early development, GABAergic interneuron progenitors arise from the ventral telencephalic area such as Medial Ganglionic Eminence (MGE) and caudal ganglionic eminence (CGE) by the actions of secreted signaling molecules from nearby organizers, and migrate to their target sites where they form local synaptic connections.

Methods for the generation of MGE cells from human pluripotent stem cells (hPSCs) are known in the art, however such methods do not consistently generate a large population of MGE cells (Nicholas C R, et al. Functional Maturation of hPSC-Derived Forebrain Interneurons Requires an Extended Timeline and Mimics Human Neural Development. Cell Stem Cell. 2013, 12:573-586; Maroof A M, et al. Directed differentiation and functional maturation of cortical interneurons from human embryonic stem cells. Cell Stem Cell. 2013, 12:559-572; and Liu Y, et al. Medial ganglionic eminence-like cells derived from human embryonic stem cells correct learning and memory deficits. Nat Biotechnol. 2013, 31:440-447).

Accordingly, there remains a need in the art for efficient and consistent generation of MGE cells, which will lead to a better safety profile in therapeutic treatment, as MGE cells can be further differentiated into GABAergic interneurons. Dysfunction of interneurons has been implicated in various brain diseases such as Epilepsy, Schizophrenia and Autism (Arber C E, Li M. Frontiers in Cellular Neuroscience 2013, 7), which are conditions awaiting more effective treatments. In addition, defined populations of MGE cells are a valuable resource for disease modeling and therapeutic screening.

SUMMARY

Herein we show that sonic hedgehog (SHH) activation during early human neural development elicits a pleiotropic downstream cascade, by inducing rostralizing FGF8 signaling as well as caudalizing FGF15/19 signaling, as observed during early mouse development. The dual effect of SHH on rostral-caudal boundary determination causes medial ganglionic eminence (MGE) derivation stochasticity depending on the fine balance of its downstream cascade. Thus, we tested the combination of early activation of SHH with the addition of an exogenous activator of FGF8 signaling (e.g. exogenous rostralizing factor FGF8) during differentiation of pluripotent stem cells, and assessed the effect on differentiation of the population of pluripotent stem cells. We have identified that adding exogenous activator of FGF8 consistently results in >80% by FACS of MGE cells from multiple hPSCs. The MGE cells generated share characteristics with their in vivo counterpart, such as spontaneous differentiation into Lhx6-expressing and migrating GABAergic interneurons that can generate GABA, fire action potentials and form functional GABAergic synaptic connections. Transplantation of human MGE cells into rodent brains yields well-contained neural grafts enriched with GABAergic interneurons that migrate in the host brain and mature to express somatostatin or parvalbumin. Thus, one aspect of the invention provides an enhanced method for the production of MGE cells from a population of pluripotent stem cells. The enhanced method adds an additional step to the basic differentiation protocol that uses a SMAD inhibitor to drive the cells towards neuroectoderm, and an activator of sonic hedgehog to drive the cells to differentiate into ventral telencephalic neuroectoderm. The additional step comprises contacting the pluripotent stem cells with an exogenous activator of FGF8 signaling during the differentiation protocol. The method represents a novel tool for generation of MGE cells for therapeutic use, and for use in developmental studies, disease modeling, bioassays, and drug screening.

In addition, herein we demonstrate, for the first time, that transplantation of MGE cells derived from pluripotent stem cells successfully mature into GABAergic neurons, migrate throughout the hippocampus, and integrate into the host neural circuitry allowing receipt of excitatory inputs, and release of GABA that induces inhibition of spontaneous seizures. Accordingly, another aspect of the invention provides methods for suppression of seizure activity in a subject comprising administering MGE cells derived from pluripotent stem cells into a subject in need of treatment.

In one aspect of the invention a method for the generation of a population of medial ganglionic eminence (MGE) cells from pluripotent stem cells is provided. The method comprises the steps of a) contacting a population of pluripotent stem cells with a SMAD inhibitor to generate a population of cells that express the neuroectoderm cell marker Pax6, b) contacting the cells of step a) with an activator of sonic hedgehog (SHH) to generate a population of cells that express ventral telencephalic neuroectoderm marker FoxG1; and c) contacting the cells of step b) with an activator of FGF8 signaling to produce a population of cells that comprises an increased percentage of MGE cells that express the transcription factor NKX2.1 as compared to cells of step b) that have not been contacted with the FGF8 activator.

In certain embodiments, 50% or greater of the cells in the population of step c) express the MGE cell marker NKX2.1. In one embodiment, 60% or greater of the cells in the population of step c) express the MGE cell marker NKX2.1. In one embodiment, 70% or greater of the cells in the population of step c) express the MGE cell marker NKX2.1. In one embodiment, 80% or greater of the cells in the population of step c) express the MGE cell marker NKX2.1.

In certain embodiments, 10% or less of the cells in the population of step c) express, the caudal ganglionic eminence (CGE) cell marker, CoupTFII. In certain embodiments, less 20% or less, 25% or less, or 30% or less, of the cells in the population express the caudal ganglionic eminence (CGE) cell marker, CoupTFII.

In one embodiment, the MGE cells further express the transcription factor Olig2.

In one embodiment, the activator of FGF8 signaling is exogenous FGF8 protein, or an exogenous peptidomimetic of FGF8 protein.

In one embodiment, the MGE cells are capable of differentiating into GABAergic interneurons that express Lhx6 protein and Sox6.

In one embodiment, the activator of sonic hedgehog is smoothened agonist (SAG).

In one embodiment, the inhibitor of SMAD comprises LDN193189 and SB431542.

In one embodiment, the pluripotent stem cells are human cells.

In one embodiment, the pluripotent stem cells are embryonic stem cells.

In one embodiment, the pluripotent stem cells are induced pluripotent stem cells.

In one embodiment, pluripotent stem cells are cultured as embryoid bodies.

In one embodiment, the pluripotent stem cells are cultured in suspension.

In one embodiment, the pluripotent stem cells are cultured as adherent cells.

In one embodiment, the method further comprises contacting the population of pluripotent stem cells with an inhibitor of Wnt.

In one embodiment, the method further comprises differentiating the population of cells comprising MGE cells into GABAergic interneurons that express the cell marker Lhx6 and Sox6.

In one embodiment, the MGE cells are differentiated by culturing the MGE for a time sufficient to allow for the MGE cells to spontaneously differentiate into GABAergic interneurons.

In one embodiment, the GABAergic interneurons generates GABA.

In one embodiment, the GABAergic interneurons further differentiate to express somatostatin or parvalbumin.

In one embodiment, the population of MGE cells are further enriched for MGE cells, for example by selecting for and isolating the MGE cells from the population.

In another aspect of the invention, methods are provided for treatment of a neurological disorders comprising administering to a subject in need of treatment the isolated population of MGE cells obtained by a method of generation of a population of medial ganglionic eminence (MGE) cells from pluripotent stem cells. The method comprises the steps of a) contacting a population of pluripotent stem cells with a SMAD inhibitor to generate a population of cells that express the neuroectoderm cell marker Pax6, b) contacting the cells of step a) with an activator of sonic hedgehog (SHH) to generate a population of cells that express ventral telencephalic neuroectoderm marker Dlx1; and c) contacting the cells of step b) with an activator of FGF8 signaling to produce a population of cells that comprises an increased percentage of MGE cells that express the transcription factor NKX2.1 as compared to cells that have not been contacted with the FGF8 activator.

In one embodiment, the subject in need of treatment is diagnosed as having seizures, or as having a neurological disorder selected from the group consisting of Alzheimer's disease, Parkinson's disease, Huntington's disease, neuropathic pain, epilepsy, autism, and schizophrenia, In one embodiment, the pluripotent stem cells are allogenic cells.

In one embodiment, the cells are administered by transplantation.

In yet another aspect of the invention, methods for suppression of spontaneous seizure activity in a subject are provided. The methods comprise administering MGE cells derived from pluripotent stem cells to a subject in need of treatment, e.g. MGE cells obtained by the method of a) contacting a population of pluripotent stem cells with a SMAD inhibitor to generate a population of cells that express the neuroectoderm cell marker Pax6, b) contacting the cells of step a) with an activator of sonic hedgehog (SHH) to generate a population of cells that express ventral telencephalic neuroectoderm marker Dlx1.

In one embodiment, the subject is diagnosed as having epilepsy.

In one embodiment, the MGE cells are derived from human pluripotent stem cells.

In one embodiment, the MGE cells are derived from induced pluripotent stem cells.

In one embodiment, the MGE cells are derived from embryonic pluripotent stem cells.

In one embodiment, the pluripotent stem cells are allogenic cells.

In one embodiment, the MGE cells are further differentiated into GABAergic interneurons that express Lhx6 and Sox6 prior to administration to the subject.

In one embodiment, the population of MGE cells are further enriched for MGE cells, for example by selecting for and isolating the MGE cells from the population.

In one embodiment, the cells are administered by transplantation.

BRIEF DESCRIPTION OF THE DRAWINGS

FIG. 1*a*, strong SHH signaling directs differentiating human H9 cells into MGE phenotype, assayed by immunocytochemistry and cell counting after 25 days of differentiation (Mean+S.E.M.; n=4, P<0.05, two tailed t-test). MGE derivation was optimized from H9 cells by various combinations and timing of signaling activation, assayed by flow cytometry analysis after 25 days of differentiation. FIG. 1*b*, real time PCR analysis of differentiating ES cells with or without 3 days' treatment with SAG (Mean+S.E.M.; n=4, P<0.05, two tailed t-test). FIG. 1*c*, FGF8 signaling further induced MGE phenotype at the expense of the CGE phenotype as shown by immunocytochemistry and cell counting analysis (Mean+S.E.M.; n=3, P<0.05, two tailed t-test). White scale bar: 100 μm.

FIG. 2*a*, real time PCR analysis of different treatment conditions, assayed after 25 days of differentiation (Mean+S.E.M.; n=4, P<0.05, two tailed t-test). FIG. 2*b*, SAG treatment during the 3rd week further enhanced MGE derivation, assayed after 25 days of differentiation (Mean+S.E.M.; n=3, P<0.05, two tailed t-test).

FIG. 3*a*, FGF8 treatment induces MGE phenotype while FGF19 induces CGE phenotype, shown by immunocytochemistry (not shown) and cell counting analysis after 3 weeks of differentiation (Mean+S.E.M.; n=3, P<0.05, two tailed t-test). No effect on diencephalic differentiation by FGF19 immunocytochemistry (not shown). FIGS. 3*b*-3*c* FGF8 treatment increases FGF19 expression, but FGF19 treatment does not affect FGF8 expression. Real time PCR analysis of differentiating ES cells (Mean+S.E.M.; n=3, P<0.05, two tailed t-test).

FIG. 4*a*, a schematic overview of optimized MGE derivation protocols. FIG. 4*b*, a graph gene expression analysis during MGE derivation of H9 cells, assayed by real time PCR (Mean+S.E.M.; n=3). Combined and temporal treatment with IWP2, SAG and FGF8 results in robust induction of MGE cells from H9 and H7 hESCs as well as iPSC2497, assayed after 25 days of differentiation (immunocytochemistry, data not shown). FIG. 4*c*, FACS analysis of MGE generation of H9 cells after Nkx2.1 staining Derived cells highly express independent ventral telencephalic marker Olig2 and telencephalic marker FoxG1, assayed after 25 days of differentiation (immunocytochemistry, data not shown).

FIG. 5*a*, combined and temporal treatments with IWP2, SAG and FGF8 generate mostly GABAergic neurons from differentiating H9 cells, whereas in the absence of such treatment, few cells become GABAergic neurons. Immunocytochemistry and cell counting analysis after 6 weeks of differentiation (Mean+S.E.M.; n=4, P<0.05, two tailed t-test). H7 and iPSC2497-derived MGE cells also generate GABAergic neuron-enriched cultures (immunocytochemistry data not shown). FIG. 5*b*, human PSC-derived MGE cells generate Lhx6+ neurons (Mean+S.E.M.; n=4, P<0.05, two tailed t-test. s. Human PSC-derived MGE cells generate Sox6+ GABAergic neurons. Some MGE-derived cells express Calbindin, Parvalbumin or Somatostatin (immunocytochemistry data not shown).

FIG. 6*a*, Quantification of migrating cell numbers per sphere after 5 days in culture on Matrigel. Migrating cell numbers were normalized to total cell numbers in the sphere (Mean+S.E.M.; n=3, P<0.05, two tailed t-test). FIG. 6*b*, Image software was used to assess each cell migration distance between the edge of the sphere and the center of the migrating cell body (Mean+S.E.M.; n=3, P<0.05, two tailed t-test). FIG. 6*c*, Schematic of transplantation of control and MGE spheres (dotted circle) into the ventral telencephalon. The dotted line points to route of migration of cells that emanated from the spheres. Dotted squares outline panels/areas in which the numbers of migrating cells were quantified. Low magnification images (4.2×) of control and MGE sphere transplantations into E13.5 CD1 telencephalon were taken (data not shown). Many cells were located close to the site of control sphere transplantation, and few cells were observed migrating from ventral to dorsal telencephalon. There was a decreased cell migration into dorsal telencephalon. In MGE sphere transplantation, many QDot® labeled cells migrated into the dorsal telencephalon. Images (10×, 30× and 60× images) of the dorsal telencephalon were also taken (data not shown) showing cells labeled with QDot® nanocrystals and anti-NCAM. FIG. 6*d*, Quantification of relative NCAM positive cell numbers from cortical and MGE spheres in three panels of the telencephalon, after normalization using the average total cell numbers from parallel control and MGE spheres (*P<0.001, n=7).

FIG. 7*a*, Quantification of migrating cell numbers per total cell numbers in each sphere after 5 days in culture on Matrigel (Mean+S.E.M.; n=4, P<0.05, two tailed t-test). FIG. 7*b*, ImageJ software was used to assess each cell migration distance between the edge of the sphere and the center of the migrating cell body (Mean+S.E.M.; n=3, P<0.05, two tailed t-test). Mouse MGE explant or human MGE spheres were embedded in matrigel substrate and their 3 dimensional migrations were analyzed 2 days after embedding (data not shown).

FIG. 8*b*, Representative traces of action potential firings induced by depolarizing current injection (500 ms long) in H9-derived MGE cells after 6 weeks and 12 weeks of differentiation. Injected currents are indicated. FIG. 8*c*. Traces showing currents evoked by voltage pulses. Membrane potential was held at −70 mV in voltage-clamp mode. Left, square voltage pulses from −70 mV to 20 mV in increments of 10 mV (20 ms long) induced both transient inward and sustained outward currents (1). Middle, the application of tetrodotoxin (1 μM) selectively blocked transient component (2). Sustained outward currents insensitive to tetrodotoxin are likely mediated by voltage-gated K+ channels (dotted line and open circle). Right, traces recorded under control conditions (1) were subtracted from currents recorded in the presence of tetrodotoxin (2) to calculate voltage-gated Na+ currents at different membrane potentials (filled circle). FIG. 8*d*, Current-voltage plots of voltage-dependent Na+ and K+ currents from traces as in f (filled and open circles, respectively; Mean±S.E.M.; n=4 cells). FIG. 8*e*, Traces showing spontaneous postsynaptic currents. Left, spontaneous postsynaptic currents were recorded at −70 mV in voltage-clamp mode (upper trace). A lower trace is the average of spontaneous currents recorded in the same cell. Decay time constant (TD) was calculated by fitting the decay phase of the trace to a single exponential function (indicated by a dotted curve). Middle, the application of bicuculline (30 μM) blocked postsynaptic currents completely. Right, spontaneous postsynaptic currents were recovered fully after bicuculline washout. FIG. 8*f*, Summary plot of e. Numbers of spontaneous postsynaptic currents were counted, and frequency per minute was calculated for each condition (Mean+S.E.M.; n=4 cells, *p<0.05, paired t test).

FIG. 11*a* overall experimental design. hPSC-derived MGE cells were transplanted into the hippocampus of TLE mice. Behavioral analysis was conducted after 3 months PT and histology analysis at 4 months PT. Two weeks PT, transplanted cells display minimal migration, shown by human cytoplasm-specific antibody staining (data not shown).

FIG. 11*b*, Quantification of migration of transplanted cells (Mean+S.E.M.; P<0.05, two tailed t-test) 2 week PT (n=3) and 4 month PT (n=8).

FIG. 12*a*, Cell counting analysis of 2 weeks PT vs. 4 months PT (Mean+S.E.M.; n=3, P<0.05, two tailed t-test). FIG. 12*b*, Cell counting analysis at 4 months PT (n=3); SST, somatostatin; PV, parvalbumin; Calr, calreticulin; NPY, neuropeptide Y; Calb, calbindin.

FIG. 13*a*, Top, a microscopic image showing the distribution of grafted human mGIN in the hippocampus. Channelrhodopsin 2 (ChR2)/GFP-expressing human MGE cells (green) transplanted into the cornu ammonis region 3 (CA3) of the hippocampus, migrate extensively to the CA1 and dentate gyrus (DG). The graft core is indicated by an asterisk. Strata oriens (s.o.), pyramidale (s.p.), and radiatum (s.r.) are also indicated. Bottom, confocal microscopic images showing that the recorded grafted cell, labeled with biocytin-streptavidin, expresses ChR2-GFP. FIG. 13*b*, Whole-cell patch-clamp recordings were performed with grafted cells expressing ChR2-GFP. Grafted human mGIN were identified with green fluorescence in acute brain slices. Biocytin was included in the pipette solution to label the recorded cells. Left, representative traces of ChR2-mediated currents in a grafted cell. These inward currents were induced by blue light illuminations (470 nm, 1 s pulses, blue horizontal bar) with variable intensities (0.02-0.61 mW/mm2) and recorded at −80 mV in voltage-clamp mode (V-clamp). Right, a summary graph showing the peak amplitude of ChR2-mediated currents plotted versus light power. ChR2 currents were larger in human mGIN 4-5 months after transplantation (n=16 cells) than in cells 2-3 months after implantation (n=9 cells) (p<0.001). FIG. 13*c*, Representative traces of action potentials (AP) evoked by short pulses of blue light illumination (1 ms, 12.5 mW/mm2, blue vertical line, left panel). These optogenetically-induced APs (oAP) were recorded in current-clamp mode (C-clamp) at approximate −85 mV and were detected in most grafted human mGIN examined (n=18 cells, right panel). FIG. 13*d*, Summary plots of resting membrane potential (RMP), membrane resistance (Rm), and a fast component of membrane capacitance (Cm) of grafted human mGIN, which were examined 2, 4, or 5 months after transplantation (n=6, 8, and 11 cells, respectively), as well as host adult hippocampal interneurons (Adult, >3 months old, n=4 cells). *p<0.001, adult versus all other groups. FIG. 13***e*, Representative traces showing currents induced by voltage pulses in a grafted cells. Membrane potential was held at −85 mV in voltage-clamp mode. Left, square voltage pulses from −85 mV to 5 mV with increment of 10 mV (50 ms long) induced both transient inward (Na+, a bracket) and sustained outward currents (K+, a vertical dotted line), which are likely to be mediated by voltage-gated Na+ and K+ channels, respectively. Right, the same trace was zoomed in to visualize the transient inward currents mediated by voltage-gated Na+ channels. FIG. 13*f*, A representative trace of spontaneous AP firings (sAP) in a grafted human mGIN. AP firings were recorded at RMP in current-clamp mode without current injection or withdrawal. A trace on the right is the average of sAP recorded in the same neuron. FIG. 13*g*, Left, spontaneous APs (sAP) were detected at RMP in 45% of total 31 grafted cells examined. Right, a summary graph showing the average frequency of sAP (n=14 cells). Error bars are SEM.

FIG. 14*a*, Left, microscopic images of a recorded human MGE cell in acute hippocampal slices. ChR2/GFP-expressing human MGE cells were identified with green fluorescence and labeled with biocytin-streptavidin (red) using recording pipettes. Right, blue light illumination (470 nm, 0.61 mW/mm2, blue horizontal bar) induces ChR2-mediated currents recorded at −80 mV in voltage-clamp mode, confirming that the recorded cell is a grafted cell. FIG. 14*b*, Analysis of action potential (AP) firings in human mGIN transplanted into the hippocampus. Top, a representative trace of AP firings in a ChR2/GFP-expressing grafted cell. APs were induced by depolarizing current injection near threshold (500 ms long) and recorded in current-clamp mode at approximate −85 mV. The amount of injected currents is indicated below the trace. For each grafted cell, the first AP (an arrowhead) was analyzed. Bottom, summary graphs showing the average AP threshold (left), after hyperpolarization (AHP, middle), and AP half-width (right) in human mGIN examined 2, 4, and 5 months after transplantation (n=6, 8, and 11 cells, respectively) as well as host adult hippocampal interneurons. (Adult, >3 month old, n=4 cells). **p<0.01, adult versus all other groups; *p<0.05, 5 month versus 4 month group; #p<0.05, adult versus 2 or 4 month group. Error bars are SEM. FIG. 14*c*, Representative traces (top row) and phase plots (bottom row) of four different types of AP firings recorded in grafted human mGIN in hippocampal slices. APs were induced by near-threshold depolarizing current injections in GFP+ grafted cells and were recorded as in (b). Most grafted cells displayed either repetitive firings (type A, first column) or single AP firing (type B, second column) while delayed (type C, third column) or burst firing patterns (type D, fourth column) were observed in a small proportion of grafted cells. Repetitive AP firings could be induced by small current injections in type A cells (<50 pA) whereas type B cells fires only a few APs, which required relatively larger current injections (>50 pA). The amount of injected currents is indicated below the traces. Baseline membrane potential was approximately −85 mV. FIG. 14*d*, A summary graph showing the proportion of grafted human MGE-derived cells displaying four different AP firing patterns (n=31 cells). FIG. 14*e*, Left, a summary plot of AP firings in human mGIN in the hippocampus. The number of AP firings was plotted versus injected currents (500 ms long). Note more frequent AP firings induced by small current injections in type A cells (n=16 cells) than in type B cells (n=10 cells). Right, the average membrane resistance (Rm) in type A was larger significantly than in type B cells. p<0.01. Error bars are SEM. FIG. 14***f*, Examples of RNA profiles of three grafted cells from single-cell RT-PCR (scRT-PCR, top three rows). Intracellular contents of grafted cells were harvested individually after whole-cell patch-clamp recordings. Positive control with total RNA from the human brain as well as two negative controls (no RT control and no giga-seal formation) are also included in middle and bottom rows. M, size marker (300, 200 and 100 by from top to bottom); PV, parvalbumin; CR, calreticulin; SST, somatostatin; VIP, vasoactive intestinal peptide; NPY, neuropeptide Y. FIG. 14*g*, A summary plot of RNA profile of grafted human mGIN from scRT-PCR (n=23 cells).

FIG. 15*a*, Blue light illumination induced inward currents, confirming that the recorded cell is a grafted cell expressing ChR2-GFP. ChR2-mediated currents were induced and recorded as in FIG. 14*a*. Confocal microscopic images showed dendrites of the recorded human mGIN Dendritic spines were present along neuron. FIG. 15*b*, Left, a representative trace of postsynaptic responses recorded in a GFP+ grafted cell. Spontaneous excitatory postsynaptic currents (sEPSCs) were recorded in GFP+ grafted cells at −85 mV in voltage-clamp mode. Right, a trace showing the average of sEPSCs recorded in the same cell. Decay time constant (τD) of sEPSC was calculated by fitting the decay phase of the trace to a single exponential function (red curve). FIG. 15*c*, The application of 10 μM NBQX inhibited sEPSC completely in the same grafted cell as in FIG. 15*b*, indicating that sEPSCs were mediated by AMPA/kainate-type glutamate receptors and that the grafted cell receives functional synaptic inputs from host glutamatergic neurons. n=4 cells. FIG. 15*d*, Two thirds of recorded human mGIN displayed spontaneous postsynaptic responses with the frequency >0.1 Hz. Images of the cell bodies of GFP+ grafted cells and GFP-host hippocampal interneurons were obtained. The recorded cells were labeled with biocytin-streptavidin (red). FIG. 15*f*, FIG. 15*g*, FIG. 15*h*, Summary plots of the frequency (FIG. 15*f*), peak amplitude (FIG. 15*g*), and decay time constant (FIG. 15*h*) of sEPSC recorded in GFP+ grafted cells (n=14) and GFP-host hippocampal interneurons (n=10). No significant difference was detected between grafted and host cells (n.s.). Error bars are SEM. Immunohistochemistry analysis of human mGIN transplanted in the hippocampus. Hoechst (sky blue) was used as nuclear counter-stain, postsynaptic densities of GFP+ grafted cells (double-stained with ChR2-GFP and PSD), and presynaptic axon terminals (stained with synaptophysin, green) of GFP-cells were observed. TEM images showed that grafted human mGIN receive synaptic inputs from host cells. Transplanted cells, stained with DAB for human cytoplasm-specific antibodies display prominent postsynaptic densities, receiving inputs from DAB-host cells (no stain) (data not shown).

FIG. 16*a*, Top, blue light illumination evokes AP firings in GFP+ mGIN expressing ChR2 and induces the release of GABA at axon terminals, generating postsynaptic responses in the recorded GFP-host neuron. Bottom left, blue light illumination (0.61 mW/mm2, blue horizontal bar) did not induce ChR2-mediated current in GFP-host neurons at −80 mV in voltage-clamp mode, indicating the lack of ChR2 expression. Bicuculline (30 μM) was added to inhibit GABAergic responses in the recorded host neuron. Bottom right, the comparison of ChR2-currents between grafted and host cells (n=25 and 27 cells, respectively), which received the same blue light illumination (0.61 mW/mm2). *p<0.001. FIG. 16***b*, Left, representative traces of postsynaptic currents recorded in a GFP-host neuron. Postsynaptic responses were recorded at 0 mV in voltage-clamp mode and induced by photostimulations at 12.5 mW/mm2 (1 ms duration, blue vertical line). Blue light illumination was applied every 10 seconds. Right, these postsynaptic currents were completely inhibited by the application of GABAA receptor antagonist, bicuculline (30 μM) in the same neuron. FIG. 16*c*, Left, 44% of total 27 GFP-host neurons displayed GABAA receptor-mediated inhibitory postsynaptic currents (IPSC) induced by photostimulations. Middle, a summary graph showing the average amplitude of IPSCs before and after the application of bicuculline as in (c). p<0.01. Right, a plot showing the average synaptic latency of IPSCs induced optogenetically and recorded in GFP-host neurons (n=10 neurons). The synaptic latency was quantified as the time interval between the start of photostimulations and the onset of synaptic responses. FIG. 16***d*, Left, representative traces of postsynaptic currents recorded in a GFP-host neuron. Postsynaptic currents were induced by blue light illuminations at 12.5 mW/mm2 (1 ms duration, blue vertical line) and recorded in voltage-clamp mode at −80, −60, −40, −20, and 0 mV. Right, a current-voltage plot of the postsynaptic responses. Peak amplitudes of postsynaptic currents were plotted versus holding potential (Vh, closed circles). Linear regression (a dotted line) reveals the reversal potential of the postsynaptic currents (Erev=−70 mV). The application of 30 μM bicuculline inhibited postsynaptic currents completely at all holding potentials examined (open circles). n=3 neurons. FIG. 16*e*, Overlaid traces of quantal IPSCs (qIPSC) indicate both successes (red traces) and failures (black traces). qIPSCs were induced by blue light illuminations (blue vertical line) and recorded in GFP-host neurons as in (d). FIG. 16*f*, Summary plots showing the average potency (quantal size) and release probability (Pr) of qIPSCs. n=6 neurons. FIG. 16*g*, A representative trace of IPSCs induced by train photostimulations. IPSCs were induced by blue light illumination applied at 1 Hz (12.5 mW/mm2, 1 ms duration, blue vertical lines) and recorded in GFP-host neurons at 0 mV in voltage-clamp mode. A trace on the right indicates the last evoked IPSC (a dotted circle). (i) A summary plot of IPSCs during 1 Hz train photostimulations as in FIG. 16*h*. The peak amplitude of IPSCs was normalized to the first IPSC (a dotted line; n=3). Immunohistochemistry analysis of transplanted human mGIN was also done. Hoechst (sky blue) was used as nuclear counterstain. Arrows in magenta indicate GABAergic presynaptic terminals of GFP+ grafted cells (double-stained with ChR2-GFP and VGAT) and inhibitory postsynaptic densities (stained with gephyrin, green) of GFP-cells were observed (data not shown). TEM images of grafted cells stained with DAB for human cytoplasm-specific antibodies were taken. DAB-host cells receives synaptic inputs from DAB+ grafted cells (data not shown).

FIGS. 17*a* to 17*e*. Transplanted mGIN reduce seizure activity and other behavioral abnormalities. FIG. 17*a*, Video-EEG analysis of naïve mice (n=6), vehicle-injected control TLE mice (n=11) and MGE-transplanted TLE mice (n=9). Mean+S.E.M.; p<0.05, ANOVA followed by post hoc analysis using non-parametric Kruskal-Wallis test. Right panel shows representative seizure EEG activity with high-frequency, high-voltage synchronized polyspikes. FIG. 17*b*, Y maze test (Mean±S.E.M.; P<0.05, ANOVA followed by post hoc analysis using Fisher's LSD) of naïve mice (n=9), vehicle-injected TLE control mice (n=10) and transplanted TLE (n=8), shown by % alternation as an indicative of short-term memory and total arm entry as an indicative of locomotor activity. FIG. 17*c*, Novel object recognition test (Mean±S.E.M.; P<0.05, ANOVA followed by post hoc analysis using Fisher's LSD) of naïve mice (n=12), vehicle-injected TLE control mice (n=11) and transplanted TLE mice (n=8), shown by % time near a novel object compared to total time spent exploring objects and % number of visits near novel object among total number of visits exploring objects. Right panel shows representative tracing of mouse center point by Ethovision during trial. FIG. 17*d*, Locomotion test (Mean±S.E.M.; P<0.05, ANOVA followed by post hoc analysis using Fisher's LSD) of naïve mice (n=14), vehicle-injected control TLE mice (n=11) and MGE-transplanted TLE mice (n=8), shown by the number of photobeam breaks in 15 min. FIG. 17*e*, Handling test (Mean+S.E.M.; P<0.05, ANOVA followed by post hoc analysis using Fisher's LSD) of naïve mice (n=15), vehicle-injected TLE control mice (n=11) and transplanted TLE (n=10).

FIG. 18*a*, Representative FACS graph for isolating ENCAM+ cells. Left panel shows secondary antibody only control, and right panel show cells with ENCAM staining Immunocytochemistry analysis of FACS isolated cells was also performed (data not shown). FIG. 18*b*, Cell counting analysis of FACS sorted cells (n=3). Immunohistochemistry at 4 month PT showed that Transplanted human mGIN migrate robustly and integrate in adult epileptic brains (data not shown).

DETAILED DESCRIPTION

Figure 1A:
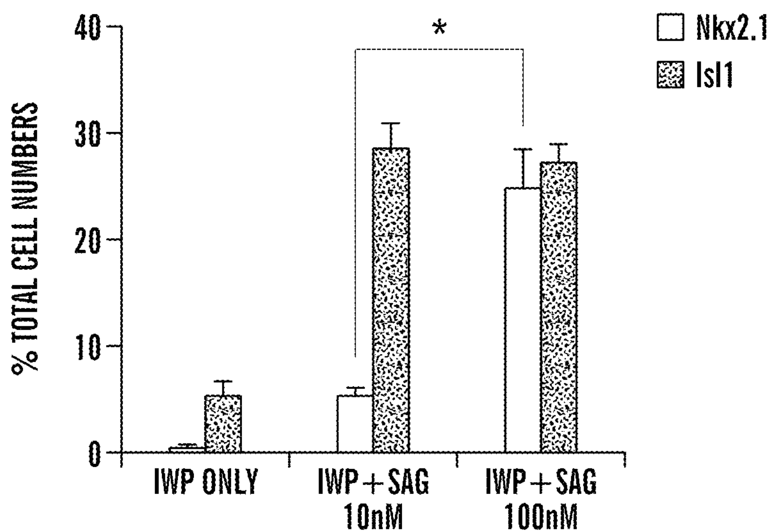
FIGS. 1*a* to 1*c* are graphs showing directed differentiation of human PSCs into ventral telencephalic phenotype.

One aspect of the present invention relates generally to an enhanced method for the production of medial ganglionic eminence (MGE) cells from pluripotent stem cells. The method comprises an additional step of contacting the pluripotent stem cells with an exogenous activator of FGF8 during the differentiation process. We have determined that addition of an exogenous activator of FGF8 generates a higher percentage of MGE cells as compared to in the absence of the activator. We note that less caudal ganglionic eminence (CGE) cells are produced. This highly efficient method for the generation of MGE cells provides a reliable source of MGE cells, or GABAergic interneurons derived therefrom, for therapeutic clinical use and for disease modeling.

Another aspect of the present invention provides methods for suppressing spontaneous seizure activity in a subject. The methods comprise administering MGE cells, which have been derived from pluripotent stem cells, into a subject in need of treatment.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "reprogramming" as used herein refers to a process that alters or reverses the differentiation state of a differentiated cell (e.g. a somatic cell). Reprogramming refers to a process of driving the differentiation of a cell backwards to a more undifferentiated or more primitive type of cell.

The term "induced pluripotent stem cell" or "iPSC" or "iPS cell" refers to a cell derived from reprogramming of the differentiation state of a differentiated cell (e.g. a somatic cell) into a pluripotent cell. An induced pluripotent stem cell a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, T AI60, TRA I81, TDGF 1, Dnmt3b, FoxD3, GDF3, Cyp26al, TERT, and zfp42. IPS cells may be generated by providing the cell with "reprogramming factors", i.e., one or more, e.g., a cocktail, of biologically active factors that act on a cell to alter transcription, thereby reprogramming a cell to pluripotency. Examples of methods of generating and characterizing iPS cells may be found in, for example, Application Nos. US20090047263, US20090068742, US20090191 159, US20090227032, US20090246875, and US20090304646, the disclosures of which are incorporated herein by reference.

The term "pluripotent" or "pluripotent stem cell" as used herein refers to a cell with the capacity, under different conditions, to differentiate to cell types characteristic of all three germ cell layers (endoderm, mesoderm and ectoderm). Pluripotent stem cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell. Pluripotent stem cells can be derived from any organism of interest, including, e.g. human, primate, non-human primate, canine, feline, murine, equine, porcine, avian, bovine etc.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "differentiated cell" is meant any primary cell that is not, in its native form, pluripotent as that term is defined herein. The transition of a differentiated cell to pluripotency requires a reprogramming stimulus beyond the stimuli that lead to partial loss of differentiated character in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process such differentiated cell may be multipotent.

As used herein, the term "somatic cell" refers to any cell other than a germ cell, a cell present in or obtained from a pre-implantation embryo, or a cell resulting from proliferation of such a cell in vitro. Asomatic cell refers to any cells forming the body of an organism, as opposed to germline cells. There are adult somatic cells and embryonic somatic cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein the term "isogenic cell" or "isogenic cells" refers to a cell/s originating from a common source or having the same genetic makeup. For example, when comparing the effect of activator of FGF8 signaling on a population of cells as compared to a population of cells not treated with the FGF8 activator, the isogenic population of cells is derived from the same source as the test population and has been treated the same as the test population, i.e. an "isogenic population of cells", also referred to herein as a control population of cells As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a ectodermal stem cell), which in turn can differentiate into other types of precursor cells further down the pathway (such as an tissue specific precursor, for example, a neuronal cell precursor such a an MGE cell), and then to an end-stage differentiated cell, which plays a characteristic role in a certain tissue type, e.g. a GABAergic interneuron, and may or may not retain the capacity to proliferate further.

The term "embryonic stem (ES) cell" is used to refer to a cell that a) can self-renew, b) can differentiate to produce all types of cells in an organism (pluripotent), and c) is derived from a developing organism or is an established ES cell line which was derived from a developing organism. Embryonic stem cells may be obtained from the inner cell mass of the embryonic blastocyst (see U.S. Pat. Nos. 5,843,780, 6,200, 806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). In culture, ES cells typically grow as flat colonies with large nucleo-cytoplasmic ratios, defined borders and prominent nucleoli. In addition, hES cells express SSEA-3, SSEA-4, TKA-1-60, TRA-1-81, and Alkaline Phosphatase, but not SSEA-1. Examples of methods for identifying and characterizing ES cells may also be found in, for example, U.S. Pat. No. 7,029,913, which is incorporated herein by reference in its entirety.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "exogenous" refers to a substance in addition to the amount of the substance normally present in and secreted from a cell; e.g. exogenous addition of a substance to cell culture medium means the substance was not excreted from the cell. The term "exogenous" when used herein also refers to a nucleic acid (e.g. a nucleic acid encoding a FGF8 transcription factor) or a protein (e.g., FGF8 polypeptide) that has been introduced by a process involving the hand of man into a biological system such as a cell or organism in which it is not normally found or in which it is found in lower amounts. A substance (e.g. a nucleic acid encoding FGF8) will be considered exogenous if it is introduced into a cell or an ancestor of the cell that inherits the substance. In contrast, the term "endogenous" refers to a substance that is native to the biological system or cell.

As used herein, "embryoid body", "embryoid bodies", "EBs" or "EB cells" refers to a morphological, three-dimensional, or organoid-type structure comprised of a population of undifferentiated and differentiated cells which are derived from pluripotent stem cells (e.g., primate pluripotent stem cells (pPS), embryonic stem (ES) ceils, induced pluripotent stem (IPS) cells) that have undergone differentiation. Under culture conditions suitable for EB formation, ES cells proliferate and form small mass of cells that begin to differentiate. In the first phase of differentiation, usually corresponding, to about days 1-4 of differentiation for human cells, the small mass of cells forms a layer of endodermal cells on the outer layer, and is considered a "simple embryoid body." In the second phase, usually corresponding to about days 3-20 post-differentiation for human cells, "complex embryoid bodies" are formed, which are characterized by extensive differentiation of ectodermal and mesodermal cells and derivative tissues. As used herein, the term "embryoid bodies" or "EB" encompasses both simple and complex embryoid bodies unless otherwise required by context. The determination of when embryoid bodies have formed in a culture of ES/iPS cells is routinely made by persons of skill in the art by, for example, visual inspection of the morphology, detection of cell markers. Floating masses of about 20 cells or more (e.g., ES/iPS cells) are considered to be suspension embryoid bodies. (see. e.g., Schmit R., et al, 1991, Genes Dev. 5:728-740; Doetschman, T. C, et al., 1985, J. Embryol. Exp. Morph. 87:27-45). Suspension EBs can be plated onto an adherent substrate to generate adherent EBs.

As used herein, "medial ganglionic eminence (MGE) precursor cell(s)" or "MGE neural precursor cells," refer to a population of mitotic and post-mitotic cells that express the markers expressed by cells in the MGE region of the developing brain. In general MGE precursor cells express markers such as, homeobox gene Nkx2.1, LIM-homeobox genes Lhx6, Lhx7, or Lhx8. MGE precursor cells are capable of differentiating into GABAergic interneurons under suitable differentiation condition.

As used herein, "caudal ganglionic eminence (CGE) precursor cell(s)" or "CGE neural precursor cells," refer to a population of mitotic and post-mitotic cells that express the markers expressed by cells in the CGE region of the developing brain. Such neural progenitor cells are found within CGE domain, a posterior region where the MGE and LGE domains fuse. The CGE precursor cells produce cortical interneurons in the striatum, neocortex and limbic system. In addition, these cells develop into oligodendrocytes that migrate into the cortex. In general CGE precursor cells express markers such as, Dlx1 distal-less homeobox; Dlx2 distal-less homeobox 2; Gsx2 (Gsh2) GS homeobox; Nr2f1 ("COUP-TF1") and COUP TFII nuclear receptor subfamily 2, group F, member 1 and II. CGE precursor cells are capable of differentiating into cortical interneurons under suitable differentiation condition and do not express homeobox gene Nkx2.1.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells.

The term "substantially pure", with respect to a particular cell population, refers to a population of cells that is at least about 75%, at least about 80%, at least about 85%, at least about 90%, or at least about 95% pure, with respect to the cells making up a total cell population. With regard to a population of differentiated MGE cells, refers to a population of cells that contain fewer than about 30%, of CGE cells. In some embodiments, fewer than about 25%, or 20%, or 15%, or 10%, or 8%, or 7%, or 5%, or 1% of CGE cells.

The terms "enriching" or "enriched" are used interchangeably herein and mean that the yield (fraction) of cells of one type is increased by at least 10% over the fraction of cells of that type in the starting culture or preparation.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Examples of cell culture medium include Minimum Essential Medium (MEM), Eagle's Medium, Dulbecco's Modified Eagle Medium (DMEM), Dulbecco's Modified Eagle Medium: Nutrient Mixture F-12 (DMEM F12), FIO Nutrient Mixture, Ham's FIO Nutrient Mix, Ham's F12 Nutrient Mixture, Medium 199, RPMI, RPMI 1640, reduced serum medium, basal medium (BME), DMEM/F12 (1:1), Neurobasal medium, and the like, and combinations thereof. The medium or cell culture medium may be modified by adding one or more factors, such as, supplements, differentiation factors, anti-apoptotic agents.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% as compared to a reference level. The reference level is a control level in the absence of agent/treatment, e.g. with respect to seizures, a decrease in the number of seizures experienced by a subject in the absence of treatment with MGE cells.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. The reference level is a control level in the absence of agent/treatment, e.g. with respect to an increase in MGE cells, there is an increase in the number of MGE cells produced as compared to the absence of treatment with an exogenous factor of FGF8.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. In some embodiments, such markers are proteins, and possess an epitope for antibodies or other binding molecules available in the art, and thus can be monitored by FACs analysis, and immunocytochemistry. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art, including for example, detection of nucleic acid, e.g. mRNA, e.g. by quantitative PCR.

As used herein, the term "ectoderm" is meant the germ layer formed during animal embryogenesis that gives rise to the nervous system, tooth enamel, epidermis, hair, nails, and linings of mucosal tissues.

As used herein the term "Wnts" it is meant the family of highly conserved secreted signaling molecules which play key roles in both embryogenesis and mature tissues. The human Wnt gene family has at least 19 members (Wnt-1, Wnt-2, Wnt-2B/'Wnt-13, Wnt-3, Wnt3a, Wnt-4, Wnt~5A, Wnt-5B, Wnt-6, Wnt-7A, Wnt-7B, Wnt-8A, Wnt-8B, Wnt-9A/Wnt-14, Wnt-9B Wnt-15, Wnt-1OA, Wnt-1 OB, Wnt-11, Wnt-16). Wnt proteins modulate cell activity by binding to Wnt receptor complexes that include a polypeptide from the Frizzled (Fz) family of proteins and a polypeptide of the low-density lipoprotein receptor (LDLR)-related protein (LRP) family of proteins. Once activated by Wnt binding, the Wnt receptor complex will activate one or more intracellular signaling cascades. These include the canonical Wnt signaling pathway: the Wnt planar cell polarity (Wnt PCP) pathway: and the Wnt-calcium (Wnt/Ca2+) pathway.

As used herein, culturing under "non-adherent conditions" it is meant culturing under conditions that suppress the adhesion of cells to the vessel in which they are cultured, e.g., the bottom of a tissue culture plate or flask. In some instances, the cells are naturally non-adherent, i.e., they will not adhere to a surface unless the surface is coated with a matrix composition, e.g., fibronectin, laminin, poly-ornitliin, polylysine, collagen IV, matrigel, and polycarbonate membranes. In some instances, cells may be maintained in a non-adherent state by agitating the culture.

As used herein, culturing under "adherent conditions" it is meant culturing under conditions that promote the adhesion of cells to the container in which they are cultured, e.g. the bottom of a tissue culture plate or flask. In some instances, cells may be induced to adhere to the container simply by keeping the culture stationary. In some instances, the wall of the container to which it is desirable to promote adhesion may be coated with a composition to which the cells may adhere, e.g., fibronectin, laminin, poly-ornithin, poly-lysine, collagen IV, matrigel, and polycarbonate membranes.

The terms "individual", "subject", "host", and "patient" are used interchangeably herein and refer to any mammalian subject for whom diagnosis, treatment, or therapy is desired, particularly humans.

A "variant" polypeptide means a biologically active polypeptide as defined below having at least 70%, 75%, 80%, 85%, 90%, 95%, 98%, or 99% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues: and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, at least about 95%, or at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural polypeptide. In certain embodiments, a variant polypeptide of FGF8 protein is used in methods of the invention.

As used herein, the term "treating" and "treatment" refers to administering to a subject an effective amount of a composition (e.g. comprising MGE cells) so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission, whether detectable or undetectable. The effect may be prophylactic. One of skill in the art realizes that a treatment improves the disease condition, and is not intended to be a complete cure for the disease. The treatment is "effective" if the progression of a disease is reduced or halted.

As used herein, the terms "administering," and "introducing" are used interchangeably in the context of the placement of cells as disclosed herein, by a method or route which results in at least partial localization of the cells at a desired site, surgical or non-surgical administration (e.g. systemic administration). The cells can be administered directly to a tissue of interest, or alternatively be administered by any appropriate route which results in delivery to a desired location in the subject where at least a portion of the cells remain viable. The period of viability of cells after administration to a subject can be as short as a few hours, e. g. twenty-four hours, to a few days, to as long as several years.

The term "transplantation" as used herein refers to surgical introduction of the cells, e.g. transplant to brain, e.g. transplant into the ventral telencephalon.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. For example, reference to a "SHH activator", or "a SMAD inhibitor" includes a plurality of such activators or inhibitors and reference to "the WNT inhibitor" includes reference to one or more WNT inhibitor and equivalents thereof known to those skilled in the art, and so forth, it is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Methods for generating MGE precursor cells from pluripotent stem cells are well known to those of skill in the art and include for example those described by Nicholas C R, et al. Cell Stem Cell, 2013, 12:573-586; Maroof A M, et al. Cell Stem Cell, 2013, 12:559-572; and Liu Y, et al. Nat Biotechnol. 2013, 31:440-447, which are herein incorporated by reference in their entirety. We have identified that adding a step of incubating the differentiating cells with an exogenous activator of FGF8 signaling enhances the number of MGE cells produced by the differentiating cell population.

As used herein, an "activator of FGF8 signaling" refers to a protein, peptide, nucleic acid or compound, that activates signaling normally activated by secreted fibroblast growth factor 8 (FGF8) protein. Fibroblast growth factor 8 is a protein that in humans is encoded by the FGF8 gene (FGF8 fibroblast growth factor 8 (androgen-induced) (Homo sapiens (human) Gene ID: 2253, mRNA NM 001206389; protein NP_001193318). FGF8 protein is important and necessary for setting up and maintaining the midbrain/hindbrain border (or mesencephalon/met-encephalon border) which plays the vital role of "organizer" in development, like the Spemann "organizer" of the gastrulating embryo. FGF8 is expressed in the region where Otx2 and Gbx2 cross inhibit each other and is maintained expression by this interaction. Once expressed, the FGF8 induces other transcription factors to form cross-regulatory loops between cells, thus the border is established. Through development, the FGF8 goes to regulate the growth and differentiation of progenitor cells in this region to produce ultimate structure of midbrain and hindbrain (Harris W A, Sanes D H, Reh T A, 2011, Development of the Nervous System, Third Edition. Boston: Academic Press. pp. 33-34). FGF8 is sufficient to induce the repatterning of midbrain and hindbrain structure (Crossley P H, Martin G R, 1995, The mouse Fgf8 gene encodes a family of polypeptides and is expressed in regions that direct outgrowth and patterning in the developing embryo Development 121 (2): 439-51; See also, Gemel J, Gorry M, Ehrlich G D, MacArthur C A, 1996. Structure and sequence of human FGF8". Genomics 35 (1): 253-7. Xu J, Liu Z, Ornitz D M, 2000, Temporal and spatial gradients of FGF8 and Fgf17 regulate proliferation and differentiation of midline cerebellar structures Development 127 (9): 1833-43).

In one embodiment, the exogenous activator of FGF8 signaling is exogenous FGF8 protein (SEQ ID NO: 1), or variant, or functional fragment thereof.

The FGF8 protein/peptide may be natural or recombinant. In one embodiment, the exogenous activator of FGF8 signaling is a peptidomimetic of exogenous FGF8 protein. FGF8 protein or peptide may be added to the culture (i.e. contacting cells with FGF8) at concentrations ranging from 1-5000 ng/ml, e.g. 10-1000 ng/ml, or 100-1,000 ng/ml.

In one embodiment, the activator of FGF8 signaling is present in the culture medium at a concentration of 10 ng/ml, 100 ng/ml. 200 ng/ml, 300 ng/ml, 400 ng/ml, 500 ng/ml, 1 ug/ml, 1.5 μg/ml, 2 μg/ml, 2.5 μg/ml, or 5 μg/ml.

The activator of FGF8 signaling may be added any time throughout the differentiation process. In one embodiment the activator of FGF8 signaling is added concurrently with the SHH activator. In one embodiment the activator of FGF8 signaling is added after the SHH activator. In one embodiment, the activator of FGF8 signaling is added within days or within weeks after contacting the cells with the SHH activator (e.g. within 1 day up to 20 days). In one embodiment, the activator of FGF8 signaling is added about 1 week after the addition of the SHH activator. After addition, the activator of FGF8 signaling is typically present through to the completion of the differentiation of the cells to cells that express MGE cell markers, which occurs typically in about three weeks.

Pluripotent stem cells suitable for use in the present invention include, for example, the human embryonic stem cell line H9 (NIH code: WA09), the human embryonic stem cell line Hl (NIH code: WAO1), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FoxD3, Connexin43, Connexin45, Oct4, Sox2, Nanog, hTERT, UTF-I, ZFP42, SSEA-3, SSEA-4, Tral-60, Tral-81. Methods for the isolation of pluripotent stem cells from tissues based on marker analysis are well known to those of skill in the art, e.g. non-embryonic pluripotent stem cells can be isolated from the blood as described in for example, WO 2012/106367, and US 2011/0044961.

In some embodiments, the population of pluripotent stem cells is a population of induced pluripotent stem cells (iPSCs) that are produced by reprogramming of somatic cells. In some embodiments, the somatic cell is a human cell. In some embodiments, a somatic cells are diseased somatic cells, for example when producing GABAergic neurons to study disease, e.g., cells obtained from a subject with a pathology, or from a subject with a genetic predisposition to have, or be at risk of a disease or disorder. One can use any method for reprogramming a somatic cell, methods of which are well known in the art, for example, as disclosed in international patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; US7615374; U.S. patent application Ser. No. 12/595,041, EP2145000, CA2683056, AU8236629, 12/602,184, EP2164951, CA2688539, US2010/0105100; US2009/0324559, US2009/0304646, US2009/0299763, US2009/0191159, the contents of each are incorporated herein in their entirety by reference. The iPSCs may be produced by viral-induction or chemical induction e.g., as disclosed in EP1970446, US2009/0047263, US2009/0068742, and 2009/0227032, which are incorporated herein in their entirety by reference.

PSCs can be propagated continuously in culture, using culture conditions that promote proliferation without promoting differentiation. Exemplary stem cell medium is made with 80% DMEM (such as Knockout DMEM "KG DMEM"), 20% of either defined fetal bovine serum (FBS, Hyclone) or serum replacement (e.g., knockout serum replacement (SR)), 1% non-essential amino acids (NEAA), 1% pen-strep-glutamine (1 mM L-glutamine), 0.0008% β-mercaptoethanol, and IQ ng/ml FGF-basic (bFGF). Such medium can also be used in the differentiation protocols as the medium base to add differentiation factors to, e.g. SMAD inhibitor, wnt inhibitor, exogenous FGF8.

The PSCs can be expanded in the undifferentiated state by culturing in an environment that inhibits differentiation. Traditionally, PSCs are cultured on a layer of feeder cells derived from embryonic or fetal tissue of the mouse. Culture plates are plated with 375,000 irradiated mouse embryonic fibroblasts (MEFs) per well (irradiated to inhibit proliferation but permit synthesis of factors that support pPS cells), and used 5 h to 10 days after plating. In certain embodiments, human feeder cells may also be used.

In some embodiments, the PSCs cells are maintained in an undifferentiated state without feeder cells. The environment for feeder-free cultures includes a suitable culture substrate, particularly an extracellular matrix such as Matrigel® or laminin. The PSCs are plated at 15,000 cells $cm^2$ (optimally 90,000 $cm^2$ to 170,000 $cm^2$). Feeder-free cultures are supported by a nutrient medium containing factors that support proliferation of the cells without differentiation. Such factors may be introduced into the medium by culturing the medium with cells secreting such factors, such as irradiated (−4,000 tad) primary mouse embryonic fibroblasts, telomerized mouse fibroblasts, or human feeder cells derived from pPS cells. Medium can be conditioned by plating the feeders at a density of ~5-6×104 $cm^2$ in a serum free medium such as KO DMEM supplemented with 20% serum replacement and 4 to 8 ng/mL bFGF. Medium that has been conditioned for 1-2 days is supplemented with further bFGF, and used to support PSC culture for 1-2 days. Features of the feeder-free culture method are further discussed in International Patent Publications WO99/20741 & WO01/51616; and Xu et al, Nat. Biotechnol., 2001, 19:971 which are herein incorporated by reference.

For differentiation into MGE cells, the PSCs may be cultured in suspension as embryoid bodies, or as adherent culture of embryoid bodies in serum free media.

In one embodiment, the PSCs are grown in low adherent flasks in serum free media thereby allowing for the suspension embryoid bodies to form. The cells may be cultured in the presence of neural inducing supplements, such as B27 or NS21, or SMAD inhibitors.

In one embodiment, the cells are cultured in suspension for a period of at least 1 hr, 3 hrs, 6 hrs, 12 hrs, 18 hrs, 24 hrs, 36 hrs, 48 hrs, 2 days, 3 days, or more, before the neural inducing agent (e.g. SMAD inhibitor) and activator of SHH supplement are added to the culture medium.

In one embodiment the PSCs are grown in low adherent flasks for formation of suspension embryoid bodies. After formation of embryoid bodies the cells are cultured for about two weeks (day 0 to day 14) in the presence of a neural inducing SMAD inhibitor to generate a population of cells that express the neuroectoderm marker Pax6 (Pax6+ cells). An anti-apoptotic agent can optionally be added to the culture, e.g. a ROCK inhibitor. In some embodiments, an inhibitor of WNT is also added to the culture.

In embodiments of the invention, an activator of sonic hedgehog (SHH) is added to the culture early (e.g. at day 0 or within about 5 days) to generate cells that express the ventral telencephalic marker FoxG1. The SHH activator may be present throughout the differentiation process.

In one embodiment, after about a week in culture with the neural inducer (e.g. SMAD inhibitor, and SHH activator) the cells are contacted with an activator of FGF8 signaling, e.g. exogenously added FGF8 protein, for a period of about 1 weeks before transferring the cells to an adherent culture, e.g. grown on polyornithine and fibronectin) still in the presence of exogenous FGF8, and allowed to continue their differentiation for a total of about 3 weeks in culture (day 0 to day 21) in order to generate a population of cells with an enhanced number of MGE cells as compared to isogenic cultures that were not contacted with an exogenous activator of FGF8 signaling, e.g. FGF8.

In certain embodiments, the cells are further differentiated into GABAergic interneurons that express Sox6 by placement in a differentiation media containing GDNF, BDNF, and DAPT (Nicholas, et al., 2013, Cell Stem Cell, 12:573-586).

Example Rho-associated protein kinase (ROCK) inhibitors include, but are not limited to, Y27632, HA-100, H-1152, (+)-trans-4-(1-aminoethyl)-1-(pyridin-4-ylaminocarbonyl) cyclohexane dihydro-chloride monohydrate (described in WO0007835 L WO00057913), imidazopyridine derivatives (described in U.S. Pat. No. 7,348,339), substituted pyrimidine and pyridine derivatives (described in U.S. Pat. No. 6,943,172) and substituted isoquinoline-sulfonyl compounds (described in EP00187371), or GSK429286A, or Thiazovivin, or an analog or derivative thereof. The anti-apoptotic agent may be present at a concentration of at least about 0.1 uM, at least about 0.3 uM, at least about 0.5 uM, at least about 1.0 uM, at least about 1.3 uM, at least about 1.5 uM, at least about 2.0 uM, at least about 2.3 uM, at least about 2.5 uM, at least about 3 uM, at least about 3.5 uM, at least about 4 uM, at least about 4.5 uM, at least about 5.0 uM, at least about 5.5 uM, at least about 6 uM, at least about at least about 7.5 uM, at least about 8.5 uM, at least about 10 uM, at least about 15 uM, at least about 20 uM, at least about 30 uM, at least about 40 uM, at least about 50, uM, at least about 60 uM.

In some embodiments, the inhibitor of SMAD may be present at a concentration of at least about 0.001 uM, at least about 0.003 uM, at least about 0.005 uM, at least about 0.01 uM, at least about 0.05 uM, at least about 0.1 uM, at least about 0.2 uM, at least about 0.3 uM, at least about 0.5 uM, at least about 1 uM, at least about 1.5 uM, at least about 3 uM, at least about 4 uM, at least about 5.0 uM, at least about 6 uM, at least about 7.5 uM, at least about 8.5 uM, at least about 10 uM, at least about 15 uM, at least about 20 uM, at least about 30 uM, at least about 40 uM, at least about 50, uM, at least about 60 uM.

In certain embodiments, the inhibitor of SMAD is an inhibitor of TGF-β signaling. For example, the SMAD inhibitor may be an ALK inhibitor, or antibody or a fragment thereof that binds to a TGF-β receptor. In some embodiments, the inhibitor of TGF-β signaling is a small molecule inhibitor, e.g. the inhibitor of TGF-β signaling may be LY364947 (SD208), SM16, SB-505124, ALK5 Inhibitor II, SB-431542, LY2157299, LDN-193189, A83-Q1, (+)-ITD-1, ITD-1 (ethyl 4-([1,1'-biphenyl]-4-yl)-2,7,7-trimethyl-5-oxo-1,4,5,6,7,8-hexahydroquinoline-3-carboxylate), or ITDts.

In one embodiment, the SMAD inhibitor is BMPRIA-Fc, Noggin, or derivatives thereof.

In one embodiment, the SMAD inhibitor is an inhibitor of a bone morphogenic proteins (BMP) pathway, such as, dorsomorphin. Signal transduction through BMP receptors results in mobilization of the SMAD family members. Inhibitors of BMP signaling can readily be identified by one of ordinary skill in the art by competitive binding assays to the BMP receptors, or by measuring relocalization of SMAD.

In one embodiment, the SMAD inhibitor is an Activin inhibitor, Nodal inhibitor, or GDF signaling pathway inhibitor. Exemplary activin inhibitors include SB431542, Follistatin, A8301, DMH1, Dorsomorphin, K02288, and SB505124. In certain cases, inhibitors of Nodal, such as, SB431542, Lefty, or Cerebrus may be used. In certain cases, SB431542, D4476, GW788388, LY364947, RepSox, SB525334, SD208 may be used to inhibit GDF signaling pathway.

In certain embodiments, two or more SMAD inhibitors may be included in the cell culture medium.

In embodiments of the methods described herein, an activator of sonic hedgehog signaling is present in the medium for culturing cells in order to induce cells that express Dlx1 or Dlx2. In one embodiment, the cells exposed to sonic the hedgehog activator express FoxG1. The activator of sonic hedgehog signaling may be present at a concentration of at least, about 0.001 uM, at least about 0.003 uM, at least about 0.005 uM, at least about 0.01 uM, at least about 0.05 uM, at least about 0.1 uM, at least about 0.2 uM, at least about 0.3 uM, at least about 0.5 uM, at least about 1 uM, at least about 1.5 uM, at least about 3 uM, at least about 4 uM, at least about 5.0 uM, at least about 6 uM, at least about 7.5 uM, at least about 8.5 uM, at least about 10 uM, at least about 15 uM, at least about 20 uM, at least about 30 uM, at least about 40 uM, at least about 50, uM, at least about 60 uM, 1 mM, 2, mM, 3 mM.

Antibodies for ventral telencephalic marker Dlx1 or Dlx2 are commercially available, e.g. Dlx-2a antibody WQ6 is a mouse monoclonal IgG2a provided at 100 μg/ml; raised against recombinant Dlx-2 of human origin available from Santa Cruz Biotechnology (SCBT), CA (Magdalena A. Petryniak et al. Neuron. Aug. 2, 2007; 55(3): 417-433; and Melo et al. Journal of Comparative Neurology, Dlx1, Dlx2, Pax6, Brn3b, and Chx10 homeobox gene expression defines the retinal ganglion and inner nuclear layers of the developing and adult mouse retina 2003, 461(2): 187-204, 23).

The activator of sonic hedgehog (SHH) signaling may be SHH, or a derivative thereof. In certain embodiments, the activator of sonic hedgehog signaling is a small molecule, such as, pumorphamine, SAG smoothened agonist, Hh-Agl.5, or derivatives and analogs thereof.

In one embodiment the SHH activator is added within 2, days, 3 days, 4 days, 5 days, or 7 days after initiation of the differentiation protocol with the SMAD inhibitor.

In certain embodiments of the methods described herein, an inhibitor of Wnt signaling may be present in the medium for culturing cells. Wnt inhibitors are agents that downregulate expression or activity of wnt. Agents of interest may interact directly with, wnt, e.g. drugs, i.e., small molecules, blocking antibodies, etc., or may interact with wnt associated proteins, e.g. Wnt co-receptors LRP5/6 and the transmembrane protein xemen. A number of wnt inhibitors have been described and are known in the art. Wnt inhibitors of interest interfere with the interaction between soluble, extracellular Wnt proteins, and the frizzled receptors that are present on the surface of normal cells. Such agents include, without limitation, soluble frizzled polypeptides comprising the wnt binding domains: soluble frizzled related polypeptides; wnt specific antibodies; frizzled specific antibodies: and other molecules capable of blocking extracellular wnt signaling.

Among the known wnt inhibitors are members of the Dickkopf (Dkk) gene family (see Krupnik et al. Gene, 1999, 238(2):301-13), Members of the human DU gene family include Dkk-1, Dkk-2, Dkk-3, and Dkk-4, and the Dkk-3 related protein Soggy (Sgy). Other inhibitors of wnt include Wise (Itasaki et al Development, 2003,130(18):4295-30), which is a secreted protein. The Wise protein physically interacts with the Wnt co-receptor, lipoprotein receptor-related protein 6 (LRP6), and is able to compete with WntS for binding to LRP6, inhibitors may also include derivatives, variants, and biologically active fragments of native inhibitors. In certain embodiments, the Wnt inhibitor may be a small molecule such as, C I-7, IWP analogs, IWR analogs, XAV939, 53AH, Wnt-059, IWP2, and IWP4, XAV939, ICG001, IWR-1-endo, Wnt-059, LGK-974, FH535, WIKI4, and IWP-L.

In certain embodiments, the Wnt inhibitor is present in the culture medium at a concentration of 10 ng/ml, 200 ng/ml, 300 ng/ml, 400 ng/ml, 500 ng/ml, 1 ug/ml, 1.5 ug/ml, 2 ug/ml, 2.5 ug/ml, or 5 μg/ml for example, at a concentration of 500 ng/ml.

In one exemplary embodiment, in a 3 week human PSC differentiation culture, SMAD inhibitor LDN193189 is present in the PSC culture at 100 nM form day 0 to day 14 and SMAD inhibitor SB431542 is present in the culture at concentration of 10 micromolar from day 0 to day 7 to induce cells that express Pax6; cells are also treated with the Wnt inhibitor IWP2 at 5 micromolar from day 0 to day 7 and with SHH activator SAG at 0.1 um from day 0 to day 21 to induce cells that express ventral telencephalic neuroectoderm marker FoxG1. The cultured cells are further treated with exogenous FGF8 protein, an activator of FGF8 signaling, at 100 ng/ml from day 8 to day 21. The culture is grown as suspension embryoid bodies from day 0 to day 14 prior to being transferred to an adherent embryoid body culture at day 21 to generate a culture with enhanced number of MGE cells that express the marker Nkx2.1. Those of skill in the art understand that the timing and concentrations may vary and that one of skill in the art can monitor for the expression of the indicated markers at each step in the differentiation protocol to make any necessary adjustments.

The cell populations cultured according to the methods disclosed herein may be monitored to assess changes in the cells imparted by culturing (e.g., during one or more time points in the culture method disclosed herein) so as to characterize the cell population produced. For example, the production of Pax6 positive, FoxG1 positive, and Nkx2,1 positive cells. The expression of certain markers can be determined by detecting the presence or absence of the marker transcript or protein expression. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR. (Q-PCR). Methods of performing Q-PCR are well known in the art.

Other methods which are known in the art can also be used to quantitate marker gene expression. For example, the expression of a marker gene product can be detected by using antibodies specific for the marker gene product of interest by e.g. FACS analysis or immunocytochemistry. In certain processes, the expression of marker genes characteristic of the cell population of interest as well as the lack of significant expression of marker genes characteristic of pluripotent stem cells and other cell types may be determined (e.g. CGE cells, COUPII).

Generation of MGE precursor cells may be determined by monitoring expression of Nkx2.1 and Olig 2 gene. As such, the MGE precursor cells produced by the processes described herein express the Nkx2.1 marker gene, thereby producing the Nkx2.1 gene product. The MGE precursor cells produced by the methods described herein may express FoxG1 and do not express PAX6. In some embodiments the MGE cells do not express FoxG1.

In some embodiments, the monitoring of generation of MGE precursor cells may be carried out by performing functional analysis of the cells of interest. For example, MGE precursor cells generated by the methods described herein can further differentiate into GABAergic interneurons in vivo or in vitro that express the markers Lhx6 and Sox6, and that for example express GABA, somatostatin, or parvalbumin.

In some embodiments, the population of MGE cells is further enriched, isolated and/or purified, e.g. by using an affinity tag (e.g. anti-ENCAM antibody) and FACS sorting.

In some embodiments the population of MGE cells are further enriched by screening for and isolating the MGE precursor cells, e.g. by isolating MGE precursor cells using Nkx2.1-specific molecular beacon live cell mRNA probes (See Bao et al., Fluorescent probes for live-cell RNA detection, Annu Rev. Biomed. Engin. 2009, 11: 25-47; and Ricardo and Vaca J. *Nucleic acids* vol. 2011: Article ID 741723: 1-15), and Fluorescence-activated cell sorting (FACS) analysis. Example molecular beacon probe sequences that bind to Nkx2.1, include but are not limited to the molecular beacons having the following sequences: CGCGATCAAACCCATTTGAATCACCAAAGATCGCG (SEQ ID NO: 34); CGCGATCGGCCAGGTTGTTAAGAAGATCGCG (SEQ ID NO 35); CGCGATCGAAGCGGTGAGGCAGAGCGGATCGCG (SEQ ID NO 36) CGCGATCCCCGGCGTCCTCTCACGATCGCG (SEQ ID NO 37); CGCGATCATGGTGCCGTAGTCCGAGGATCGCG (SEQ ID NO: 38); CGCGATCCAGACACTGAGAACGGAGTCGATCGCG (SEQ ID NO: 39); CGCGATCGATTCGGCGGCGGCTGGATCGCG (SEQ ID NO: 40); CGCGATCGCCTTCCCACTGCCTCCGGATCGCG (SEQ ID NO 41); and CGCGATCACCACATCGGGCTTCGCTGGATCGCG (SEQ ID NO 42); which correspond to beacons having stem loop structure and sequence that is complimentary to Nkx2.1 mRNA at start positions 1,623; 1,420; 1,348; 1,314; 1,265; 229; 186; 122; 103; respectively, see for e.g. SEQ ID NO: 44).

In one embodiment, the population of MGE cells are differentiated into GABAergic interneurons, and the GABAergic interneurons are further enriched by isolating the GABAergic interneurons using antibody against markers of immature interneurons, e.g. PCPTP1 (Faux, C., et al., Differential gene expression in migrating cortical interneurons during mouse forebrain development. J Comp Neurol, 2010, 518(8): p. 1232-48) or CXCR4 (Meechan et al. PNAS, 2012, 109(45): 18601-08606) followed by FACS analysis. Antibodies against PCPTP1 and CXCR4 are known in the art and are commercially available.

Another aspect of the invention relates to the use of the MGE cells in order to treat neurodegenerative diseases, wherein the MGE cells that have been derived from pluripotent stem cells are derived using an activator of FGF8 signaling, such as FGF8.

In addition, herein we demonstrate, for the first time, that transplantation of MGE cells, derived from pluripotent stem cells, successfully migrate throughout the hippocampus, mature into GABAergic neurons, and integrate into the host neural circuitry allowing receipt of excitatory inputs, and release of GABA, which in turn induces inhibition of spontaneous seizures.

Thus, in still another aspect of the invention methods for suppression of seizure activity in a subject are provided. The methods comprise administering to a subject in need of treatment MGE cells that have been derived from pluripotent stem cells, for example using the methods described herein, wherein the presence of MGE cell in the population is enhanced, e.g. to greater than 80% MGE cells.

In one embodiment, the population of MGE cells used in the transplantation are derived from PSCs without using an activator of FGF8 signaling.

In certain embodiments the MGE cell population is further enriched by screening for and isolating the MGE precursor cells prior administration of the MGE cells for inhibition of seizure activity.

In one embodiment, the population of MGE cells is differentiated into GABAergic interneurons. In certain embodiments, the GABAergic interneurons are further enriched by isolating the GABAergic interneurons prior to administration of the interneurons for inhibition of seizure activity.

Routes of administration suitable for the methods of the invention include local administration. Generally, local administration results in of the cells being delivered to a specific location as compared to the entire body of the subject, whereas, systemic administration results in delivery of the cells to essentially the entire body of the subject. Exemplary modes of administration include, but are not limited to, injection, infusion, instillation, inhalation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. One method of local administration is by intracranial injection.

In the context of administering MGE cells as disclosed herein, the term "administering" includes transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient, e.g. after differentiation into MGE cells), allotransplantation (transplantation between members of the same species), and xenotransplantation (transplantations between members of different species).

Methods for transplanting neuronal grafts in the brain or other localized area are known in the art. See for example, WO2010108665A "Promotion of neuronal integration in neural stem cell grafts. Conventional techniques for grafting are also described in, for example, Bjorklund et al. (Neural Grafting in the Mammalian CNS, eds. Elsevier, 1985, pp 169-178), Leksell et al. (Acta Neurochir., 1980, 52:1-7) and Leksell et al. (J. Neurosurg., 1987, 66:626-629). In certain embodiments, identification and localization of the injection target regions will generally be done using a non-invasive brain imaging technique (e.g., MRI) prior to implantation (see, for example, Leksell et al., J. Neurol. Neurosurg., 1985, Psychiatry, 48:14-18).

In one embodiment the MGE cells are transplanted into the ventral telencephalon of the brain.

In one embodiment, the transplantation therapies involve the intraparenchymal intracerebral grafting of the replacement cell populations into the lesioned region of the nervous system, or at a site adjacent to the site of injury. In one embodiment, the therapeutic cells are delivered to a specific site by stereotaxic injection.

Briefly, administration of cells into selected regions of a patient's brain may be made by drilling a hole and piercing the dura to permit the needle of a microsyringe to be inserted. Alternatively, the cells can be injected into the brain ventricles or intrathecally into a spinal cord region. The cell preparation of the invention permits grafting of the cells to any predetermined site in the brain or spinal cord. It also is possible to effect multiple grafting concurrently, at several sites, using the same cell suspension, as well as mixtures of cells.

Following in vitro cell culture differentiation and optional further isolation as described herein, the cells are prepared for implantation. In one embodiment, the cells are suspended in a compatible carrier, such as cell culture medium (e.g., Eagle's minimal essential media), phosphate buffered saline, Hanks balanced salt solution, or artificial cerebrospinal fluid (aCSF). Those of skill in the art are well versed in determining dose. Cell density is generally about $10^4$ to about $10^7$ cells/μl, and in one embodiment about 25,000 to about 100,000 cells/μl. The volume of cell suspension to be implanted will vary depending on the site of implantation, treatment goal, and cell density in the solution. For example, for treatments in which cells are implanted into the brain parenchyma, about 5-60 μl of cell suspension may be administered in each injection. Several injections may be used in each host, particularly if the lesioned brain region is large. Alternatively, administration via intraventricular injection, for example, will accommodate relatively larger volumes and larger cell numbers (See, for example, Madrazo et al., New Engl. J. Med., 1987, 316:831-834; Penn et al., Neurosurgery, 1988, 22:999-1004).

In some embodiments, the cells are encapsulated within permeable membranes prior to implantation. Encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

For administration to a subject, a population of MGE cells, or differentiated progeny derived from such MGE cells can be provided in any pharmaceutically acceptable composition. These pharmaceutically acceptable compositions comprise a population of cells, formulated together with one or more pharmaceutically acceptable carriers (additives) and/or diluents.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW~200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off ~40-80 kDa).

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

Preferably, the subject is a mammal. Mammals other than humans can be advantageously used as subjects that represent animal models of disorders associated with neural disfunction. In addition, the methods and compositions described herein can be used to treat domesticated animals and/or pets.

In methods of treatment of the invention, a subject can be one who has been previously diagnosed with or identified as suffering from or having a disorder characterized with a disease for which the MGE stem cell based therapy would be useful. Thus in some embodiments, the methods further comprise selecting a subject with a disease that would benefit from a stem cell based therapy, e.g. a subject diagnosed as having a neurological disease or disorder.

As used herein, the term "neurological disease" or "neurological disorder" comprises a disease or a state characterized by a central nervous system (CNS) having abnormal inhibitory neuron signaling, e.g. a lack of neurotransmitter secreted by GABA neurons. Non-limiting examples of such neurological disorders include, e.g. Alzheimer's disease, Parkinson's disease, Huntington's disease, Autism, epilepsy, schizophrenia, and autism.

Methods for the diagnosis of such neurological disorders are well known to those of skill in the art. For example, epilepsy may be diagnosed by details of the patients medical history, blood tests, EEG tests, and brain imaging tests such as CT and MRI scans. An MRI of the brain is considered the standard radiology procedure to see the characteristic abnormalities associated with medial temporal lobe epilepsy. Genetic testing can also be done.

In certain embodiments, the amelioration of symptoms is measured by monitoring a decrease in seizure activity. For example, a patient can be monitored over a given period of time and the frequency of seizures assessed over that defined time period before and after treatment. Suppression of seizure activity may be indicated at a decrease of about 10%, about 30%, about 50%, about 60%, about 70%, about 80%, or more, as compared to frequency observed prior to treatment.

In certain embodiments, the amelioration of symptoms is measured by monitoring for an increase in cognitive ability, e.g. in Alzheimer's disease or Epilepsy. Improved cognitive ability may be indicated at an increase of about 10%, about 30%, about 50%, about 60%, about 70%, about 80%, or more, as compared to cognitive ability observed prior to treatment.

In certain embodiments, the amelioration of symptoms is measured by monitoring for improved motor neuron movement, e.g. in Parkinson's disease, Huntington's disease. Improved motor neuron control may be indicated at an increase in ability to voluntarily control muscle movement by about 10%, about 30%, about 50%, about 60%, about 70%, about 80%, or more, as compared to voluntary movement observed prior to treatment.

In certain embodiments, the amelioration of symptoms is measured by monitoring for decreased anxiety or in hallucinations, e.g. in schizophrenia, a decrease of about 10%, about 30%, about 50%, about 60%, about 70%, about 80%, or more, as compared to frequency observed prior to treatment.

Methods for monitoring seizure disorders are well known in the art and include for example those described in U.S. Pat. No. 8,684,921, which describes methods for detecting, assessing, and managing epilepsy using a multi-variate, metric-based classification analysis, which is herein incorporated by reference in its entirety.

In one aspect of the invention, a method for suppression of spontaneous seizure activity is provided. The method comprises administering to a subject in need MGE cells that are derived from pluripotent stem cells. In one embodiment the subject has epileptic seizures. In one embodiment, the subject is diagnosed as having temporal lobe epilepsy.

Epileptic seizures are characterized by unpredictable abnormal electrical discharge, loss of consciousness and convulsions, and they are experienced by one in 26 individuals at some point in their lifetime (Jensen, 2014 of Example 2 references). One of the most common forms of seizures is temporal lobe epilepsy (TLE), characterized by epileptic abnormalities in the hippocampus, parahippocampal gyrus and amygdala (Engel, 2001 of Example 2 references). About one third of patients with TLE exhibit intractable seizures that cannot be controlled by anti-epileptic drugs (AEDs) (Engel, 2002 of Example 2 references), and surgical resection of the seizure focus may be necessary (Christoph, 2008 of Example 2 references). Patients who are not candidates for surgery must live with ongoing seizures—in many cases, multiple events in a single day. Although AEDs can reduce or eliminate seizures for the more fortunate patients, these medicines are associated with diverse and troublesome side effects, including weight gain, metabolic acidosis, hepatotoxicity, movement disorders, and mental status changes (Cramer et al., 2010 of Example 2 references; Walia et al., 2004 of Example 2 references).

A key pathological feature of human TLE is synaptic reorganization, including neuronal loss and gliosis in CA1 and hilus, granule cell dispersion, and mossy fiber sprouting in the dentate gyrus (Wieser, 2004 of Example 2 references). Examination of excised epileptic tissue from TLE patients has revealed a loss of GABAergic interneurons (de Lanerolle et al., 1989 of Example 2 references; Marco et al., 1996 of Example 2 references; Spreafico et al., 1998 of Example 2 references). It is believed that a decrease in GABA-mediated inhibition is a critical contributing factor in epilepsy.

Using highly efficient methods for generating medial ganglionic eminence (MGE) cells from human PSCs as described herein, we transplanted a homogeneous cell population of human MGE cells into pilocarpine-induced TLE mice, a well-characterized model of human TLE (Curia et al., 2008 of Example 2 references) and extensively characterized the biology of human PSC-derived maturing GABAergic interneurons (mGIN) within the epileptic brain. mGIN actively migrate, spreading throughout the entire host hippocampus. Using optogenetic approaches and ultrastructural studies, we have demonstrated that grafted mGIN integrate into the dysfunctional host circuitry, receive excitatory inputs and, in turn, induce inhibitory responses in host neurons by releasing GABA. This ultimately resulted in the reversal of behavioral abnormalities in TLE mice, including spontaneous seizures as well as comorbid cognitive impairment, hyperactivity, and aggressiveness. Accordingly, administration of pluripotent stem cell derived MGE cells address a desperate need for new therapies for seizure disorders.

In some embodiments of the present invention may be defined in any of the following numbered paragraphs:

Paragraph 1. A method for the generation of a population of medial ganglionic eminence (MGE) cells from pluripotent stem cells comprising the steps of a) contacting a population of pluripotent stem cells with a SMAD inhibitor to generate a population of cells that express the neuroectoderm cell marker Pax6, b) contacting the cells of step a) with an activator of sonic hedgehog (SHH) to generate a population of cells that express ventral telencephalic neuroectoderm marker Dlx1 or Dlx12; and c) contacting the cells of step b) with an activator of FGF8 signaling to produce a population of cells that comprises an increased percentage of MGE cells that express the transcription factor NKX2.1 as compared to cells of step b) that have not been contacted with the FGF8 activator.

Paragraph 2. The method of paragraph 1, wherein population of cells of step b) comprises less than 30% of caudal ganglionic eminence (CGE) cells that express the cell marker, CopuTFII.

Paragraph 3. The method of any of paragraphs 1-2, wherein the MGE cells further express the transcription factor Olig2.

Paragraph 4. The method of any of paragraphs 1-3, wherein the activator of FGF8 signaling is exogenous FGF8 protein, or an exogenous peptidomimetic of FGF8 protein.

Paragraph 5. The method of any of paragraphs 1-4, wherein the MGE cells are capable of differentiating into GABAergic interneurons that express Lhx6 protein and Sox6.

Paragraph 6. The method of any of paragraphs 1-5, wherein the activator of sonic hedgehog is smoothened agonist (SAG).

Paragraph 7. The method of any of paragraphs 1-6, wherein the inhibitor of SMAD comprises LDN193189 and SB431542.

Paragraph 8. the method of any of paragraphs 1-7, wherein the pluripotent stem cells are human cells.

Paragraph 9. The method of any of paragraphs 1-8, wherein the pluripotent stem cells are embryonic stem cells.

Paragraph 10. The method of any of paragraphs 1-9, wherein the pluripotent stem cells are induced pluripotent stem cells.

Paragraph 11. The method of any of paragraphs 1-10, wherein the pluripotent stem cells are cultured as embryoid bodies.

Paragraph 12. The method of any of paragraphs 1-11, wherein the pluripotent stem cells are cultured in suspension.

Paragraph 13. The method of any of paragraphs 1-12, wherein the pluripotent stem cells are cultured as adherent cells.

Paragraph 14. The method of any of paragraphs 1-13, wherein step a) further comprises contacting the population of pluripotent stem cells with an inhibitor of Wnt.

Paragraph 15. The method of any of paragraphs 1-14, further comprising differentiating the population of cells comprising MGE cells into GABAergic interneurons that express the cell marker Lhx6 and Sox6.

Paragraph 16. The method of paragraph 15, wherein the MGE cells are differentiated by culturing the MGE for a time sufficient to allow for the MGE cells to spontaneously differentiate into GABAergic interneurons.

Paragraph 17. The method of any of paragraphs 14-16, wherein the GABAergic interneurons express GABA.

Paragraph 18. The method of any of paragraphs 14-17, wherein the GABAergic interneurons further differentiate to express somatostatin or parvalbumin.

Paragraph 19. An isolated population of cells produced by the method of any of paragraphs 1-18, wherein the isolated population of cells are derived from pluripotent stem cells.

Paragraph 20. A method for treatment of a neurological disorder comprising administering to a subject in need of treatment the isolated population of cells of paragraph 19.

Paragraph 21. The method of paragraph 20, wherein the subject in need of treatment is diagnosed as having seizures.

Paragraph 22. The method of paragraph 21, wherein the subject is diagnosed as having a neurological disorder selected from the group consisting of Alzheimer's disease, Parkinson's disease, Huntington's disease, neuropathic pain, epilepsy, autism, and schizophrenia, Paragraph 23. The method of any of paragraphs 19-22, wherein the pluripotent stem cells are allogenic cells.

Paragraph 24. The method of any of paragraphs 19-23, wherein the cells are administered by transplantation.

Paragraph 25. A method for suppression of spontaneous seizure activity in a subject comprising administering MGE cells derived from pluripotent stem cells into a subject in need of treatment.

Paragraph 26. The method paragraph 25, wherein the subject is diagnosed as having epilepsy.

Paragraph 27. The method of any of paragraphs 25-26, wherein the MGE cells are derived from human pluripotent stem cells.

Paragraph 28. The method of any of paragraphs 25-27, wherein the MGE cells are derived from induced pluripotent stem cells.

Paragraph 29. The method of any of paragraphs 25-27, wherein the MGE cells are derived from embryonic pluripotent stem cells.

Paragraph 30. The method of any of paragraphs 25-29, wherein the pluripotent stem cells are allogenic cells.

Paragraph 31. The method of paragraph 25, wherein the MGE cells are obtained by the method any of the claims 1-14.

Paragraph 32. The method of any of paragraphs 25-31, wherein the MGE cells are further differentiated into GABAergic interneurons that express Lhx6 and Sox6 prior to administration to the subject.

Paragraph 33. The method of any of paragraphs 1-32, wherein the cells are administered by transplantation.

Paragraph 34. The method of any of paragraphs 1-33, wherein either the MGE cells or interneurons are further isolated from the population by a selection procedure.

Paragraph 35. The method of any of paragraphs 1-33, wherein the MGE cells in the population are further enriched by purification.

Paragraph 36. The method of paragraph 34, wherein the MGE cells are purified using a molecular probe against NKx2.1.

Paragraph 37. The method of paragraph 36, wherein the molecular probe is has a nucleotide sequence selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41; and SEQ ID NO: 42.

Paragraph 38. The method of any of paragraphs 1-33, wherein the GABAergic interneurons in the population are isolated using an antibody against PCPTP1 or CXCR4 and FACS analysis.

Paragraph 39: A Method for the isolation of MGE cells from a population of cells wherein the method comprises contacting the cells with a Nkx2.1 specific molecular beacon that binds to live cell mRNA and isolating cells that bind the molecular beacon.

Paragraph 40. A Method for the isolation of GABAergic interneurons from a population of cells wherein the method comprises contacting the cells with an antibody against PCPTP1 or CXCR4, and isolating the cells that bind the antibody, eg. by using FACS analysis.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Example 1

Here we show that SHH activation during early human neural development elicits a pleiotropic downstream cascade, by inducing rostralizing FGF8 signaling as well as caudalizing FGF15/19 signaling, as observed during early mouse development [6, 20-24]. Such dual effect of SHH on rostral-caudal boundary determination can cause MGE derivation stochasticity depending on the fine balance of its downstream cascade. Thus, by combining early activation of SHH with exogenous rostralizing factor FGF8, we reliably induced MGE cells using early and strong SHH activation (>80% by FACS) from multiple hPSCs. These cells shared characteristics with their in vivo counterpart, such as spontaneous differentiation into Lhx6-expressing and migrating GABAergic interneurons that can generate GABA, fire action potentials and form functional GABAergic synaptic connections. Transplantation of human MGE cells into rodent brains yields well-contained neural grafts enriched with GABAergic interneurons that migrate in the host brain and mature to express somatostatin or parvalbumin.

Methods

PSC Culture and Differentiation

Human PSC cells (H9 ESCs (WA09, WiCell, Madison, Wis., passage 45-55), H7 ESC (WA07, WiCell, passage 41-51) and iPSC2497 (a kind gift from Dr. Fred Gage, [14], passage 30-40) were maintained on Matrigel (BD, San Hose, Calif.) in mTeSR media (Invitrogen, Carlsbad, Calif.) with 10 ng/ml bFGF (Peprotech, Rocky Hill, N.J.), and passaged using Dispase (Stem Cell Technologies, Vancouver, BC, Canada). For differentiation, PSCs were trypsinized and grown as floating aggregates in low adherent flasks in KSR media (20% knockout serum replacement, DMEM, 2 mM L-glutamine and 10 μM β-mercaptoethanol (all from Invitrogen)). Rock inhibitor (Y-27632, 10 μM, Tocris, Bristol, United Kingdom) was added on the first day of differentiation. After two weeks of floating culture, cells were transferred to polyornithine (PLO; 15 mg/ml; Sigma, St. Louis, Mo.) and fibronectin (FN; 1 mg/ml; Sigma, St. Louis, Mo.) coated surfaces. For neural induction, cells were treated with LDN193189 (100 nM, Stemgent, Cambridge, Mass.) from d0 to d14 and with SB431542 (10 μM, Tocris) from d0 to d7 [25]. For MGE induction, cells were treated with IWP2 (5 μM, EMD Millipore) from d0 to d7, with SAG (0.1 □□M, EMD Millipore) from d0 to d21, and with FGF8 (100 ng/ml, Peprotech) from d8 to d21. After 3 weeks of differentiation, cells were trypsinized and droplets of 10,000 cells/μl transferred to PLO/FN-coated coverslips in differentiation media (N3 media [26] with 10 ng/ml GDNF (Peprotech), 10 ng/ml BDNF (Peprotech) and 2.5 μM DAPT (Tocris)) for further differentiation and maturation.

For Matrigel two dimensional migration analysis, MGE cells or control cells (Pax6+ cells without IWP2, SAG and FGF8 treatment) were trypsinized at day 21 of differentiation and reaggregated in low attachment round bottom 96 well plate in differentiation media (10,000 cells per well). MGE spheres or cortical spheres were plated on coverslips coated with 1:100 diluted Matrigel in differentiation media after 25 days of further differentiation and analyzed 5 days after plating. For analysis of migrating cell numbers, total cell numbers that migrated out of the spheres were counted, and then the cells were trypsinized to count the total cell numbers for normalization. For measuring migration distances, ImageJ software was used to assess each cell migration distance between the edge of the sphere and the center of the migrating cell body. Some of the spheres were also fixed for immunocytochemistry analysis.

For Matrigel two dimensional migration analysis of mouse explant, E13.5 embryos were removed one at a time from anesthetized CD1 dams, brains were isolated, embedded in 8% low gelling temperature agarose (Sigma) and cut at a thickness of 300 μm on a vibratome in the coronal plane. Both cortical and medial ganglionic eminence (MGE) regions were punched out from these coronal sections using a micro-punch (Guide wire and tube assembly, 19 gauge; Inner Diameter 0.027", Small Parts Inc. Miami Lakes, Fla.) and collected in Neurobasal medium. E13.5 cortex or MGE explants were plated on coverslips coated with 1:100 diluted Matrigel, and analyzed the same way as the human spheres.

For Matrigel three dimensional migration analysis, MGE explants or human MGE spheres were embedded in undiluted 3D matrigel matrix, cultured in differentiation media and their migration was analyzed 2 days after embedding.

Slice Transplantation Analysis

E13.5 embryos were collected by hysterotomy of deeply anesthetized CD1 dams (Ketamine, 50 mg/kg and Xylazine, 10 mg/kg; i.p.) and decapitated immediately. Embryonic brains were isolated and embedded in 8% low gelling temperature agarose (Sigma). Coronal slices (250-300 μm thick) of telencephalon were prepared and transferred to polycarbonate membrane filters (Invitrogen) in sterile six well plates containing Neurobasal medium (Invitrogen). Control spheres and MGE spheres, that were prepared as described above and pre-labeled with QDot 655 nanocrystals (Invitrogen) according to the manufacturer's instructions (cells incubated in 10 nM labeling solution at 37° C. for an hour), were inserted using fine tungsten needles into the ventral telencephalon of CD1 slices under a high power stereomicroscope. Slices were cultured for 48 hours, fixed in zinc fixative (BD Pharmingen) and processed for paraffin wax histology. NCAM immunohistochemistry was performed on 20 μm thick paraffin sections with a mouse monoclonal anti-NCAM antibody raised against CD56 positive cells of human origin (SantaCruz) and mounted with DAPI (Vector Laboratories). Other antibodies used were mouse anti-human cytoplasm antibody (Stem Cell Inc.) and cy3-conjugated anti-human Nuclei antibody (Millipore). Images were captured from an FSX100 microscope (Olympus The number of NCAM+ cells that migrated from ventral to dorsal telencephalon in the three panels depicted in the schema was determined by ImageJ software and average values obtained. Statistical significance of differences between groups was analyzed by two-tailed Student's t-test (Prism6; GraphPad software). Results were expressed as mean±SD and statistical significance was reported at $P<0.05$.

FACS Analysis

Differentiated cells were trypsinized and fixed in Fix/Perm solution (BD) for 30 min., and incubated with blocking buffer (PBS with 0.1 mg/ml BSA and 0.1% Saponin (both from Sigma, St. Louis, Mo.)) for 10 minutes. Blocked cells were incubated with primary antibody (anti-Nkx2.1; Epitomics) in blocking buffer for 30 minutes. After washing with PBS, Alexa 647-conjugated secondary antibodies (Invitrogen) were added (1:1000) and incubated for another 15 minutes. Some samples were incubated only with secondary antibody as control. After washing with PBS, cells were suspended in blocking buffer and analyzed using a FACSAria (BD Biosciences, San Jose, Calif.). Flowjo (Tree Star, Ashland, Oreg.) software was used to analyze raw data. Ten thousand cells were used per analysis.

Real Time PCR Analysis

Total RNA was prepared using Trizol (Invitrogen) and Purelink RNA mini kit (Invitrogen). cDNA from total RNA was generated using the SuperScript™ II RT (Invitrogen, Carlsbad, Calif.) and oligo (dT) primers. For quantitative analysis of the expression level of mRNAs, real-time PCR analyses were performed using the DNA engine Opticon™ (MJ Research, Waltham, Mass.) and SYBR green I (Molecular Probes, Oreg.). Primers were designed using the MacVector software (Oxford Molecular Ltd.: primers sequences are available upon request). PCR were performed in 25 μl containing 0.5 mM of each primer, 0.5×SYBR Green I (Molecular Probes), and 1 μl of cDNA. Fifty cycles consisting of 95° C. for 30 sec., 55° C. for 30 sec., 72° C. for 30 sec., and 79° C. for 5 sec. were performed. Primer dimers were melted at 79° C. before measuring the fluorescent signals after each cycle. The mRNA expression level for each gene was normalized against that of the GAPDH gene. The relative values were calculated by setting the normalized value of control as 1.

Immunocytochemistry & Immunohistochemistry

For immunofluorescence staining, fixed cells or tissue sections were incubated with blocking buffer (PBS, 10% normal donkey serum (NDS)) containing 0.1% Triton for 10 minutes. Cells were then incubated overnight at 4° C. with primary antibodies diluted in PBS containing 2% NDS. The primary antibody list can be found in table 1. After rinsing with PBS, samples were incubated with fluorescent dye-labeled secondary antibodies (Alexa 488-Alexa 594- or Alexa 647-labeled IgG; Invitrogen, Carlsbad, Calif.) in PBS containing 2% NDS for 30 minutes at room temperature. After rinsing with PBS, Hoechst 33342 (4 mg/ml) was used for counterstaining, and coverslips/tissues sections were mounted onto slides in Mowiol 4-88 (Calbiochem, Gibbstown, N.J.). Confocal analysis was performed using an Olympus DSU Spinning Disc Confocal on an IX81 inverted microscope (Center Valley, Pa.).

Cell Counting and Statistical Analysis

Cells were counted using the StereoInvestigator image capture equipment and software (Microbright Field, Williston, Vt.). For counting of cells on cover slips, an optical fractionator probe was used with a 500 μm×500 □m grid size and 100 μm×100 mm counting frame (>40 counting sites with >1000 total cells counted per sample) at 40× magnification. Coverslips from 3-4 independent differentiations were used for analysis. For statistical analysis, we performed t-test (alpha=0.05) comparing control vs. sample using Prism6 software (Graph Pad).

HPLC Assay

Cellular GABA content was measured by HPLC from MGE cells and cortical cells as control after 60 days of differentiation, as described previously [26]. Cells were homogenized, using a tissue dismembrator, in 100-750 μl of 0.1M TCA supplemented with 10-2 M sodium acetate, 10-4 M EDTA, 5 ng/ml isoproterenol (as internal standard) and 10.5% methanol (pH 3.8). Samples were spun in a microcentrifuge at 10000× g for 20 minutes. Supernatants were collected and analyzed by HPLC while protein determination was performed on the pellets for normalization of the HPLC data. Amino Acids were determined by the Waters AccQ-Tag system utilizing a Waters 474 Scanning Fluorescence Detector. The Empower 2 software was used to control the HPLC gradient profile and data acquisition.

Electrophysiological Analysis

MGE cells were differentiated for 6 or 12 weeks in differentiation media and transferred into a recording chamber that was continuously perfused with artificial cerebrospinal fluid containing 130 mM NaCl, 2.5 mM KCl, 2.5 mM CaCl2, 1 mM MgSO4, 1.25 mM NaH2PO4, 26 mM NaHCO3, and 10 mM glucose with 95% O2 and 5% CO2 at a rate of 1 mL per minute at room temperature (21-23° C.). Whole-cell patch clamp recordings were performed at 24-25° C. using an EPC-9 amplifier and Pulse v8.8 software (HEKA Elektronik). The patch electrodes (2-3 M□ resistance) were filled with a solution of 140 mM KCl, 5 mM NaCl, 1 mM MgCl2, 10 mM HEPES, 0.2 mM EGTA, 2 mM Mg ATP, and 0.5 mM Na GTP (285 mOsm, adjusted to pH 7.3 with KOH). Liquid junction potential of 3.1 mV was not corrected. Series resistance was compensated at 50-60%. Offline data analysis was performed using the Clampfit 9 program (Molecular Devices). Reagents were purchased from Tocris Bioscience (tetrodotoxin) or Sigma-Aldrich (bicuculline methochloride).

Transplantation Analyses

The Animal Care and Use Committee at McLean Hospital approved all animal procedures. H9-derived MGE cells at 5 weeks of differentiation were trypsinized and suspended to a final concentration of 50,000 cells/μl in transplantation media (HBSS with 10 ng/ml GDNF, 10 ng/ml BDNF and 20 μM Boc-Asp(OMe) fluoromethyl ketone (BAF; Sigma-Aldrich)). One μl was injected into each striatum of NOD SCID mice (from the bregma: AP +0.05, L +0.18, V −0.30, IB 9) using a 22-gauge, 5 ml Hamilton syringe and a Kopf stereotaxic frame (Kopf Instruments, Tujunga, Calif.). Cortically induced cells without signaling pathway activation were also transplanted as control (n=10). Before surgery, mice received an i.p. injection of acepromazine (3.3 mg/kg, PromAce, Fort Dodge, Iowa) and atropine sulfate (0.2 mg/kg, Phoenix Pharmaceuticals, St. Joseph, Mo.) followed by anesthesia with an i.p. injection of ketamine (60 mg/kg, Fort Dodge) and xylazine (3 mg/kg, Phoenix Pharmaceuticals). Transplanted mice were terminally anesthetized with an i.p. overdose of pentobarbital (150 mg/kg, Sigma) and perfused intracardially with heparin saline (0.1% heparin in saline) followed by formaldehyde (4%) 5 weeks or 5 months post grafting. Brains were removed, postfixed in 4% formaldehyde, equilibrated in 20% sucrose, and 40-mm coronal slices obtained using a freezing microtome. The StereoInvestigator image-capture equipment and software (MicroBrightField) were used for cell counting and estimation of total cell number in the graft using the serial section manager tool from every 6th sections. Total graft volume was also measured using the StereoInvestigator with the Cavalieri estimator probe and serial section manager tool from every 6th sections.

Results

MGE Cell Specification from hPSCs Recapitulates In Vivo Signaling Pathways

During early development, signaling molecules from organizers direct early neuroectoderm phenotype specification. Thus, to optimize the phenotype specification of MGE cells from hPSCs, we sought to understand temporal and combinatorial regulations by relevant signaling molecules. H9 cells were differentiated as floating spheres in the presence of LDN193189 and SB431542 to facilitate differentiation into neuroectodermal lineages of hPSCs [25] Inhibition of Wnt signaling was shown to induce telencephalic identity during neural plate formation [27, 28], and thus, we used IWP2, a chemical inhibitor of Wnt signaling, to enhance rostralization of early neuroectoderm and subsequently to inhibit dorsalization of neuroectoderm[29]. We first tested the dosage of SHH signaling on phenotype specification of early neuroectoderm, since the degree of SHH activation regulates the subregional identity of LGE vs. MGE within the ventral telencephalon [23]. At 10 nM SAG (Smoothened agonist), there was modest increase in MGE specification, but at 100 nM SAG, there was significantly higher induction of the MGE phenotype (FIG. 1*a*). However, when we analyzed the expression of isl1, a general ventral telencephalic marker that is expressed in both MGE- and LGE-derived cells, there was no significant difference between 10 nM and 100 nM SAG, suggesting that with high SHH activation, the number of MGE cells increased at the expense of LGE cells. Thus, we used 100 nM SAG for subsequent MGE induction experiments.

Figure 2A:
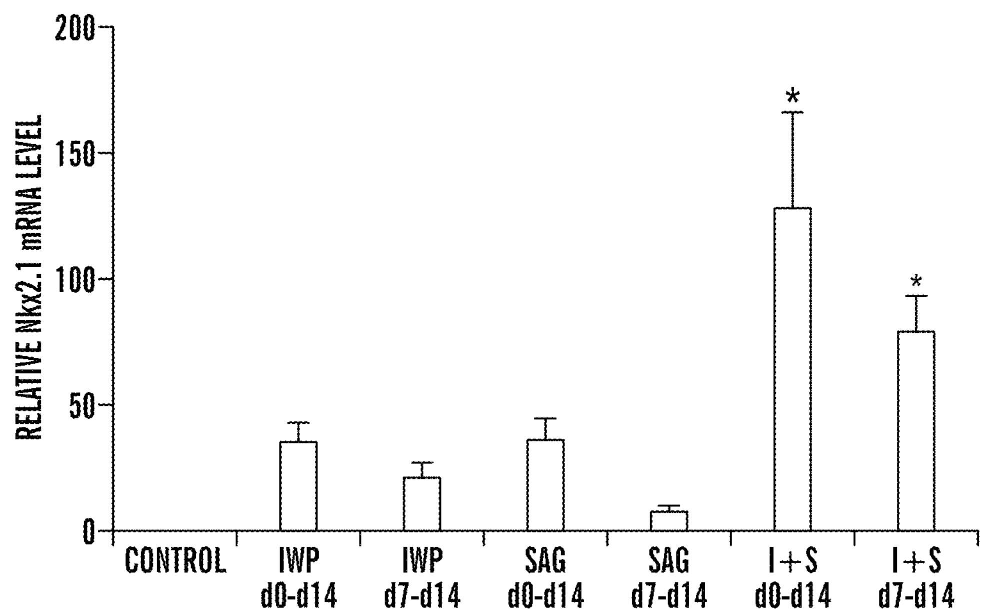
FIGS. 2*a* to 2*b* are graphs depicting optimization of MGE derivation from PSCs. H9 hESCs were differentiated with LDN193189 and SB431542 as floating spheres and analyzed by whole mount immunocytochemistry at day 3 and day 7. Using this protocol, neuroectoderm starts to appear as early as d3, shown by Pax6 staining, and by day 7, the majority of cells express Pax6. (data not shown).

We next tested the optimal treatment time frame of each signaling molecules. Since we observed most of the cells express Pax6 by day 7 of differentiation (FIG. 2*a*-2*b*), we tested whether modulation of Wnt and SHH signaling is optimal during or after neuroectoderm formation. With treatment starting at day 0 of differentiation, there was a significant increase in MGE specification compared to treatment starting at day 7 (data not shown; IWP+SAG 6.77% vs. 24%), suggesting that regionalization signaling during early differentiation is more efficient than after neuroectoderm formation. Differentiating hPSCs were also treated with IWP2 or SHH alone or in combination. With single molecule treatment, there was only a mild increase in MGE specification, but the combination of Wnt blocker and SHH activator yielded a synergistic increase in MGE specification (data not shown; 5.16% or 0.79% vs. 24%; with a day 0 start day). We observed similar results with Nkx2.1 mRNA expression levels by real time PCR (FIG. 2*a*). Since SHH continues to be required for Nkx2.1 expression, even after initial specification of ventral telencephalic identity [30], we tested whether additional treatment with SHH is beneficial for MGE induction. SAG treatment in the 3rd week of differentiation increased Nkx2.1 level mildly but significantly (FACS analysis data not shown).

Figure 1B:
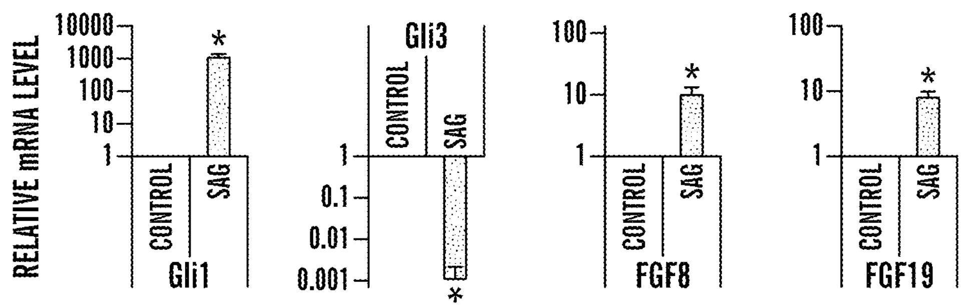
Figure 1C:
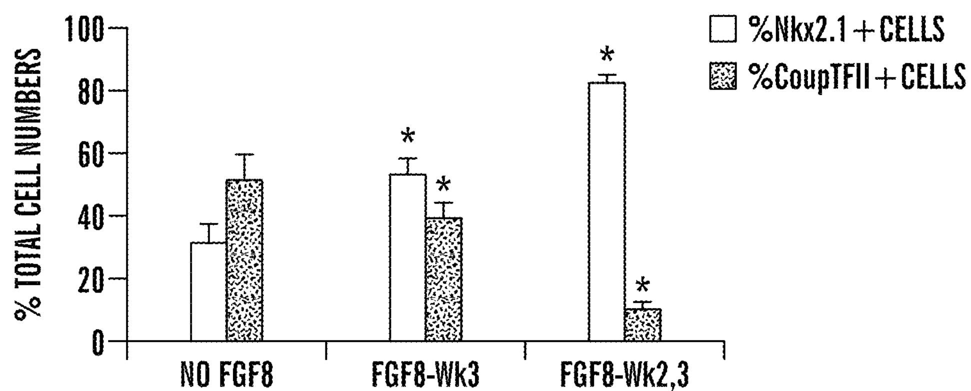
Figure 3A:
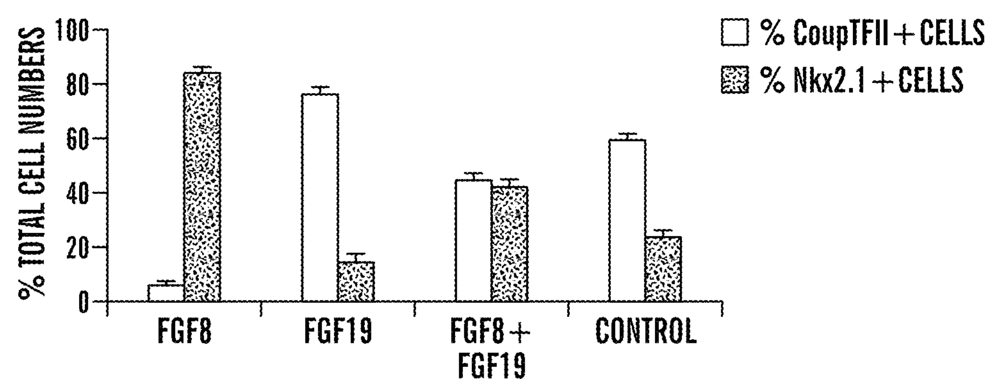
FIGS. 3*a* to 3*c* are graphs showing that FGF8 and FGF19 regulate rostral caudal identity of ventral telencephalic cells.
Figure 3B:
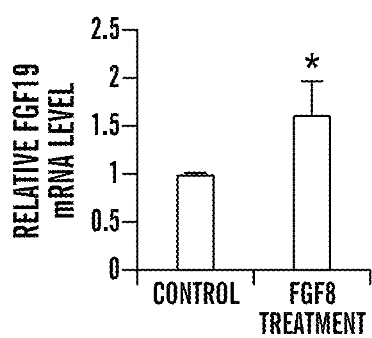
Figure 3C:
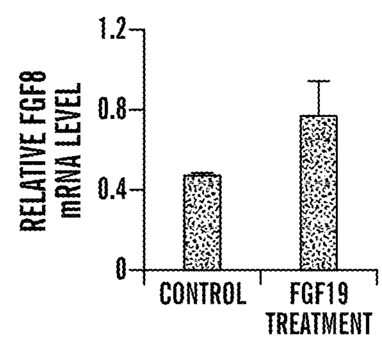

Conflicting results from recent studies on early activation of the SHH pathway [17, 18] prompted us to investigate the downstream events triggered by SHH activation during early differentiation. As expected from previous studies [31, 32], there was strong induction of Gli1 activator by SHH activation, as well as strong Gli3 expression reduction (FIG. 1*b*). Repression of Gli3 is accompanied by induction of the rostralizing signal FGF8 [6, 31], but at the same time, early SHH activation also induced the expression of FGF15/19 (FIG. 1*b*), which antagonizes the rostralizing effect of FGF8 during mouse telencephalic development, [22, 24]. Thus, to compensate the effect of FGF15/19 induction by strong SHH activation, we tested the effect of exogenous addition of FGF8, to shift the balance toward rostralization. In the absence of FGF8 signaling, both MGE and CGE phenotypes appear, as shown by Nkx2.1 expression and CoupTFII expression (FIG. 1*c*, images not shown). FGF treatment in the 2nd and/or 3rd week of differentiation significantly increased MGE differentiation at the expense of CGE differentiation (FIG. 1*c,d* images not shown), successfully counteracting SHH-induced caudalizing effect of FGF15/19. Furthermore, applying FGF19 exogenously instead of FGF8, resulted in most of the cells taking up CGE identity (FIG. 3*a*, images not shown), further supporting the role of FGF8/FGF19 signaling in determining rostral/caudal telencephalic identity. Exogenous addition of FGF19 increased diencephalic differentiation as shown by Nkx2.2 expression (images not shown; 0.61+0.38% Nkx2.2+/total cells vs. 4.19+0.77% Nkx2.2+/total cells for FGF8-treated and FGF19-treated cells, respectively, n=4), but diencephalic cells remained a minority even with FGF19 treatment, suggesting that employment of early Wnt inhibitor successfully rostralized the early neuroectoderm to telencephalic identity. Since it has been reported that FGF8 can induce FGF19 expression during CNS development [33], we tested such possibility in our system. Exogenous application of FGF8 did increase FGF19 expression mildly but significantly, whereas exogenous application of FGF19 had no effect on FGF8 expression (FIGS. 3*b* and 3*c*).

Generated CGE cells express another CGE marker Sp8 (images not shown; 61.76+7.86% Sp8+/total cells, n=4). CoupTFII+ cells seldom co-express Nkx2.1 (images not shown) further supporting their CGE identity rather than dorsolateral or caudal MGE nor co-express diencephalic marker Nkx2.2 (data not shown). After further differentiation, these CoupTFII-expressing cells generated VIP-expressing or Calretinin-expressing neurons (Suppl. FIGS. 3*d* and *f;* 10.46+1.35% VIP+/total cells and 16.77+5.36% Calretinin+/total cells, n=4), consistent with their CGE identity [1], whereas only a few stratal projection neurons and no Somatostatin-expressing nor Parvalbumin-expressing neurons were present (images (data not shown); 1.42+0.49% Isl1+/total cells and 1.06+0.54% Darpp32+/total cells, n=4).

Figure 4A:
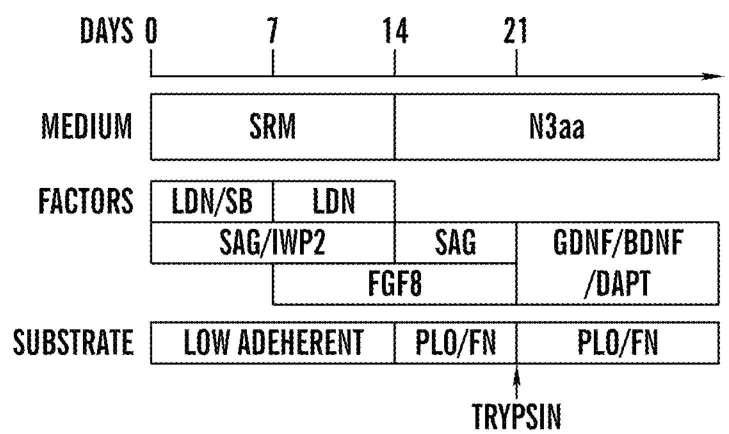
FIGS. 4*a* to 4*c* show the optimized MGE derivation protocol efficiently generates MGE cells from multiple PSC lines.
Figure 4B:
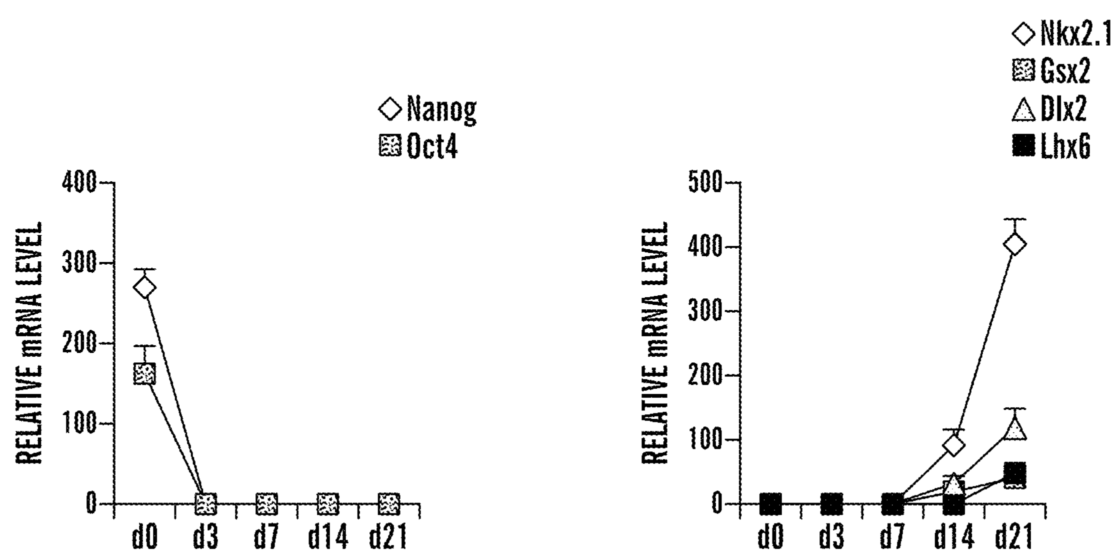
Figure 4C:
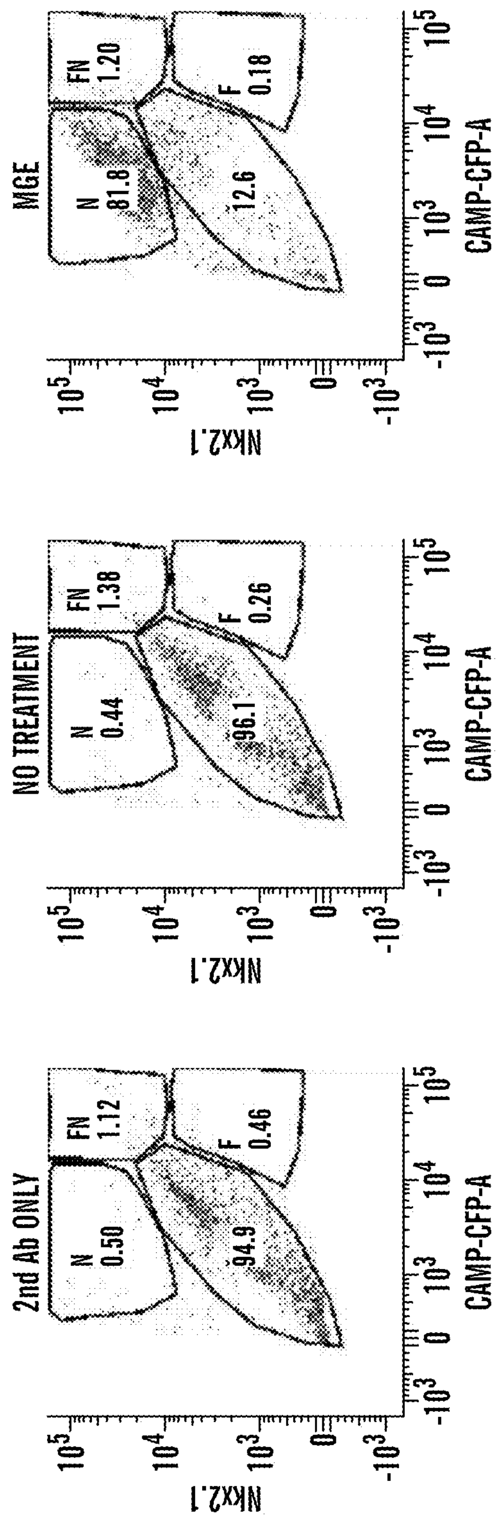

Optimized Induction Conditions Efficiently Generate MGE Cells from Multiple hPSCs Thus, our optimized conditions employ blocking Wnt signaling in the 1st and 2nd week of differentiation, strong activation of the SHH pathway for the 1st three weeks of differentiation and FGF8 signaling in the 2nd and 3rd week of differentiation (FIG. 4*a*). Real time PCR analysis under these optimal conditions showed that pluripotent stem cell markers Nanog and Oct4 expression is downregulated by day 3, and expression of ventral telencephalic markers Nkx2.1, GSX2, DLX2 become evident starting at day 14, followed by expression of the postmitotic MGE marker Lhx6 at day 21 (FIG. 4*b*). We differentiated two human embryonic stem cell (hESC) lines (H7 and H9) and one induced pluripotent stem cell (iPSC) line (iPSC2497) using MGE-inducing signals, and observed efficient MGE derivation (Nkx2.1+) at day 25 of differentiation, whereas in absence of MGE-inducing signals (IWP2, SAG and FGF8) all cells were of the dorsal telencephalic fate (Pax6+) (data not shown). FACS analysis revealed that more than 80% of the total cells were induced to the MGE phenotype (FIG. 4*c*). Further immunocytochemistry analysis (data not shown) revealed that the majority of induced cells also express independent MGE markers Olig2 (71.8+3.7% of total cells, n=4) and FoxG1 (89.8+2.0% of total cells, n=4).

Human MGE Cells Generate GABAergic Interneurons

Figure 5A:
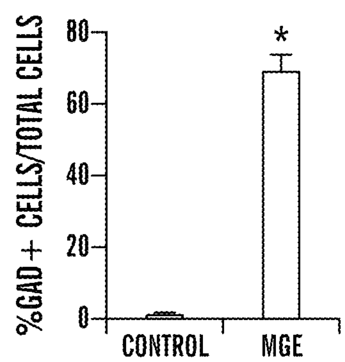
FIGS. 5*a* to 5*b* are graphs indicating that human MGE cells generate GABAergic interneurons.
Figure 5B:
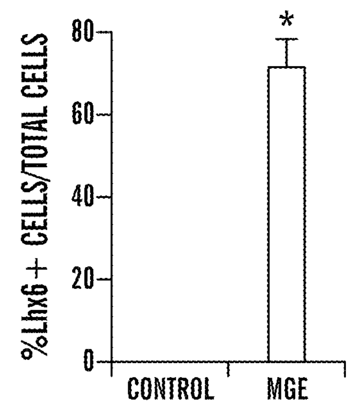

Further differentiation of MGE cells efficiently generated GABAergic neurons, based on GAD expression (FIG. 5*a* and data not shown; 69.1+4.1% GAD+/total cells with 86.3+4.0% β-tubulin+/total cells), whereas without this treatment, few GAD expressing neurons were observed (FIG. 5*a* and data not shown). In fact, absence of MGE inducing signaling yielded mostly glutamatergic neurons after differentiation (data not shown), as expected from their Pax6+ dorsal telencephalic identity. Robust induction of GABAergic neurons was also observed from H7- and iPSC2497-derived neurons under our optimized conditions (data not shown; 88.8+2.1% vs. 84.4+3.4% GABA+/β-tubulin+ cells. p=0.32, n=4). These GABAergic neurons express Lhx6, showing their MGE origin, however under control conditions no Lhx6-expressing cells were observed (FIG. 5*b*). H7 and iPSC2497 cells also robustly generated Lhx6+ neurons under MGE-generating conditions (data not shown; 77.6+4.5% vs. 74.4+3.0% Lhx6+/β-tubulin+ cells. p=0.56, n=4). In addition, these GABAergic neurons co-express Sox6 (data not shown; 88.2+2.5% Sox6+/GABA+ cells. p=, n=4), that was recently shown to be very specific marker for human MGE-derived interneurons [34]. Some of these cells expressed Calbindin (22.23±6.0% total cells, n=4; data not shown), which is expressed in some of the migrating interneurons. Some of these cells express more mature interneuron markers Parvalbumin (0.87±0.32% of total cells, n=4; data not shown) and Somatostatin (1.53±0.57% of total cells, n=4; data not shown) at this time point, as would be predicted from their MGE origin. We also observed the presence of minority of cells with alternate phenotypes at this time point (data not shown; 0.86+0.38% Nkx2.2+/total cells, 1.24+0.47% isl1+/total cells, 0.32+0.16% ER81+/total cells, 0.63+0.36% ChAT+/total cells, 2.75+1.05% Tbr1+/total cells, n=4). No midbrain dopaminergic neurons are observed (data not shown), consistent with our and other's previous study showing activation of Wnt signaling is important for specification of midbrain dopaminergic neurons [35, 36], whereas in the current protocol active inhibition of Wnt signaling was employed. Very few VIP-expressing or Calretinin-expressing cells were observed at this time point (data not shown). In addition, there were small number of olig2-expressing cells (2.86+1.37% total cells, n=4), but few mature astrocyte or oligodendrocyte differentiation observed at this time point (data not shown), as expected from the long time it takes for human glia cells to mature [37-39]. In the absence of FGF8 treatment, many CGE cells were generated as determined by Immunocytochemistry after 25 days of differentiation without FGF8 treatment; Immunocytochemistry after 60 days of differentiation with or without FGF8 treatment; and Immunocytochemistry after 60 days of differentiation without FGF8 treatment (data not shown).

Immunocytochemistry analysis on MGE cells at day 60 of differentiation: few Glutamatergic neurons are generated from MGE cells, whereas many glutamatergic neurons are generated from Pax6+ cells differentiated without added ventralizing/rostralizing signaling modulations (data not shown).

Figure 6A:
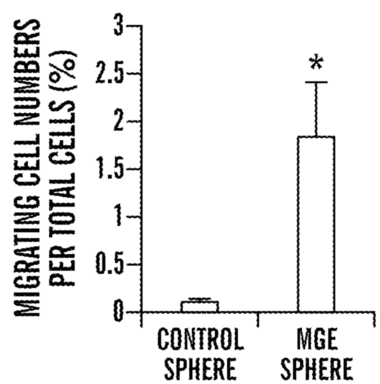
FIGS. 6*a* to 6*d* indicate the migration property of human MGE cells. MGE or Cortical spheres derived from H9 hESCs were plated on Matrigel substrate and analyzed 5 days after plating by brightfield microscopy or immunocytochemistry (images not shown).
Figure 6B:
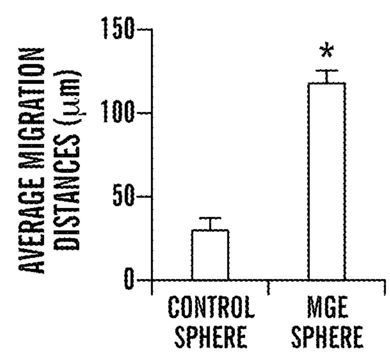
Figure 7A:
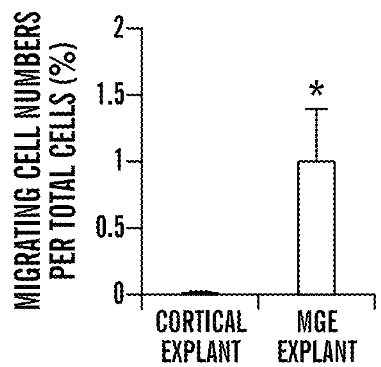
FIGS. 7*a* to 7*b* show graphs depicting migration analyses on mouse E14 cortical or MGE explant culture. Cortical or MGE explants were placed on thin layer of matrigel substrate and analyzed for 2 dimensional migration 5 days after plating by brightfield microscopy.
Figure 7B:
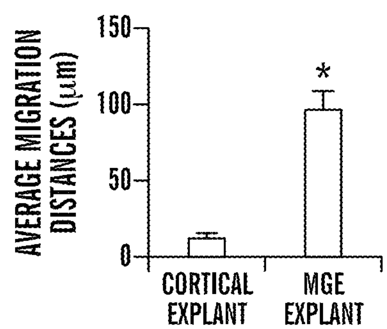

During embryonic development, interneurons show robust tangential migration all the way to the developing cortex. We therefore tested whether hPSC-derived interneurons show such migratory characteristics. We reaggregated MGE-derived cells or uninduced control cells in low attach round bottom 96 well plates, and plated spheres on Matrigel coated surfaces. Five days after plating, migration out of MGE cells clusters was observed compared to control clusters, and was expressed in terms of migrating cell numbers and migration distances (FIGS. 6*a* to 6*b*). Similar migration pattern was observed on matrigel-coated surfaces using mouse cortical vs. MGE explant culture (FIGS. 7*a* to 7*b*. In addition, when we embedded MGE explant and human MGE sphere in 3 dimensional matrigel matrixes, they also showed comparable migration pattern (data not shown).

Figure 6C:
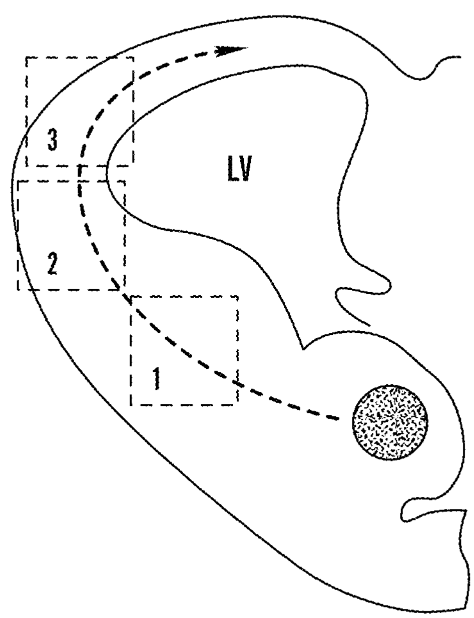
Figure 6D:
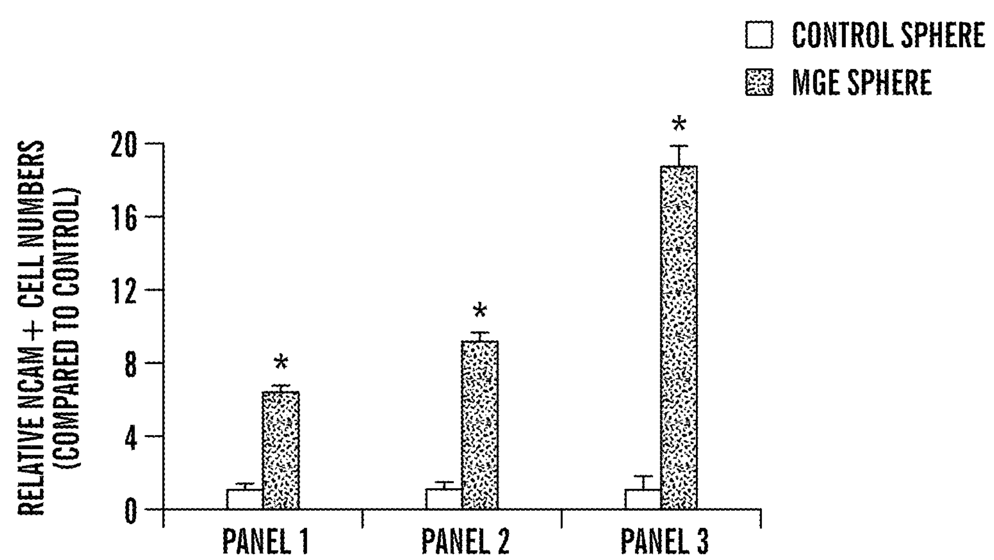

Heterochronic micro-transplants were performed to test whether human MGE cells can migrate toward the cortex as in the case of in vivo development. Control and MGE spheres pre-labeled with QDot® nanocrystals were transplanted into the ventral telencephalon (MGE) of slices prepared from E13.5 CD1 embryos and cultured for two days. Slices were processed for paraffin histology and 20 μm thick sections were used for immunohistochemistry and subsequent analysis. We binned the migration into three panels and performed a precise quantification of cell migration along the rostro-caudal axis in control and MGE sphere transplantations (FIG. 6*c*). Transplanted cells were detected by QDot® fluorescence and additionally human NCAM, human nuclei and human cytoplasm markers (data not shown). Cells that emanated from MGE spheres migrated robustly (data not shown) and a significant number of cells that were QDot® positive (data not shown) and NCAM positive (data not shown) were found in the dorsal telencephalon. In sharp contrast, cells from control spheres were found close to the transplantation site (data not shown). QDot® positive (data not shown) and NCAM positive (data not shown) cells were markedly reduced in the dorsal telencephalon in control sphere transplantations. Migratory cell morphology was detected with human NCAM and human cytoplasm antibodies at high magnifications (data not shown). A human nucleus marker was used to further characterize identification and visualization of cell migration from transplanted control and MGE spheres (data not shown). While fewer cells migrated from control spheres (data not shown), robust cell migration was observed from MGE spheres (data not shown), depicting robust migration in the ventral telencephalon en route to the dorsal telencephalon. Cell counting analysis of migrating NCAM+ cells showed significantly more MGE cells compared to control cells along the route of tangential migration from ventral to dorsal telencephalon (FIG. 6*d*).

Figure 8A:
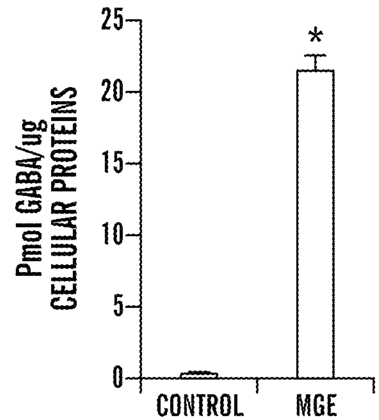
FIGS. 8*a* to 8*f* show functional properties of H9 MGE-derived GABAergic interneurons. a. GABA determination from MGE-derived neuronal cultures by HPLC analysis (Mean+S.E.M.; n=3). MGE-derived cells form synaptic connection, shown by overlap and juxtaposition of Synaptophysin foci with GABA staining after 6 weeks of differentiation (data not shown).
Figure 8B:
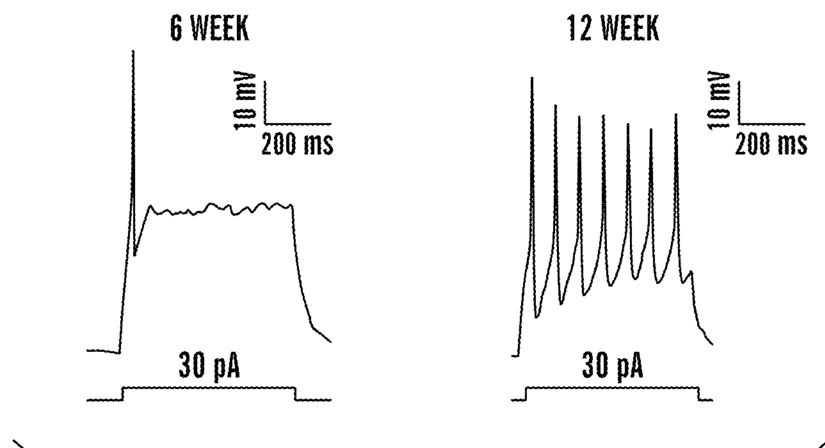
Figure 8C:
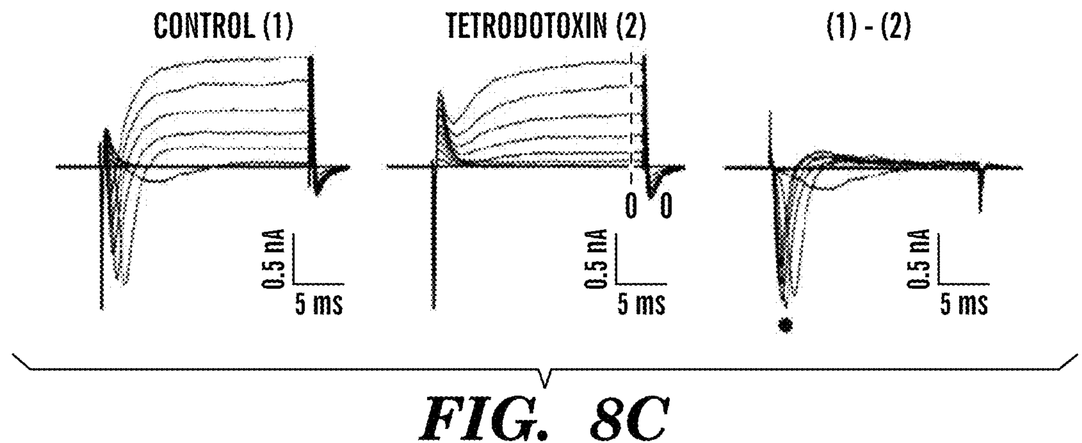
Figure 8D:
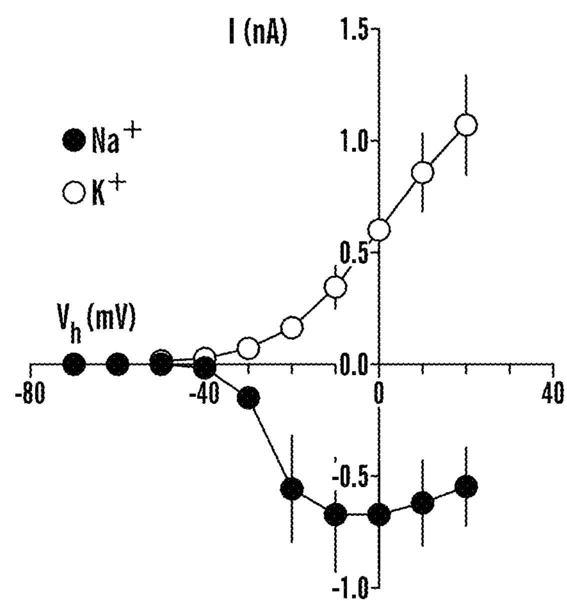
Figure 8E:
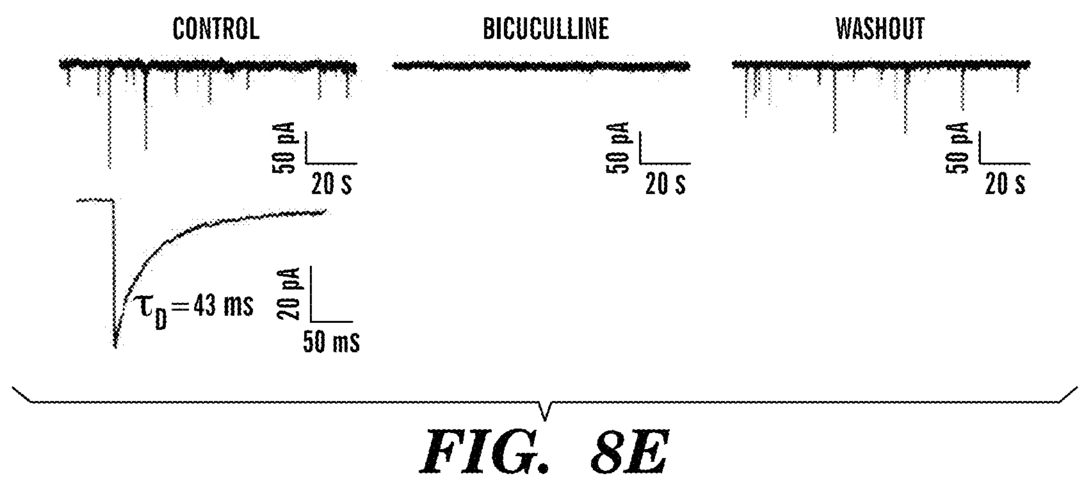
Figure 8F:
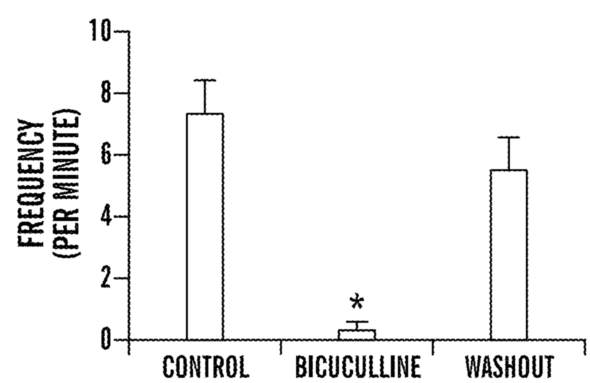

HPLC analysis showed that generated interneurons produce robust GABA levels compared to control cells (FIG. 8*a*). One important functional characteristic of neurons is synapse formation to communicate with other neurons. Thus, we tested whether these MGE-derived neurons are able to form synaptic connections. Immunocytochemistry analysis followed by confocal microscopy showed that GABA-expressing neurites colocalized or juxtaposed with Synaptophysin foci, a presynaptic protein (data not shown). Next, we examined whether MGE-derived cells have neuronal membrane properties using whole-cell patch clamp technique (data not shown). In current-clamp mode, injection of depolarizing currents to 6-week-old cells induced action potential firings in 4 out of 5 cells, whereas for 12-week-old cells all 10 cells examined fired action potential (FIG. 8*b*). Most 6-week-old cells displayed single action potentials, whereas 12-week-old cells started to show repetitive action potentials with uniform interspike intervals (one out of ten cells). Moreover, in voltage-clamp mode, voltage pulses evoked both transient inward currents and sustained outward currents, which were activated at membrane potential >−40 mV in all 6 cells examined (FIGS. 8*c* to 8*d*). Rapidly desensitizing inward currents were completely blocked by tetrodotoxin, a voltage-gated Na+ channel blocker, suggesting these cells express voltage-gated Na+ channels. Next, we examined spontaneous postsynaptic currents to determine whether these cells form functional synapses. In voltage-clamp mode at −70 mV, spontaneous currents were detected in all 11 cells examined. These currents were blocked almost completely by bicuculline, a GABAA receptor inhibitor (FIGS. 8*e* to 8*f*), indicating that the inhibitory neurotransmitter GABA mediated most of the spontaneous postsynaptic activities recorded in these cells. These results suggest that cells derived from hESCs form functional GABAergic synapses.

Figure 9:
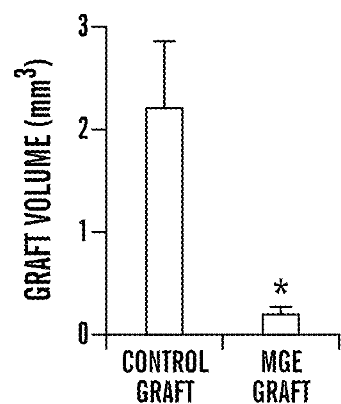
FIG. 9 shows a graph depicting graft volume analysis of cortical cells vs. MGE cells from an experiment showing that transplanted MGE cells generate neural grafts enriched with GABAergic neurons. H9-derived MGE cells generate well-contained neural grafts, whereas untreated cells (cortical cells) generate large and disruptive grafts with rosette structures, as analyzed 5 weeks after transplantation (immunohistochemistry data not shown (Mean+S.E.M.; n=10, P<0.05, two tailed t-test). The experiment also showed that more grafted cells migrate in the host brain at 5 months after grafting. MGE cells generated neural graft, shown by double staining of human nucleus specific antibody with Nkx2.1 antibody, as analyzed 5 weeks post grafting. Some of the grafted cells retain Nkx2.1 or Lhx6 expression at 5 weeks after transplantation. MGE cells generate graft enriched with GABAergic neurons, as analyzed 5 weeks after transplantation. Immunocytochemistry analysis indicated that MGE cells derived neurons form synaptic connection in the host brain (data not shown). Immunohistochemistry analysis 5 months post grafting was also performed.
Figure 10:
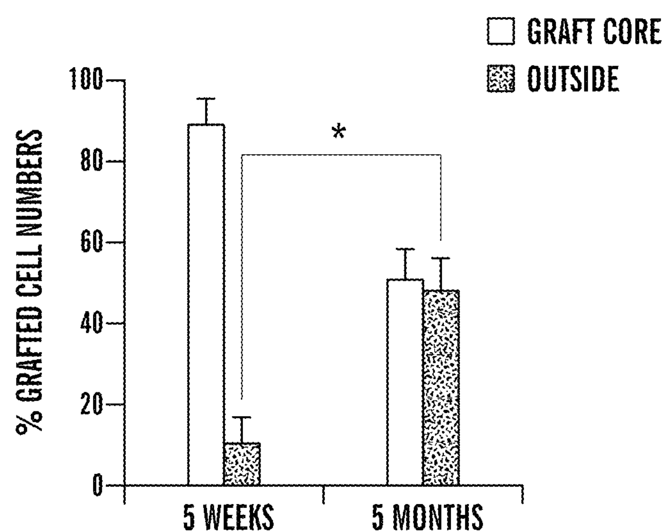
FIG. 10 shows a graph depicting percentage of grafted cells. Transplantation analysis of MGE cells was done. H9 MGE-derived grafted cells show migration out of the graft core as shown by immunocytochemistry analysis at 5 weeks and 5 months post grafting (data not shown), followed by cell counting analysis (Mean+S.E.M.; n=5, P<0.05, two tailed t-test). By immunohistochemistry analysis, many of the grafted cells express neuronal marker, β-tubulin. There are minorities of proliferating cells in MGE-derived grafts 5 weeks and 5 months after grafting. immunocytochemistry of alternate phenotypes on MGE grafts showed few astrocytes or oligodendrocytes are present at 5 weeks post grafting. Immunocytochemistry analysis on the expression of synaptic marker genes, Synaptophysin and PSD95 was also performed.

Human MGE-Derived Cells Generate Well-Contained Neural Grafts Enriched with GABAergic Neurons To analyze the in vivo behavior of human MGE-derived cells, we transplanted H9-derived interneurons at 5 weeks of differentiation into the striatum of NOD SCID mice. Control cells with dorsal telencephalic patterning were also transplanted for comparison. Whereas control cells massively proliferate and form big grafts with rosette structures (FIG. 6*a*-*d*) reminiscing of their massive proliferation during human brain development, MGE-derived cells form well-contained grafts (data not shown). Supporting this observation, the average graft volume of cortical cells was 2.22+0.64 mm3, whereas that of MGE-derived cells was 0.21+0.07 mm3 (FIG. 9). Five weeks post grafting, some cells were observed to have migrated out of the MGE graft core into the host brain, but, more cells migrated out of the graft core five months after grafting (data not shown, FIG. 10; 4810+1309 cells per graft (n=10) for 5 week grafts and 5438+2082 cells per graft (n=5) for 5 months grafts), sometimes with no graft core at all with even distribution of the grafted cells throughout the entire striatum (data not shown). MGE-derived cells generated mostly neural grafts, shown by co-labeling of human nucleus with NeuN (data not shown; 77.5+7.0% NeuN+/Human Nuclei+ cells) and β-tubulin (data not shown). Some of the these cells retained Nkx2.1 expression (data not shown; 27.57+7.83% Nkx2.1+/Human Nuclei+ cells) at 5 weeks post transplantation, and some of them expressed the MGE-derived interneuron specific transcription factor Lhx6 (data not shown; 22.53+2.78% Lhx6+/Human Nuclei+ cells), which is expressed in all MGE-derived migrating immature interneurons and subsequently is down regulated in some of mature MGE-derived interneurons [1]. Transplanted cells generated grafts largely composed of GABAergic interneurons, shown by coexpression of GABA with human NCAM and human nuclei (data not shown; 58.97+4.52% GABA+/human Nuclei+ cells). At 5 weeks post grafting, there were small portion of immature proliferating cells present in the graft, which was further reduced by 5 months post grafting (data not shown; 5.59+3.46% and 1.05+0.74% Ki67+/Human Nuclei+ cells, respectively). There are minority of cells with alternate phenotypes as shown in data not shown (0.69+0.38% Nkx2.2+/Human Nuclei+ cells, 4.48+1.02% CoupT-FII+/Human Nuclei+ cells, 0.72+0.31% ER81+/Human Nuclei+ cells, 0.89+0.52% Darpp32+/Human Nuclei+ cells, 0.95+0.33% Tbr1+/Human Nuclei+ cells and 1.05+0.62% ChAT+/Human Nuclei+ cells). There were few astrocytes or oligodendrocytes at this time point (data not shown). PSD95 foci overlapped with human specific NCAM+ fibers (data not shown), suggestive of glutamatergic synaptic connection from the host to the graft. Synaptic connection with the host brain was also indicated by co-localization or juxtaposition of human NCAM with Synaptophysin foci (data not shown). In the same line, many VGAT foci were observed juxtaposed with Gephyrin foci (data not shown), and Synaptophysin foci with PSD95 foci (data not shown). In addition, in 5 months old grafts, parvalbumin-expressing or somatostatin-expressing neurons are often observed (data not shown; 15.7+6.1% Parvalbumin+/Human Nuclei+ cells and 17.7+5.9% Somatostatin+/Human Nuclei+ cells), confirming the developmental potential of generated MGE cells.

Example I Discussion

Efficient generation of homogeneous populations of specific differentiated progenies of hPSCs is an important prerequisite to realize the full potential of hPSCs for disease modeling, regenerative medicine and bioassays [12]. In this study, employing a stepwise combined and temporal regulation of dorsolateral and rostrocaudal signaling pathways we achieved a very effective and homogeneous differentiation of hPSCs to MGE cells and then to GABAergic interneurons. Recent reports of efficient derivation of MGE cells showed conflicting results on the effect of timing of SHH activation, one study employing early activation of SHH for efficient induction of MGE cells [17], but the other showing that only late activation of SHH resulted in efficient MGE induction with early SHH activation mainly resulting in no MGE induction[18], though both study employed highly similar signaling modulation such as double SMAD inhibition (SB431542 along with BMP inhibitor Noggin or LDN193189), Wnt inhibition (DKK1) and strong SHH activation. In this study, we showed the pleiotropic effect of strong SHH signaling activation during early human neural differentiation, resulting in activation of mutually antagonizing signals. We also identified exogenous FGF8 addition as a way to overcome such pleiotropic and stochastic induction of MGE cell type by strong SHH activation and generated reliable populations of MGE cells, regardless of stochastic shift in SHH downstream signaling.

Salient features of our procedure include; first, a more efficient ventral telencephalic phenotype induction achieved by early modulation of Wnt and SHH signaling pathways even before neuroectoderm formation is completed, in line with the previous report [17]. This is consistent with previous developmental studies, where early inhibition of Wnt signaling is important for telencephalic induction of neural plate [27, 28] and early SHH signaling in anterior neural plate at the gastrula stage induces prospective ventral telencephalon, [40] even prior to neural tube formation. Maroof et al., also showed that early SHH activation is more effective in ventralization as illustrated by higher Nkx2.1 induction (>80% vs. about 50%; early vs. late SHH activation), [18] although they failed to fully derive MGE cells using early SHH activation and instead generated diencephalic cells. Second, the combined use of dorsoventral as well as rostrocaudal modulation using developmentally relevant signaling pathways resulted in accumulative increase of MGE induction, into very homogeneous populations. Here we have employed i) induction of neuroectoderm formation by double-SMAD inhibition [25], ii) inhibition of Wnt signaling, which otherwise caudalize [27, 28] and dorsalize [29] differentiating neuroectoderms, iii) strong activation of SHH signaling, resulting in MGE induction at the expense of LGE induction with mild SHH signaling, and iv) activation of FGF8 signaling, which induces the MGE phenotype at the expense of the more caudal CGE phenotype. In a previous study [41], a method using Activin A was shown to induce CGE type cells from mouse and human pluripotent stem cells, generating another important class of cortical interneurons. In the present study, we provide an alternate method to generate human CGE cells that express CoupTFII as well as Sp8 by employing step-wise approach that recapitulates normal embryonic development. To our knowledge, this is the most efficient and massive generation of human CGE cells (up to 80% of total cells). Such combined and temporal activation was also observed during differentiation of mouse ESCs [23], suggesting the conserved nature of early neural phenotype specification between these two species. In the absence of such signaling molecule modulation, most of the cells take up a dorsal telencephalic identity, in agreement with previous observation of human PSCs differentiation [5, 42].

In early brain development, FGF8 is expressed in the anterior neural ridge and is known to play an important role in determining rostral-caudal boundary whereby increased expression shifts the MGE and CGE boundary posteriorly [6]. SHH induces the ventral phenotype in the telencephalon by repressing Gli3 function [20], which represses FGF8 expression [21] and could indirectly induce FGF8 expression through repression of Gli3, indirectly exerting rostralizing activity. However, to complicate matters, it was also shown that SHH induces FGF15/19 expression in the forebrain development [22, 24], which was shown to antagonize the function of FGF8 during ventral telencephalic development [22, 23]. These developmental studies imply that small stochastic shift in SHH downstream signaling result in drastic shift of generated differentiation progenies, and demonstrate the power of developmental knowledge to reliably direct specific neural subtype differentiation.

MGE-derived interneurons show the ability to spontaneously differentiate into Lhx6-expressing GABAergic interneurons, showing them as phenotype-specified neural progenitors with intrinsic properties to become GABAergic interneurons. Enriched expression of Lhx6 after differentiation further demonstrates the MGE characteristic of derived progenitors, since Lhx6 expression is not observed in the preoptic area in the ventral telencephalon where Nkx2.1 is also expressed [43] nor in CGE-derived interneurons [1]. Derivation of a homogeneous MGE population was further confirmed by the limited presence of CoupTFII-expressing cells as well as the paucity of Pax6-expressing progenitors. The migratory property observed by these hPSC-derived interneurons on matrigel substrate and on E13.5 telencephalic slices well recapitulates their in vivo counterparts (Suppl. FIG. 5a-e and [44-46]). Remarkably, human MGE-derived neurons displayed physiological and electrophysiological properties consistent with GABAergic interneurons such as their ability to produce GABA, formation of synaptic connection and generation of action potentials and GABAergic post-synaptic activity. Even though postmitotic neuronal markers such as GAD and β-tubulin were robustly expressed at 6 weeks of differentiation, not all cells at this stage were able to fire action potentials, while at 12 weeks of differentiation all cells tested were able to. This long-term maturation process has been reported before [17, 47], and is likely to reflect the long-term maturation process of human brain development. The small proportions of MGE-derived interneurons that mature to express somatostatin and parvalbumin at 6 weeks of differentiation is also in line with this notion of long-term maturation of human neurons. Such early developing interneurons before full maturation will be of great value for cell replacement therapy with its migratory functions and for modeling neurodevelopmental disease such as schizophrenia enabling us to model early developmental time point during which the developing brains is known to be more susceptible to environmental challenge [48-50], and many known schizophrenia risk genes are highly expressed [51-53].

Another significant finding of this study is that hPSC-derived interneurons not only generated well-integrated grafts with migratory properties. This is in contrast with transplantation of control cells without MGE inducing signals, which extensively proliferated and generated large grafts with rosette structures in the striatum, reminiscent of their massive proliferation during human dorsal telencephalic development. Furthermore, we found that hPSC-derived MGE grafts were enriched with GABAergic interneurons that mature to express somatostatin and parvalbumin. Recent studies have shown the potential of GABAergic interneurons as sources for novel cellular therapies for epilepsy [54], Parkinson's disease [46] and injury-induced neuropathic pain[55]. Considering that optimal cell sources for such therapy is limiting, the development of a homogeneous population of human GABAergic interneurons now can allow for the clinic.

In summary, functional and authentic human MGE cells and GABAergic interneurons recapitulating the in vivo ventral telencephalic development can be efficiently generated in vitro by developmentally relevant dorsoventral and rostrocaudal modulation. This novel strategy will be useful in regenerative medicine, developmental studies, disease modeling, bioassay, and drug screening.

TABLE 1

Antibody list used in the experiments.

| Antibody | Species | Dilution | Source |
|---|---|---|---|
| β-tubulin | Rabbit | 1/2000 | Covance |
| β-tubulin | Mouse | 1/2000 | Covance |
| Calbindin | Rabbit | 1/10000 | Swant |
| Calretinin | Goat | 1/5000 | Swant |
| CoupTFII | Mouse | 1/1000 | Persus Proteomics |
| FoxG1 | Rabbit | 1/500 | Abcam |
| GABA | Rabbit | 1/1000 | Sigma |
| GAD 65/67 | Rabbit | 1/1000 | Millipore |
| Glutamate | Rabbit | 1/15000 | Sigma |
| Isl1 | Mouse | 1/1000 | DSHB |
| Lhx6 | Rabbit | 1/1000 | Gift from Dr. Pachnis |
| NCAM | Mouse | 1/1000 | SCBT |
| Nestin | Mouse | 1/1000 | Millipore |
| Neuropeptide Y | Sheep | 1/5000 | Millipore |
| Nkx2.1 (TTF1) | Rabbit | 1/2000 | Epitomics |
| Nucleus | Mouse | 1/1000 | Millipore |
| Olig2 | Rabbit | 1/500 | Millipore |
| Parvalbumin | Mouse | 1/5000 | Millipore |
| Pax6 | Rabbit | 1/200 | Covance |
| Pax6 | Mouse | 1/1000 | DSHB |
| PSD-95 | Rabbit | 1/1000 | Cell Signaling |
| PSD-95 | Mouse | 1/1000 | Neuro Mab |
| Somatostatin | Rat | 1/5000 | Millipore |
| Synaptophysin | Rabbit | 1/2000 | Pierce |
| Synaptophysin | Mouse | 1/500 | Abcam |
| VGLUT | Mouse | 1/1000 | DSHB |
| NeuN | Mouse | 1/500 | Chemicon |
| VGAT | Rabbit | 1/1000 | Synaptic Systems |
| Gephyrin | Mouse | 1/1000 | Synaptic Systems |
| Human Cytoplasm | Mouse | 1/500 | Stem Cells Inc |
| NKX2.2 | Mouse | 1/1000 | DSHB |
| SP8 | Goat | 1/500 | SBT |
| ER81 | Goat | 1/1000 | SCBT |
| Tbr1 | Rabit | 1/500 | Abcam |
| ChAT | Goat | 1/500 | Millipore |
| DARPP32 | Rabbit | 1/500 | SCBT |
| VIP | Rabbit | 1/1000 | Immunostar, Inc. |
| Pitx3 | Rabbit | 1/1000 | Gift from Dr. Burbach |
| TH | Sheep | 1/1000 | Pelfreez |
| Ki67 | Mouse | 1/1000 | Millipore |
| Sox6 | Rabbit | 1/1000 | Millipore |
| Somatostatin | Goat | 1/1000 | SCBT |
| CNPase | Mouse | 1/1000 | Sigma |
| GFAP | Rabbit | 1/1000 | Dako |

REFERENCES FOR EXAMPLE 1

1. Wonders C P, Anderson S A. The origin and specification of cortical interneurons. Nat Rev Neurosci. 2006; 7:687-696.
2. Tamamaki N, Yanagawa Y, Tomioka R et al. Green fluorescent protein expression and colocalization with calretinin, parvalbumin, and somatostatin in the GAD67-GFP knock-in mouse. J Comp Neurol. 2003; 467:60-79.
3. Chiang C, Litingtung Y, Lee E et al. Cyclopia and defective axial patterning in mice lacking Sonic hedgehog gene function. Nature. 1996; 383:407-413.
4. Fuccillo M, Rallu M, McMahon A P et al. Temporal requirement for hedgehog signaling in ventral telencephalic patterning. Development. 2004; 131:5031-5040.
5. Li X J, Zhang X, Johnson M A et al. Coordination of sonic hedgehog and Wnt signaling determines ventral and dorsal telencephalic neuron types from human embryonic stem cells. Development. 2009; 136:4055-4063.
6. Fukuchi-Shimogori T, Grove E A. Neocortex Patterning by the Secreted Signaling Molecule FGF8. Science. 2001; 294:1071-1074.
7. Garel S, Huffman K J, Rubenstein J L. Molecular regionalization of the neocortex is disrupted in Fgf8 hypomorphic mutants. Development. 2003; 130:1903-1914.
8. Sussel L, Marin O, Kimura S et al. Loss of Nkx2.1 homeobox gene function results in a ventral to dorsal molecular respecification within the basal telencephalon: evidence for a transformation of the pallidum into the striatum. Development. 1999; 126:3359-3370.
9. Liodis P, Denaxa M, Grigoriou M et al. Lhx6 activity is required for the normal migration and specification of cortical interneuron subtypes. 2007; 27:3078-3089.
10. Arber C E, Li M. Cortical interneurons from human pluripotent stem cells: prospects for neurological and psychiatric disease. Frontiers in Cellular Neuroscience. 2013; 7.
11. Castiglioni V, Onorati M, Rochon C et al. Induced pluripotent stem cell lines from Huntington's disease mice undergo neuronal differentiation while showing alterations in the lysosomal pathway. Neurobiol Dis. 2012; 46:30-40.
12. Bellin M, Marchetto M C, Gage F H et al. Induced pluripotent stem cells: the new patient? Nat Rev Mol Cell Biol. 2012; 13:713-726.
13. Matsui T, Akamatsu W, Nakamura M et al. Regeneration of the damaged central nervous system through reprogramming technology: Basic concepts and potential application for cell replacement therapy. Exp Neurol. 2012.
14. Brennand K J, Simone A, Jou J et al. Modelling schizophrenia using human induced pluripotent stem cells. Nature. 2011; 473:221-225.
15. Lee G, Ramirez C N, Kim H et al. Large-scale screening using familial dysautonomia induced pluripotent stem cells identifies compounds that rescue IKBKAP expression. Nat Biotechnol. 2012; 30:1244-1248.
16. Egawa N, Kitaoka S, Tsukita K et al. Drug screening for ALS using patient-specific induced pluripotent stem cells. Sci Transl Med. 2012; 4:145ra104.
17. Nicholas C R, Chen J, Tang Y et al. Functional Maturation of hPSC-Derived Forebrain Interneurons Requires an Extended Timeline and Mimics Human Neural Development. Cell Stem Cell. 2013; 12:573-586.
18. Maroof A M, Keros S, Tyson J A et al. Directed differentiation and functional maturation of cortical interneurons from human embryonic stem cells. Cell Stem Cell. 2013; 12:559-572.
19. Liu Y, Weick J P, Liu H et al. Medial ganglionic eminence-like cells derived from human embryonic stem cells correct learning and memory deficits. Nat Biotechnol. 2013; 31:440-447.
20. Rallu M, Machold R, Gaiano N et al. Dorsoventral patterning is established in the telencephalon of mutants lacking both Gli3 and Hedgehog signaling. Development. 2002; 129:4963-4974.
21. Aoto K, Nishimura T, Eto K et al. Mouse GLI3 regulates Fgf8 expression and apoptosis in the developing neural tube, face, and limb bud. Dev Biol. 2002; 251:320-332.
22. Borello U, Cobos I, Long J E et al. FGF15 promotes neurogenesis and opposes FGF8 function during neocortical development. Neural Dev. 2008; 3:17.
23. Danjo T, Eiraku M, Muguruma K et al. Subregional specification of embryonic stem cell-derived ventral telencephalic tissues by timed and combinatory treatment with extrinsic signals. J Neurosci. 2011; 31:1919-1933.
24. Ishibashi M, McMahon A P. A sonic hedgehog-dependent signaling relay regulates growth of diencephalic and mesencephalic primordia in the early mouse embryo. Development. 2002; 129:4807-4819.
25. Chambers S M, Fasano C A, Papapetrou E P et al. Highly efficient neural conversion of human ES and iPS cells by dual inhibition of SMAD signaling. Nat Biotechnol. 2009; 27:275-280.
26. Chung S, Moon J-I, Leung A et al. ES cell-derived renewable and functional midbrain dopaminergic progenitors. Proceedings of the National Academy of Sciences. 2011; 108:9703-9708.
27. Houart C, Caneparo L, Heisenberg C et al. Establishment of the telencephalon during gastrulation by local antagonism of Wnt signaling. Neuron. 2002; 35:255-265.
28. Nordstrom U, Jessell T M, Edlund T. Progressive induction of caudal neural character by graded Wnt signaling. Nat Neurosci. 2002; 5:525-532.
29. Gunhaga L, Marklund M, Sjodal M et al. Specification of dorsal telencephalic character by sequential Wnt and FGF signaling. Nat Neurosci. 2003; 6:701-707.
30. Gulacsi A, Anderson S A. Shh maintains Nkx2.1 in the MGE by a Gli3-independent mechanism. Cereb Cortex. 2006; 16 Suppl 1:i89-95.
31. Hebert J M, Fishell G. The genetics of early telencephalon patterning: some assembly required. Nat Rev Neurosci. 2008; 9:678-685.
32. Ruiz i Altaba A, Palma V, Dahmane N. Hedgehog-Gli signalling and the growth of the brain. Nat Rev Neurosci. 2002; 3:24-33.
33. Gimeno L, Martinez S. Expression of chick Fgf19 and mouse Fgf15 orthologs is regulated in the developing brain by Fgf8 and Shh. Developmental dynamics: an official publication of the American Association of Anatomists. 2007; 236:2285-2297.
34. Ma T, Wang C, Wang L et al. Subcortical origins of human and monkey neocortical interneurons. Nat Neurosci. 2013; 16:1588-1597.
35. Chung S, Leung A, Han B S et al. Wnt1-lmx1a forms a novel autoregulatory loop and controls midbrain dopaminergic differentiation synergistically with the SHH-FoxA2 pathway. Cell Stem Cell. 2009; 5:646-658.
36. Kriks S, Shim J W, Piao J et al. Dopamine neurons derived from human ES cells efficiently engraft in animal models of Parkinson's disease. Nature. 2011; 480:547-551.
37. Krencik R, Weick J P, Liu Y et al. Specification of transplantable astroglial subtypes from human pluripotent stem cells. Nat Biotechnol. 2011; 29:528-534.
38. Wang S, Bates J, Li X et al. Human iPSC-derived oligodendrocyte progenitor cells can myelinate and rescue a mouse model of congenital hypomyelination. Cell Stem Cell. 2013; 12:252-264.
39. Hu B Y, Du Z W, Zhang S C. Differentiation of human oligodendrocytes from pluripotent stem cells. Nature protocols. 2009; 4:1614-1622.
40. Gunhaga L, Jessell T M, Edlund T. Sonic hedgehog signaling at gastrula stages specifies ventral telencephalic cells in the chick embryo. Development. 2000; 127:3283-3293.
41. Cambray S, Arber C, Little G et al. Activin induces cortical interneuron identity and differentiation in embryonic stem cell-derived telencephalic neural precursors. Nature communications. 2012; 3:841.
42. Mariani J, Simonini M V, Palejev D et al. Modeling human cortical development in vitro using induced pluripotent stem cells. Proceedings of the National Academy of Sciences. 2012.
43. Flames N, Pla R, Gelman D M et al. Delineation of multiple subpallial progenitor domains by the combinatorial expression of transcriptional codes. J Neurosci. 2007; 27:9682-9695.
44. Wichterle H, Garcia-Verdugo J M, Herrera D G et al. Young neurons from medial ganglionic eminence disperse in adult and embryonic brain. Nat Neurosci. 1999; 2:461-466.
45. Alvarez-Dolado M, Calcagnotto M E, Karkar K M et al. Cortical inhibition modified by embryonic neural precursors grafted into the postnatal brain. J Neurosci. 2006; 26:7380-7389.
46. Martinez-Cerdeno V, Noctor S C, Espinosa A et al. Embryonic MGE precursor cells grafted into adult rat striatum integrate and ameliorate motor symptoms in 6-OHDA-lesioned rats. Cell Stem Cell. 2010; 6:238-250.
47. Johnson M A, Weick J P, Pearce R A et al. Functional Neural Development from Human Embryonic Stem Cells: Accelerated Synaptic Activity via Astrocyte Coculture. The Journal of Neuroscience. 2007; 27:3069-3077.
48. Aguilar-Valles A, Luheshi G N. Alterations in cognitive function and behavioral response to amphetamine induced by prenatal inflammation are dependent on the stage of pregnancy. Psychoneuroendocrinology. 2011; 36:634-648.
49. Piper M, Beneyto M, Burne T H et al. The neurodevelopmental hypothesis of schizophrenia: convergent clues from epidemiology and neuropathology. Psychiatr Clin North Am. 2012; 35:571-584.
50. Li Q, Cheung C, Wei R et al. Prenatal immune challenge is an environmental risk factor for brain and behavior change relevant to schizophrenia: evidence from MRI in a mouse model. PLoS One. 2009; 4:e6354.
51. Xu B, Ionita-Laza I, Roos J L et al. De novo gene mutations highlight patterns of genetic and neural complexity in schizophrenia. Nat Genet. 2012; 44:1365-1369.
52. Lin M, Pedrosa E, Shah A et al. RNA-Seq of human neurons derived from iPS cells reveals candidate long non-coding RNAs involved in neurogenesis and neuropsychiatric disorders. PLoS One. 2011; 6:e23356.
53. Gilman S R, Chang J, Xu B et al. Diverse types of genetic variation converge on functional gene networks involved in schizophrenia. Nat Neurosci. 2012; 15:1723-1728.
54. Baraban S C, Southwell D G, Estrada R C et al. Reduction of seizures by transplantation of cortical GABAergic interneuron precursors into Kv1.1 mutant mice. Proc Natl Acad Sci USA. 2009; 106:15472-15477.
55. Braz J M, Sharif-Naeini R, Vogt D et al. Forebrain GABAergic neuron precursors integrate into adult spinal cord and reduce injury-induced neuropathic pain. Neuron. 2012; 74:663-675. 2

Example 2

Methods

PSC Culture and Differentiation into MGE Cells

Human H7 ESC (WA07, WiCell, passage 41-51) was maintained on Matrigel (BD, San Hose, Calif.) in mTeSR media (Invitrogen, Carlsbad, Calif.) with 10 ng/ml bFGF (Peprotech, Rocky Hill, N.J.), and passaged using Dispase (Stem Cell Technologies, Vancouver, BC, Canada). For differentiation, PSCs were trypsinized and grown as floating aggregates in low adherent flasks in KSR media (20% knockout serum replacement, DMEM, 2 mM L-glutamine and 10 μM β-mercaptoethanol (all from Invitrogen)). Rock inhibitor (Y-27632, 10 μM, Tocris, Bristol, United Kingdom) was added on the first day of differentiation. After two weeks of floating culture, cells were transferred to polyornithine-(PLO; 15 mg/ml; Sigma, St. Louis, Mo.) and fibronectin-(FN; 1 mg/ml; Sigma, St. Louis, Mo.) coated surfaces in N3 media. For MGE induction, cells were treated with LDN193189 (100 nM, Stemgent, Cambridge, Mass.) from d0 to d14, with SB431542 (10 μM, Tocris) from d0 to d7, with IWP2 (5 μM, EMD Millipore) from d0 to d7, with SAG (0.1 μM, EMD Millipore) from d0 to d21, and with FGF8 (100 ng/ml, Peprotech) from d8 to d21 (Kim et al., 2014). After 3 weeks of differentiation, cells were transferred to differentiation media (N3 media (Chung et al.) with 10 ng/ml GDNF (Peprotech), 10 ng/ml BDNF (Peprotech) and 2.5 μM DAPT (Tocris). At day 25 of differentiation, cells were subject to a fluorescence-activated cell sorting (FACS). Cells were trypsinized and incubated with anti-ENCAM antibody (BD) in FACS media (phenol-free, $Ca^{++}$, $Mg^{++}$-free Hank's buffered saline solution (HBSS; Invitrogen, Carlsbad, Calif.) containing Penicillin-Streptomycin, 20 mM D-Glucose and 2% fetal bovine serum) for 20 min, followed by incubation for 10 min with Alexafluor-568-conjugated anti-rat IgM antibodies (Invitrogen, Carlsbad, Calif.). All washing steps were performed in FACS media. Cells were filtered through cell strainer caps (35 gm mesh) to obtain a single cell suspension (5×106 cells/ml for sorting), followed by FACS using FACSAria (BD Biosciences, San Jose, Calif.) and FACSDiva software (BD Biosciences, San Jose, Calif.). Debris, dead cells and doublets were excluded by forward and side scatter gating. ENCAM positivity was determined compared to negative controls lacking the primary antibody and lacking primary and secondary antibodies. A portion of sorted cells were plated on PLO/FN-coated coverslips for immunocytochemical analysis and the rest were resuspended in transplantation media (HBSS with 10 ng/ml GDNF, 10 ng/ml BDNF and 20 μl M Boc-Asp(OMe) fluoromethyl ketone (BAF; Sigma-Aldrich)) and used for transplantation.

Induction of Temporal Lobe Epilepsy (TLE) in Nod-Scid Mice

The Animal Care and Use Committee at McLean Hospital approved all animal procedures. The mice were housed with 12 hr light/dark cycles with free access to food and water. For induction of TLE, 7-week old male and female Nod-Scid mice (Charles River Laboratory) were injected with 400 mg/kg Pilocarpine i.p., 30 minutes after N-methylscopolamine bromide (1 mg/kg, ip) administration to reduce peripheral cholinergic effects (Mazzuferi et al.). To limit the duration of status epilepticus (SE) and extent of damage in the hippocampus, diazepam (10 mg/kg) was injected ip 90 min after seizure induction. The severity of convulsive responses was monitored and classified according to the modified Racine scale (Shibley and Smith, 2002). Ten days after pilocarpine injection, mice that showed stage 3, 4 or 5 seizure were subject to 7 days of continuous video monitoring of spontaneous recurrent seizure (SRS) using Eco Black Box security camera system (Lorex Technology). Mice showing SRS with stage 3, 4 or 5 during the 7-day recording period were designated as "TLE mice" in this study, and they were randomly assigned for subsequent transplantation and behavioral analysis.

Transplantation of hMGE Cells into Hippocampus of TLE Model Mice.

FACS-sorted hESC-derived MGE cells or the same volume of transplantation media as described above were injected into hippocampus of TLE mice using a Leica Angle Two digital stereotaxic instrument (Leica Biosystems) fitted with a Cunningham Mouse Adaptor (Stoelting, Inc, Downers Grove, Ill.). TLE mice were anesthetized using an induction chamber supplied with 4-5% isoflurane (Sigma) mixed with 0.8-1 L/min oxygen using a calibrated vaporizer. Animals were then administered continuous isoflurane (1-2%) mixed with oxygen (0.8-1.0 L/min) via snout mask for the duration of anesthesia. Body temperature was maintained using air-activated iron oxide heat packets. Cell suspensions or control vehicle injections were disseminated throughout the hippocampus with one rostral injection and three caudal injections (Hunt et al., 2013) at the following coordinates: AP 1.75 mm, L +2.3 mm, V −1.7 mm for rostral CA3 site; AP 3.25 mm, L +3.0 mm, V −3.65 mm, −2.9 mm and −2.0 mm for the three caudal sites along the dorso-ventral axis of the hippocampus in this coronal plane. Injection coordinates were verified by ink injections as well as cell injection followed by histological analysis 1-2 weeks after transplantation. A total of 5×104 MGE cells in a 0.5 μl volume were delivered to each target coordinate. Sterile, stainless steel bone screw recording electrodes (diameter 0.5 mm, length 1.1 mm; Plastics One) soldered with lead wire were placed epidurally through rostral burr holes in the skull (AP 1.75 mm, L +2.3 mm), and reference electrodes were implanted caudal to lambda. Electrodes were cemented in place with a rapid-curing dental cement (DenMat Holdings, Lompoc, Calif.).

Behavioral Analysis

Mice were maintained under a 12-hours light/dark cycle with water and food available ad libitum. All behavioral tests were done during the light phase of the light/dark cycle.

Continuous Video-EEG Recording of Transplanted Mice

Three months after transplantation, seizure activity of control or MGE-transplanted TLE mice was recorded using a MP150 Biopac data acquisition System, EEG100C EEG amplifier module and AcqKnowledge 4.0 EEG Acquisition and Reader Software (BIOPAC Systems Inc.) along with Eco Black Box security camera system (Lorex Technology). EEG seizures with high-frequency, high-voltage synchronized polyspike profiles with amplitudes greater than 2-fold background and a duration of greater than 15 sec (Hunt et al., 2013) were analyzed using AcqKnowledge 4.0 EEG Acquisition and Reader Software (BIOPAC Systems Inc.) by investigators who were blind to treatment conditions. This was followed by confirmation of EEG seizure activity by video recording. Each animal was recorded over 5-10 days, totaling 42 days for naïve mice (n=6), 79 days for control TLE mice (n=11), and 83 days for MGE-transplanted TLE mice (n=9). The mice with more than 15,000 surviving human nucleus+ cells in each hippocampi were included in the behavioral analysis (One mouse from MGE-transplanted group did not meet this criterion and was excluded. It showed mild seizure activity with 0.7 seizure per day).

Y Maze

We used a three-arm Y maze for this study: each arm 3 cm wide, 40 cm in length, and with a wall height of 12 cm. Mice were initially placed within one arm, and the sequence and number of entries was recorded for each mouse over a 10 min period. The percentage of triads in which all three arms are represented (i.e., ABC, CAB or BCA, but not BAB for example), was recorded as a spontaneous alternation to estimate short-term memory. The number of arm entries was used as an indicator of locomotor activity. Arms were cleaned between tests to remove odors and residues. Y maze test was done under normal ambient room lighting.

Novel Object Recognition Test

For a training session, each mouse was placed into an open field box (42×42×31 cm) containing two identical objects and allowed to freely explore for 3 min. One hour after the training session, one of the familiar objects was replaced with a novel object (defined as the test session). The time that each animal spent exploring the novel object compared to the familiar object was recorded and traced using Ethovision software (Noldus, Wageningen, The Netherlands), using a 3 cm radius around each object as the "interaction zone". The test box and objects were cleaned between sessions. Results are expressed as recognition index (% time=time duration near novel object/[time duration near novel object+time duration near familiar object]×100). The percentage visit frequency is calculated as follows (% frequency=number of visit to novel object/[number of visit to novel object+number of visit to familiar object]×100).

Locomotion Test

The home cage (7½"×11½"×5") containing an individual mouse was placed in the center of a photobeam activity system (PAS) monitoring frames (San Diego Instruments) with 4×8 photobeam configuration for 15 min under standard overhead lighting conditions. Total photobeam break numbers were detected by PAS software.

Handling Test

Aggressiveness of the mice was assessed as described previously (Hunt et al., 2013) with some modifications. Each of the following three tasks was performed for 15 sec: 1) nonstressful handling (stroking slowly along the back of the mouse in the direction of the grain of fur), 2) stressful handling (vigorous stroking against the grain of the fur), 3) pinching at the tail base with a rubber-ended forceps (Fine Science tools). Reaction to each handling was scored by investigators blinded to treatment conditions using the following rating scale: 1-initial struggle, but calmed within 15 sec, 2-struggle for more than 15 sec, 3-struggle for more than 15 sec and exhibiting one or more defensive reactions (piloerection, flattening of the ears against the head, attempt to bite or back away from the experimenter), and 4-struggled for more than 15 sec and exhibited flight behavior (loud vocalization or wild running) Summation of these three scores provided a total aggressiveness score for each mouse.

Immunohistochemistry, Cell Counting and Statistical Analysis

Transplanted mice were terminally anesthetized with an ip overdose of pentobarbital (150 mg/kg, Sigma) and perfused transcardially with heparin saline (0.1% heparin in saline) followed by formaldehyde (4%) 2 weeks or 4 months post grafting. Brains were removed, postfixed in 4% formaldehyde for 12 hours, equilibrated in 20% sucrose/PBS solution, and then sectioned coronally at 40-□m using a freezing microtome. For immunofluorescence staining, tissue sections were incubated with blocking buffer (PBS, 10% normal donkey serum (NDS)) containing 0.1% Triton for 10 minutes. Cells were then incubated overnight at 4° C. with primary antibodies diluted in PBS containing 2% NDS. The primary antibody list can be found in Table S1. After rinsing with PBS, samples were incubated with fluorescent dye-labeled secondary antibodies (Alexa 488- Alexa 568- or Alexa 647-labeled IgG; Invitrogen, Carlsbad, Calif.) in PBS containing 2% NDS for 30 minutes at room temperature. After rinsing with PBS, Hoechst 33342 (4 mg/ml) was used for counterstaining, and tissue sections were mounted onto slides in Mowiol 4-88 (Calbiochem, Gibbstown, N.J.). Confocal analysis was performed using an Olympus DSU Spinning Disc Confocal on an IX81 inverted microscope (Center Valley, Pa.), installed with MetaMorph software. StereoInvestigator image-capture equipment and software (Microbright Field, Williston, Vt.) were used for cell counting and estimation of total cell number in the graft using the optical fractionator workflow from every 12th sections. A 400 μm×400 μm grid was used along with 200 μm×200 μm counting frame. For migration analysis, human Nuclei+ cells within 400 μm, between 400-800 μm, 800-1200 μm or 1200-1600 μm from injection tract were counted using separate markers.

To assess mossy fiber sprouting, Timm scores were determined as previously described (Shibley and Smith, 2002), with 0 for no ZnT3 staining in granule cell layer, 1 for patchy staining in granule cell layer, 2 for punctate staining in molecular layer and 3 for continuous staining in molecular layer.

For statistical analysis, we performed a t-test (alpha=0.05) for comparison of two groups using Prism6 software (Graph Pad). For multiple sample comparison, we performed analysis of variance (ANOVA) with an alpha level of 0.05 to determine possible statistical differences between group means. When significant differences were found, post hoc analysis was performed using Fisher's LSD ($\alpha$=0.05) again using Prism6 software. For samples with unequal variances, non-parametric Kruskal-Wallis test was performed using Prism6 software.

Transmission Electron Microscopy (TEM)

For TEM analysis, mice were perfused in 4% PFA/0.5% Glutaldehyde solution, and brains were removed, postfixed in the same fixative, and 40 □m coronal slices obtained using a vibrating microtome. Immunohistochemistry was performed as described above, using anti-human cytoplasm antibody and biotinylated anti-mouse antibody, followed by an ABC kit (Vector) and a diaminobenzidine (DAB) substrate kit (Vector) with Nickel intensification according to manufacturer's instruction. DAB-stained brain slices were post-fixed in an aqueous solution of 1% osmium tetroxide (OsO4, Electron Microscopy Sciences) and 1% potassium ferrocyanide (Electron Microscopy Sciences) for one hour, followed by embedding in Embed 812 epoxy resin (Electron Microscopy Sciences) using standard ethanol gradient dehydration and propylene oxide:resin gradient infiltration and polymerization protocols. Ultrathin (70-80 nm) sections were cut from graft core region and collected on 200 mesh copper grids (Electron Microscopy Sciences) previously cleaned ultrasonically in acetone. Images were acquired on a JEOL 1200EX TEM operating at 80 kV accelerating voltage.

Electrophysiology, Optogenetic Stimulations and Neurolucida Tracing

For electrophysiological studies, MGE cells were infected with lentivirus that express ChR2 (H134R)-GFP fusion protein under the control of synapsin promoter (UPenn vector core facility) at day 14 of differentiation. Transduction efficiency was 26.3±4.7% (n=4). The cells underwent FACS and were transplanted as described above. Two to five months after transplantation, acute brain slices containing the hippocampus were prepared using a vibrating microtome for electrophysiological analysis. After recovery, brain slices were placed in the recording chamber and continuously perfused at the rate of 1 mL per minute with the artificial cerebrospinal fluid containing 130 mM NaCl, 2.5 mM KCl, 2.5 mM CaCl2, 1 mM MgSO4, 1.25 mM NaH2PO4, 26 mM NaHCO3, and 10 mM glucose with 95% 02 and 5% CO2. Whole-cell patch-clamp recordings were performed at 31-33° C. using EPC-9 amplifier and Pulse v8.8 software (HEKA Elektronik). For recording grafted MGE-derived neurons (GFP+ cells) and host hippocampal interneurons, the patch electrodes (~5 MOhm resistance) were filled with solution containing 150 mM K-gluconate, 5 mM NaCl, 1 mM MgCl2, 10 mM HEPES, 0.2 EGTA, 2 mM MgATP, 0.5 mM NaGTP, and 5 mM biocytin (290 mOsm, adjusted to pH 7.3 with KOH). For recording GFP-host hippocampal neurons, the patch electrodes were filled with solution containing 140 mM Cs-methanesulfonate, 5 mM NaCl, 1 mM MgCl2, 10 mM HEPES, 0.2 EGTA, 2 mM MgATP, 0.5 mM NaGTP, 5 mM QX 314 chloride, and 5 mM biocytin (290 mOsm, adjusted to pH 7.3 with CsOH). Liquid junction potential of 15.5 and 8.9 mV was corrected for the K-gluconate-based and Cs-based pipette solutions, respectively. Series (access) resistance was not compensated. Blue collimated light-emitting diode (LED) with 470 nm peak wavelength (M470L2, Thorlabs) was used for photostimulations of grafted MGE-derived cells expressing ChR2-GFP. Brain slices in the recording chamber were illuminated through a 40× water-immersion objective lens (IR-Achroplan, Carl Zeiss). Illumination area was 0.26 mm2 and was centered at the cell patched for recording.

Offline data analysis was performed using Clampfit 9 program (Molecular Devices). Reagents were purchased from Tocris Bioscience (QX 314 chloride, biocytin, and NBQX) or Sigma-Aldrich (ATP, GTP, and bicuculline methochloride). For statistical analyses of electrophysiological data, we used ANOVA with Bonferroni's simultaneous multiple comparisons. Statistical analysis was performed with Minitab16 software (Minitab) and $p<0.05$ was considered statistically significant.

After electrophysiological recordings, brain slices were fixed in 4% paraformaldehyde at 4° C. overnight. Recorded cells loaded with biocytin were labeled with streptavidin, Alexa 568 conjugate (20 μg/mL in PBS, Molecular Probes) as described previously (Cho et al., 2013). Images of biocytin/streptavidin-labelled cells were taken with z-stack function using Leica TSC SP8 confocal microscope. The confocal images were then used for neuron tracing with Neurolucida software (Microbright Field, Williston, Vt.).

Single Cell Reverse Transcription-Polymerase Chain Reaction (scRT-PCR)

After whole-cell patch-clamp recording for more than 20 minutes, the recording pipettes were withdrawn slowly for the formation of outside-out patch. Intracellular contents (~6 μl) were expelled from the pipettes and collected in Eppendorf tubes containing 1.0 μl RNaseOUT (40 U/μl, Invitrogen) and 1.5 μl nuclease-free water and stored at −20° C. Samples were first treated with TurboDNase (Invitrogen) that is compatible with high-salt recording solutions to remove genomic DNA contamination, followed by reverse transcription using SuperScript III (Invitrogen) with pool of gene-specific outside primers (Table 3) in 20 ul reaction according to manufacturer's instruction. cDNAs were subject to 25 cycles (95° C., 2 min; 25 cycles of (95° C., 20 s; 55° C., 20 s; 72° C., 20 s); 72° C., 5 min) of pre-amplification using pool of gene-specific outside primers and GoTaq DNA polymerase (Promega) in 50 μl reaction. In the second round of PCR, 1 μl each cDNA was amplified using nested primers (Table S2) and GoTaq DNA polymerase (Promega) with 30 cycles (95° C., 2 min; 30 cycles of (95° C., 20 s; 55° C., 20 s; 72° C., 20 s); 72° C., 5 min) in 25 μl reaction. To check the possibility of mRNA contamination from surrounding tissues, recording patch pipettes were inserted into the same brain slices containing the hippocampus without the formation of tight giga-seal and its contents was analyzed likewise and did not show any signal above background level (n=3). As a positive control, we used 1 ng of total human brain RNA and all primers successfully amplified cDNA with correct size.

A decreased GABA induced inhibition of has repeatedly been demonstrated in TLE animal models (Cossart et al., 2001; Hirsch et al., 1999; Kobayashi and Buckmaster, 2003). Therefore, one possible therapeutic approach is to increase (the inhibitory neurotransmitter) GABA-mediated inhibition to suppress hyperexcitable neurons during seizure initiation. Early work exploring the potential for inhibitory neural grafts in controlling epileptic activity has shown promise and has inspired further studies (Fine et al., 1990; Lindvall and Bjorklund; Loscher et al., 1998). More recent experiments have shown that mouse GABAergic interneuron precursors engrafted into the TLE mouse brain decreased seizure activity (Baraban et al., 2009; Hattiangady et al., 2008; Hunt et al., 2013; Maisano et al., 2012).

However, for human TLE patients, it is critical to develop optimal human cell sources that can integrate into host circuitry, increase GABA-mediated inhibitory tone, and thereby reduce seizure activity in the epileptic brain. However, efficient translation of hPSC-derived interneurons could be hampered by their well-known, protracted maturation (Le Magueresse and Monyer, 201; Nicholas et al., 2013) For example, parvalbumin+ neurons acquire fast-spiking property only after postnatal maturation into early adolescence in mice (Doischer et al., 2008 o; Okaty et al., 2009).

Results

Human mGIN extensively migrate within the epileptic brain.

Figure 2B:
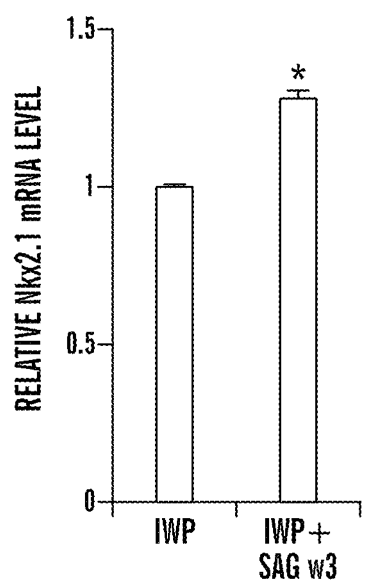
Figure 11A:
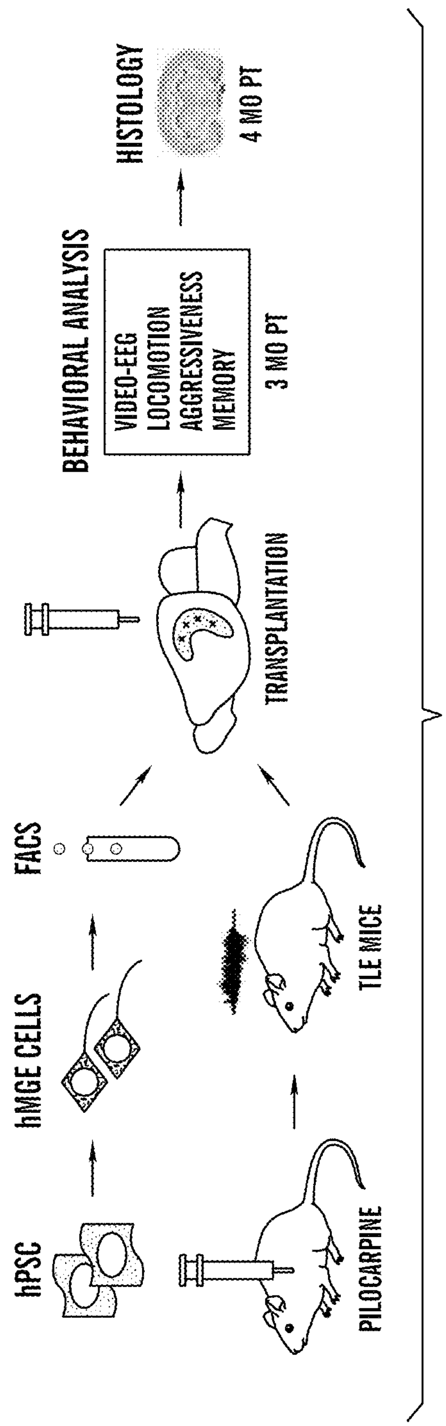
FIGS. 11*a* to 11*b* show a schematic and graph indicating that transplanted human mGIN migrate robustly and integrate in adult epileptic brains.
Figure 11B:
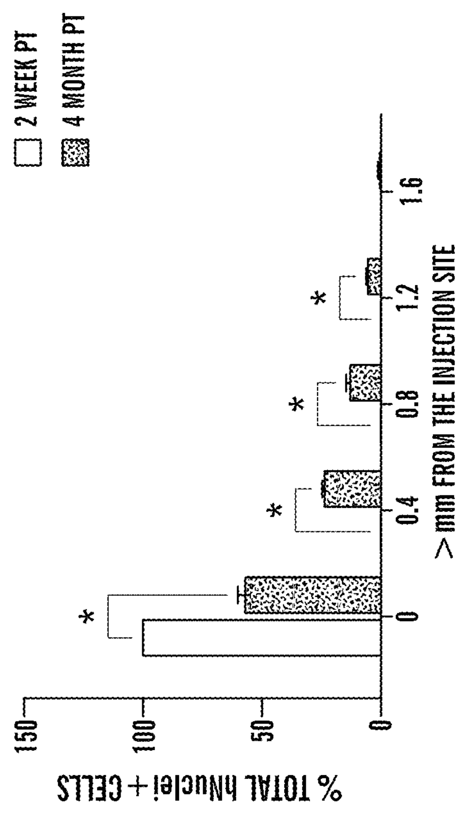
Figure 12A:
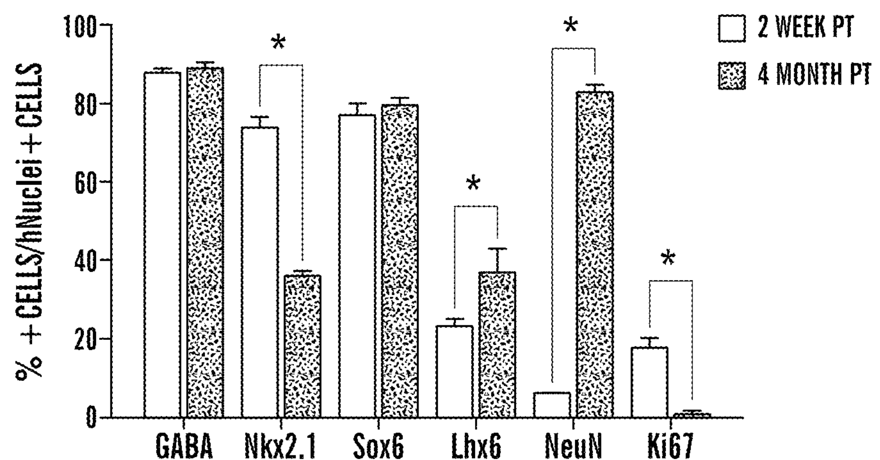
FIGS. 12*a* to 12*b* show graphs indicating that transplanted human MGE cells generate GABAergic interneurons in adult epileptic brains. Immunohistochemical analysis of transplanted cells was performed at 2 weeks and 4 months PT (data not shown) PT.
Figure 12B:
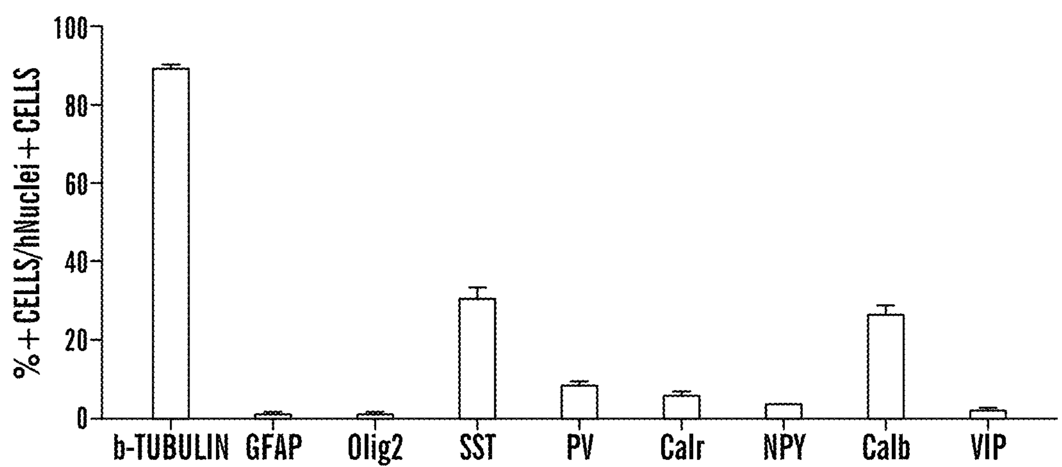
Figure 18A:
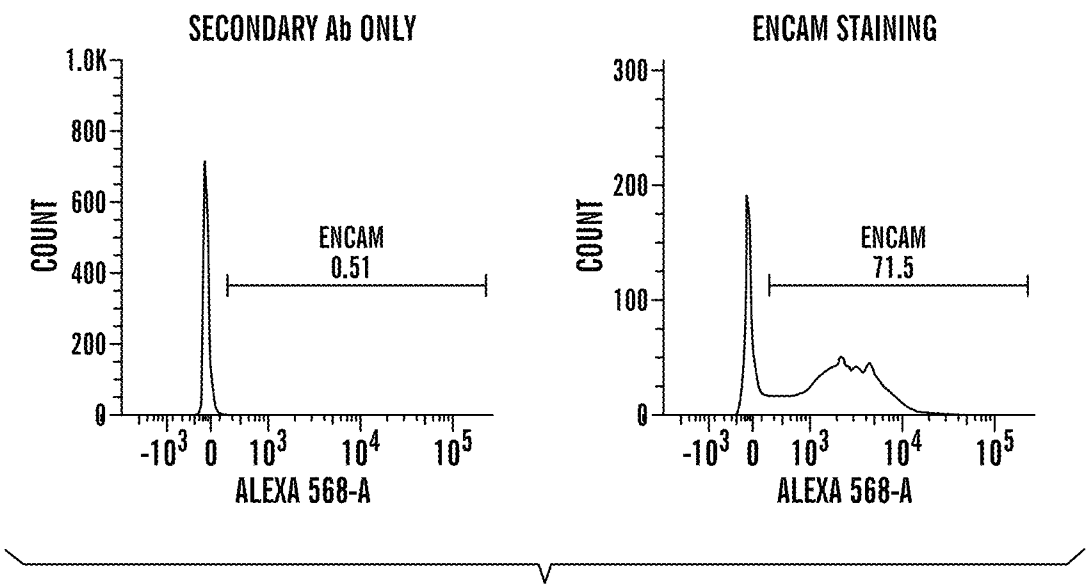
FIGS. 18*a* to 18*b*. FACS isolation of ENCAM+ cells after MGE differentiation of human pluripotent stem cells.
Figure 18B:
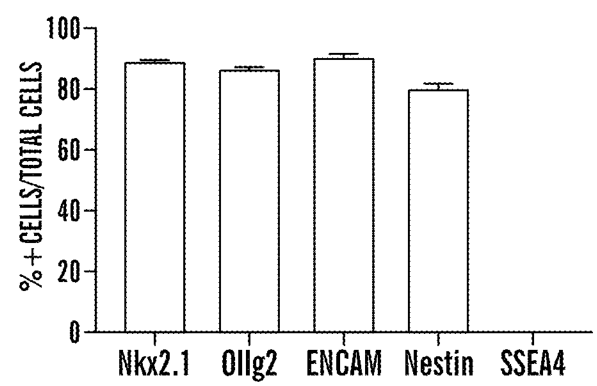
Figure 19:
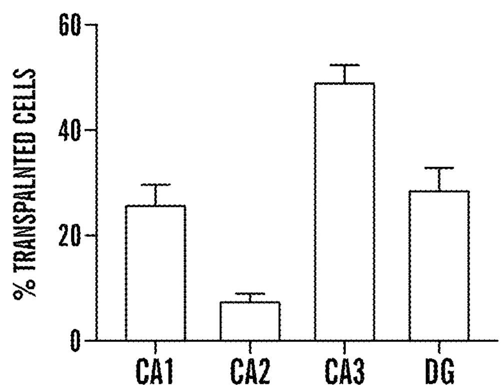
FIG. 19, is a graph of the quantification of transplanted cells in different areas of hippocampus. Mean+S.E.M (n=8). Counting trace and grid were used.

Human MGE cells were generated by in vitro differentiation of H7 human embryonic stem cells according to our optimized procedure (Kim et al., 2014), and purified by FACS using anti-ENCAM antibody prior to transplantation (FIG. 11*a*). Most of the FACS-sorted cells expressed the MGE markers Nkx2.1 and Olig2, as well as the early neural marker nestin, but no cells were positive for the pluripotent stem cell marker SSEA4 (data not shown, FIG. 18). We generated a mouse model for temporal lobe epilepsy (TLE) by injecting Nod-Scid mice with 400 mg/kg doses of pilocarpine. Animals demonstrating Racine stage 3-5 seizure activity upon induction with pilocarpine were further screened for occurrence of spontaneous recurrent seizures (SRS) over 7 days using continuous video monitoring starting 10 days after pilocarpine injection. Mice having at least one SRS during this 7-day screening period were used for further experiments and denoted as "TLE mice" in this study. Human MGE cells were disseminated throughout most of the hippocampus by depositing volumes of cell suspension within the rostral and caudal hippocampus bilaterally using 4 separate targets on each side as reported previously (Hunt et al., 2013) (FIG. 11*a*). Histological analysis showed that 2 weeks post-transplantation (PT), cells were primarily clustered near the injection site (59,027±18,724 total human nucleus+ cells per mouse, n=3; data not shown). At 4 months PT, however, transplanted mGIN extensively migrated, becoming well integrated within the host hippocampus (74,913±15,417 total human nucleus+ cells per mouse, n=8; data not shown and FIG. 19), without significant difference in the total surviving cell numbers compared to 2 weeks PT (p=0.58). At the transplantation core, grafted cells comprise 30.7±4.7 of total cells (n=6 mice). Stereological analysis demonstrated migration of transplanted human mGIN greater than 1.6 mm from the site of injection (FIG. 11*b*). At 2 weeks PT, most cells expressed GABA, Sox6 as well as Nkx2.1 (immunocytochemistry data not shown), with a minority of cells expressing the more mature neuronal marker NeuN (data not shown). However, at 4 months PT, the majority of cells expressed NeuN as well as GABA and Sox6 (immunocytochemistry data not shown) The expression of precursor marker Nkx2.1 was significantly diminished at 4 months PT compared to 2 weeks PT (FIG. 12*a* and data not shown), whereas the mature interneuron marker Lhx6 was significantly increased at 4 months PT compared to 2 weeks PT (FIG. 12*a* and data not shown). In addition, proliferating cell marker Ki67 was significantly decreased after 4 month PT compared to 2 weeks PT (FIG. 12*a* and data not shown). Further, at 4 month PT, GABAergic interneurons were found to have matured to express somatostatin, parvalbumin, calretinin, neuropeptide Y and calbindin (FIG. 12*b*, data not shown). As seen during in vivo embryonic development, interneuron maturation was not synchronous and cells with simple bipolar morphology and cells with more complex neurites coexist at this time point (data not shown). Transplanted cells generated very small numbers of astrocytes (GFAP+; FIG. 2*b* and data not shown) or oligodendrocyte lineage cells (Olig2+; FIG. 12*b* and data not shown).

Functional integration of human mGIN into the epileptic brain.

Figure 13A:
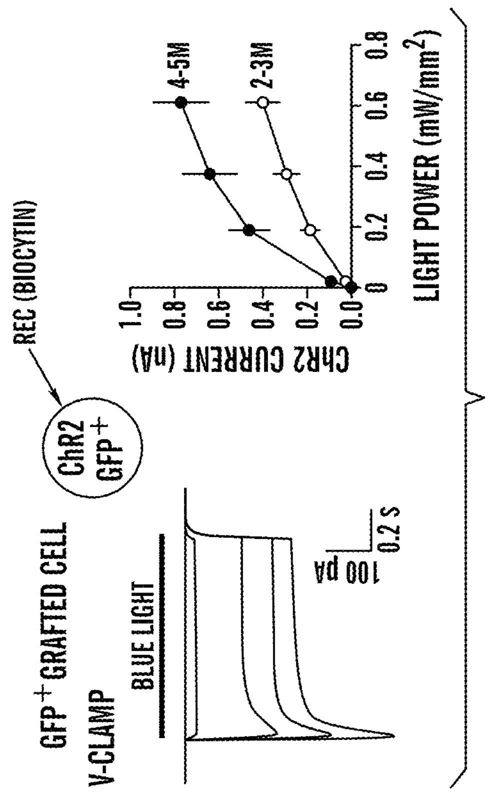
FIGS. 13*a* to 13*g*. Electrophysiological characterization of grafted human mGIN in the hippocampus.
Figure 13B:
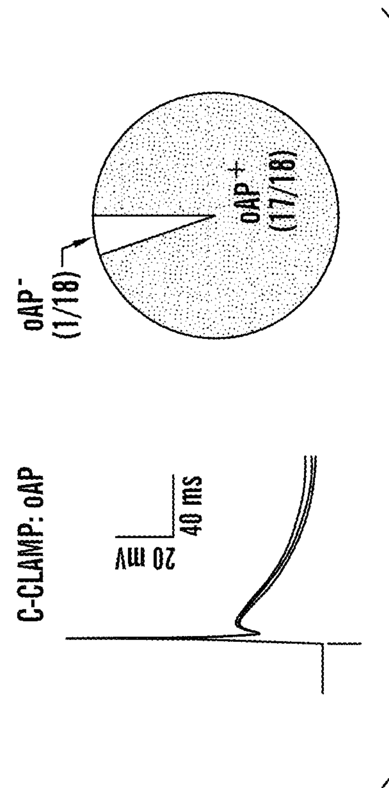
Figure 13C:
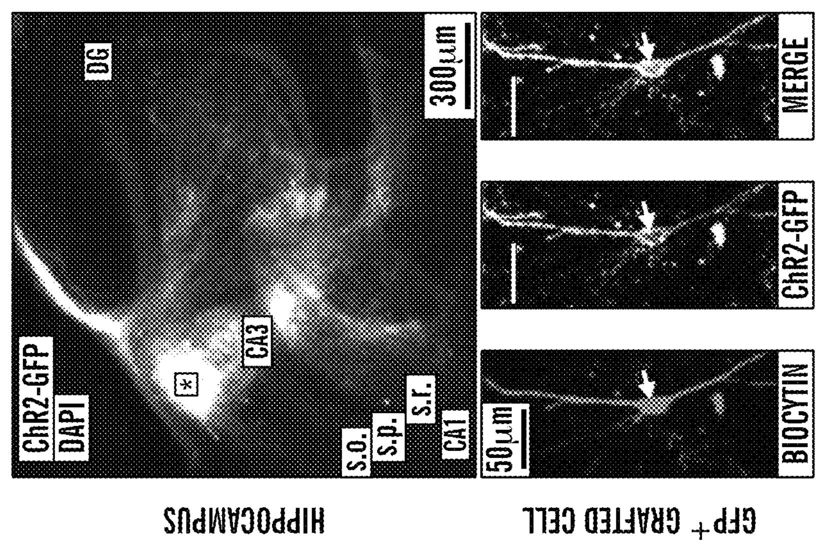
Figure 13D:
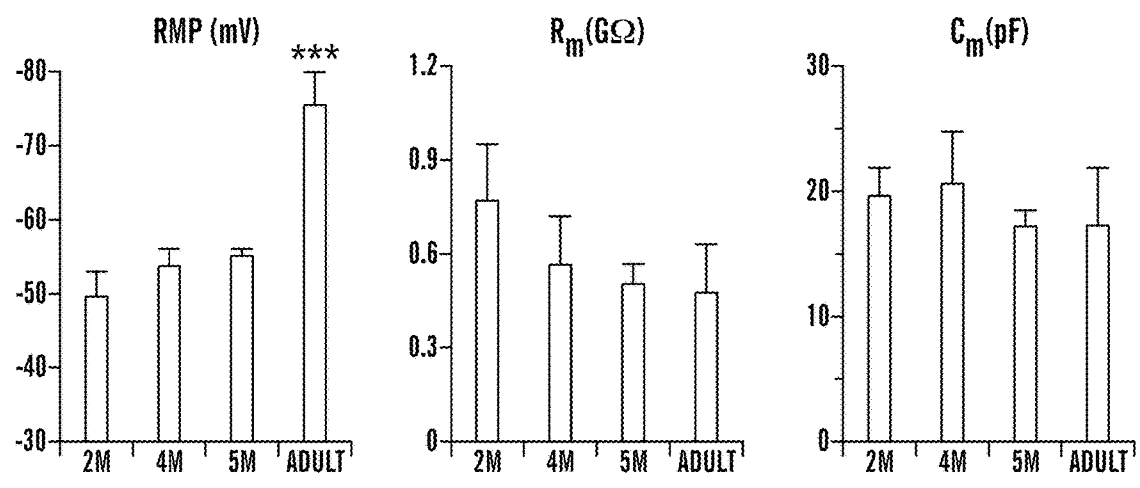
Figure 13E:
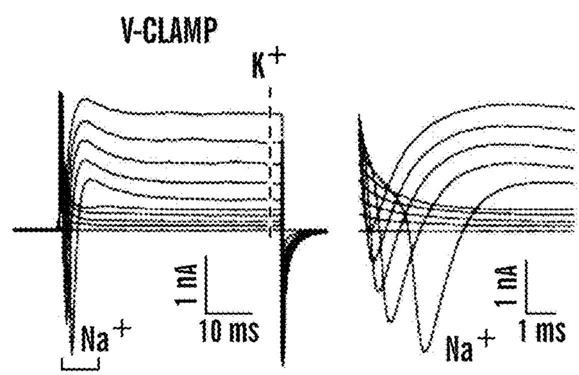
Figure 13F:
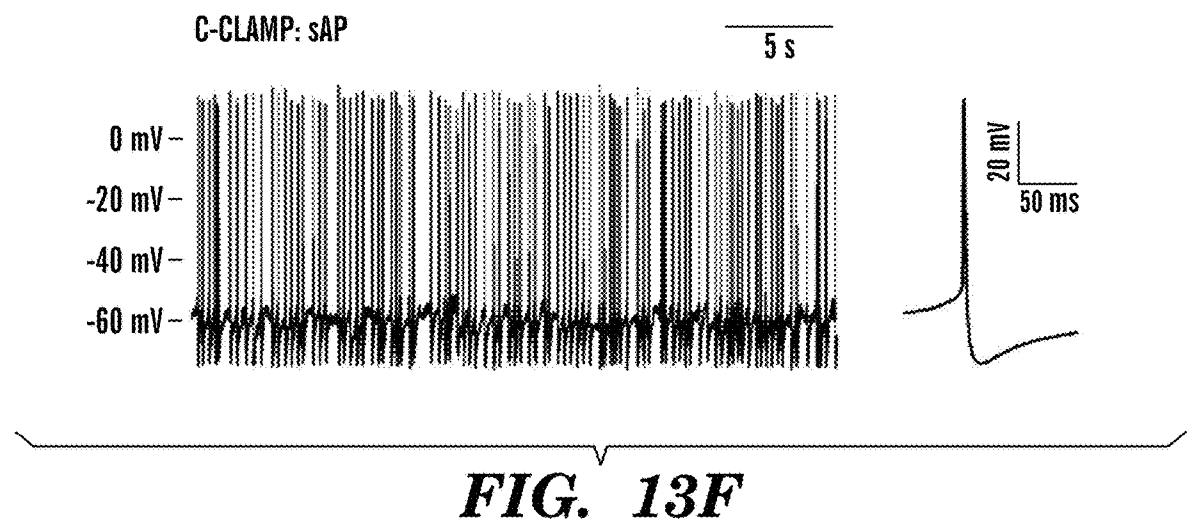
Figure 13G:
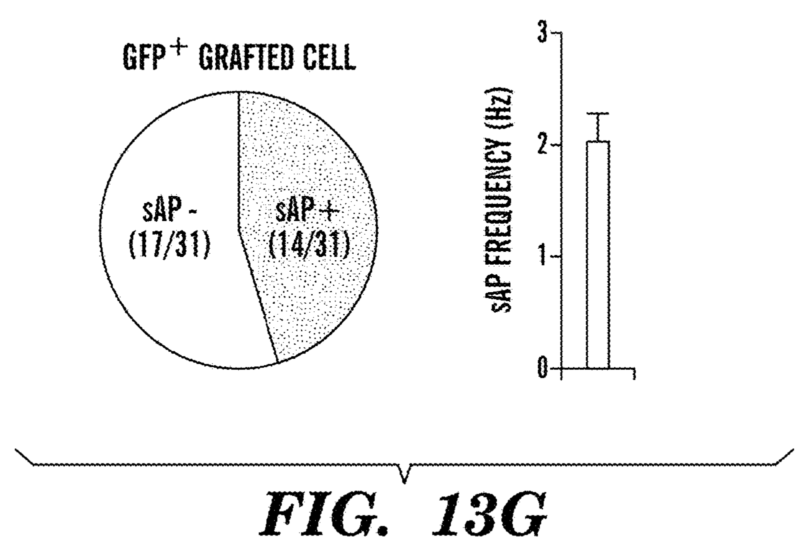
Figure 14A:
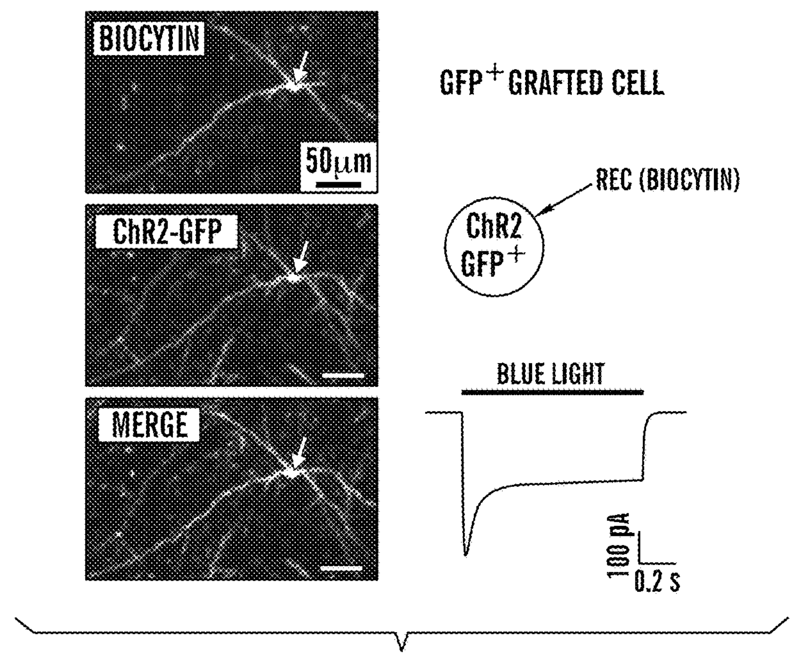
FIGS. 14*a* to 14*g*. Transplanted human MGE cells differentiate into GABAergic interneurons in the epileptic hippocampus.
Figure 14B:
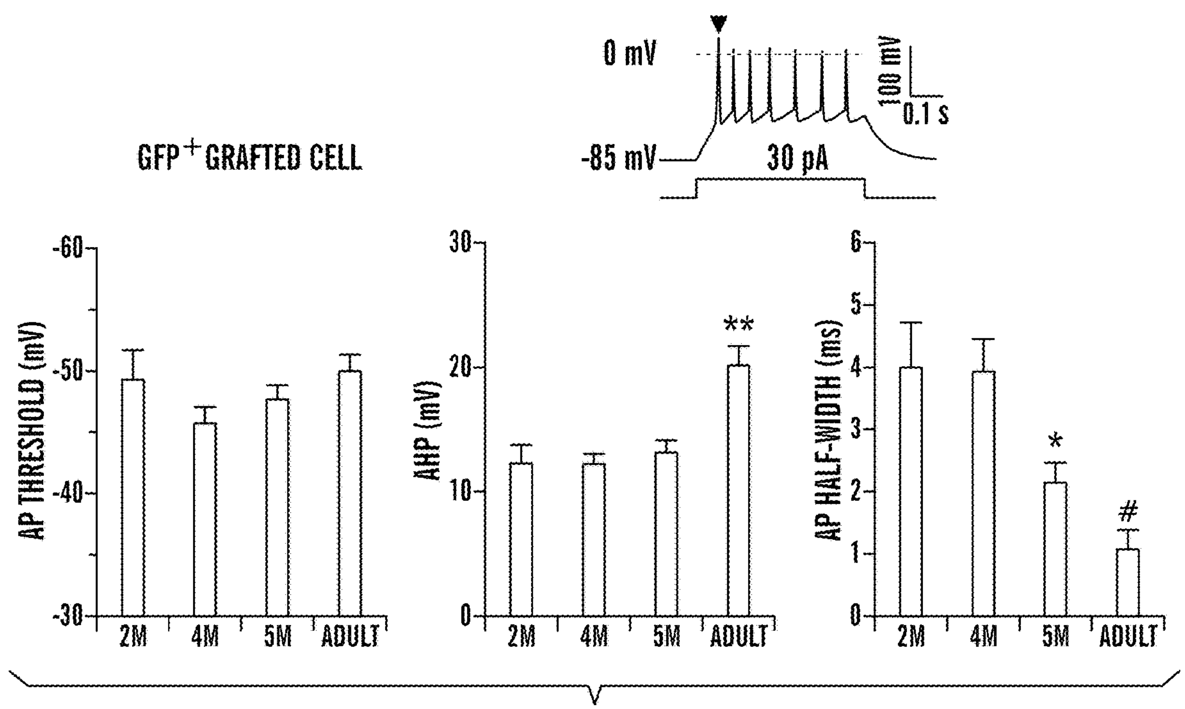
Figure 14C:
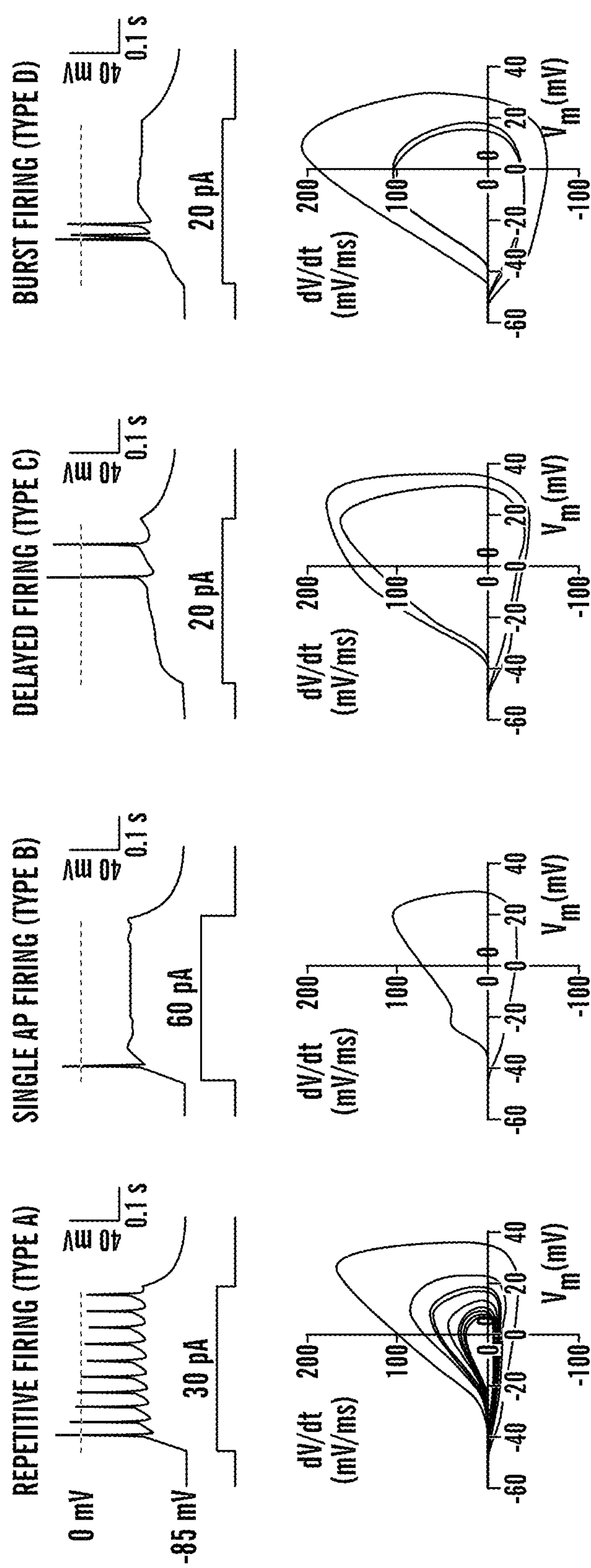

Electrophysiological and morphological analyses were used to determine whether transplanted human MGE cells develop into functional GABAergic neurons and integrate into host neural circuitry. Human MGE cells, transduced with lentivirus to stably express channelrhodopsin-2 (ChR2) (H134R)-GFP fusion under a synapsin promoter, were transplanted into the hippocampus of TLE mice. Two to five months after transplantation, grafted human MGE-derived cells were identified with green fluorescence in acute brain slices containing the hippocampus (GFP+ cells, FIG. 13*a*). All 31 GFP+ cells displayed typical ChR2-mediated currents induced by blue light illumination (FIG. 13*b*), indicating that recorded GFP+ cells were indeed human MGE-derived cells expressing ChR2. Consistently, short pulses of blue light illumination evoked action potential (AP) firings in most GFP+ cells (FIG. 13*c*), suggesting that grafted GFP+ cells can be activated by photostimulation in brain slice preparations. Passive membrane properties of GFP+ human mGIN, including resting membrane potential (RMP) and membrane resistance (Rm), were similar to those reported previously (Nicholas et al., 2013) (FIG. 13*d*). Unlike the previous report, however, we did not observe an increasing trend of the membrane capacitance (Cm) of the grafted cells (FIG. 13*d*). This discrepancy may be due to the different experimental conditions that human MGE cells were transplanted into the brain in our study whereas they were grown in culture in the previous report. Thus, our findings reflect the membrane properties of human MGE cells under more physiological conditions. Compared to host hippocampal interneurons in adult mice, RMP was significantly depolarized in grafted mGIN ($p<0.001$), suggesting that grafted cells were not fully mature at this time point. However, there was no significant difference in Rm and Cm between human mGIN vs. host interneurons. When voltage pulses were applied, grafted human mGIN showed rapidly desensitizing inward currents activated at membrane potential >−40 mV (FIG. 3*e*), indicating the expression of voltage-gated Na+ channels. In current-clamp mode, 45% of human mGIN displayed spontaneous AP firings at resting membrane potential at 2.0±0.2 Hz (FIGS. 13*f* and 13*g*), suggesting that some of the grafted mGIN generate tonic firings. Furthermore, the injection of depolarizing currents induced AP firings in all human mGIN examined (FIGS. 14*a* and 14*b*). As for passive membrane properties, grafted mGIN displayed less mature biophysical properties of AP firings compared to the host interneurons in terms of after-hyperpolarization and AP width (FIG. 14*b*), consistent with their well-known protracted maturation (Nicholas et al., 2013), whereas there was no significant difference in AP threshold. When grouped based on AP firing, most human mGIN displayed repetitive (type A, 52%) or single AP firing (type B, 32%) whereas delayed (13%) or burst firing pattern (3%) was also observed in a small proportion of transplanted cells (FIG. 14*c*). Furthermore, while more frequent AP firings were induced by small current injections (<50 pA) in repetitive-firing type A cells, type B cells generated only 1-3 AP firings induced by much larger current injections (>50 pA, FIG. 14*e*). As expected, Rm was significantly larger in type A cells than in type B cells (FIG. 14*e*), accounting for different firing patterns of these cells.

Figure 14D:
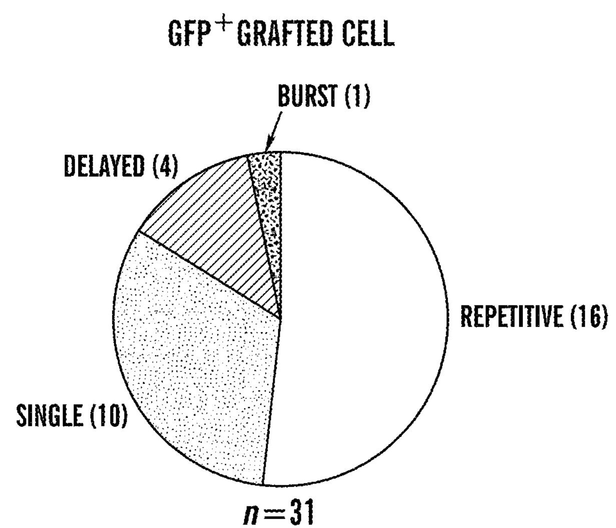
Figure 14E:
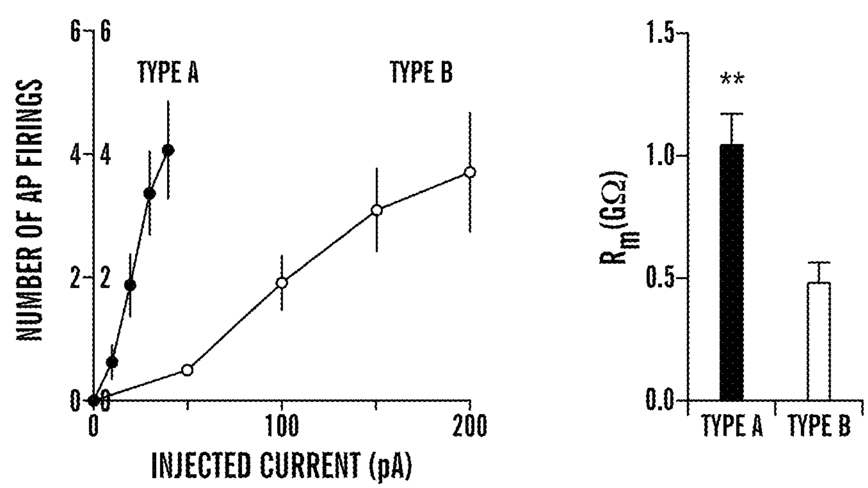
Figure 14F:
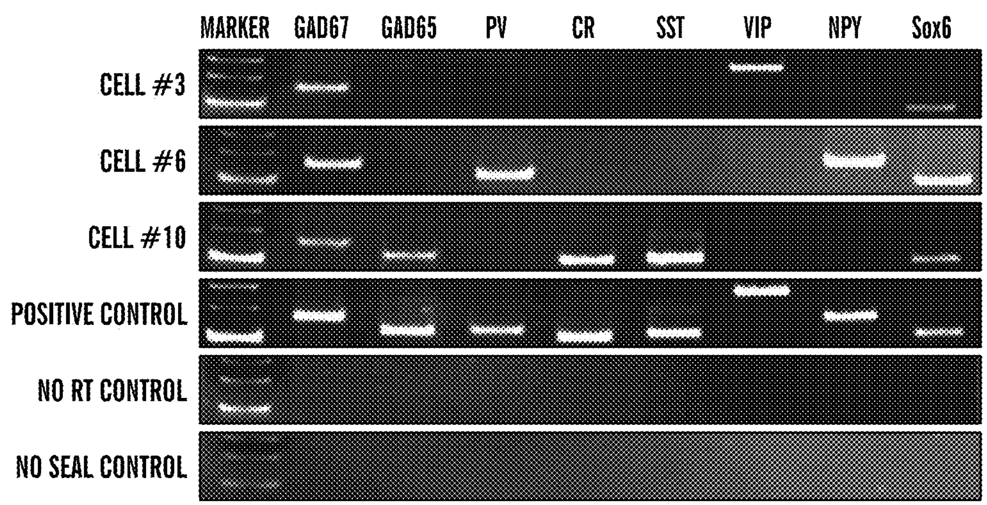
Figure 14G:
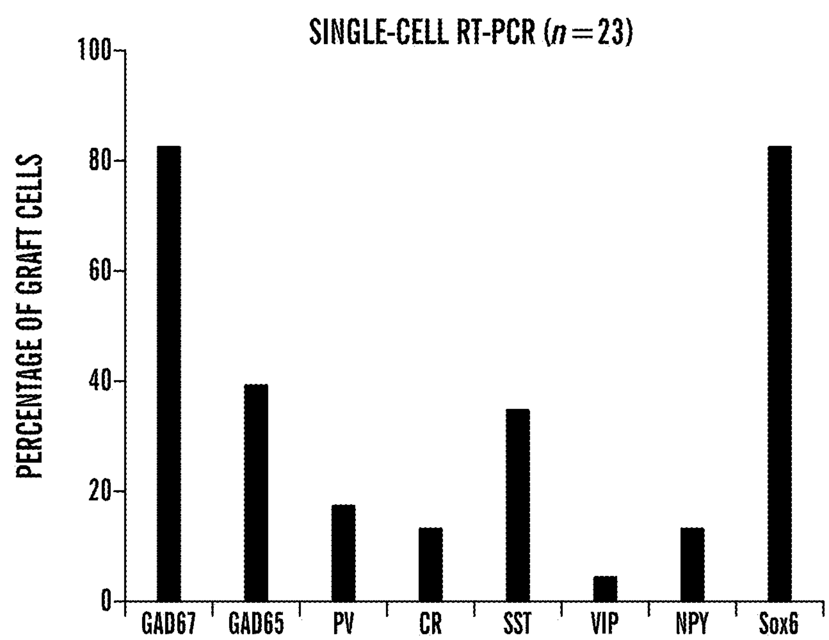

After recording, we collected the intracellular contents of the recorded cells and performed single-cell RT-PCR to examine the RNA profile of transplanted human mGIN (FIG. 140. Most grafted cells expressed glutamate decarboxylase (GAD) and Sox6 while some grafted cells also expressed other GABAergic neuronal markers including parvalbumin, calreticulin, somatostatin, vasoactive intestinal peptide, and neuropeptide Y (FIG. 14*g*). We also performed morphological analysis with biocytin-labeled human mGIN and found characteristic neuronal morphologies with various patterns of neuronal processes and RNA profile of GAD67; GAD65; parvalbumin; calreticulin; somatostatin; vasoactive intestinal peptide, neuropeptide Y; and or Sox6 was determined. Our results demonstrate that transplanted human MGE cells develop into mGIN with diverse electrophysiological, biochemical and morphological properties in the epileptic hippocampus.

Figure 15A:
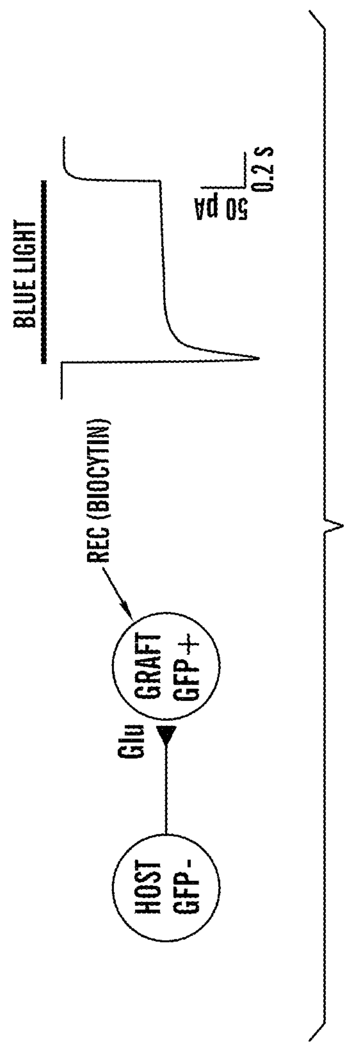
FIGS. 15*a* to 15*g*. Transplanted human mGIN receive glutamatergic inputs from host neurons. Images of human mGIN transplanted into the hippocampus were taken. The ChR2/GFP-expressing grafted cell was labeled with biocytin using a recording patch pipette. Grafted human mGIN were recorded in acute brain slices. Grafted cells, identified with green fluorescence, receive synaptic inputs from host neurons. The recorded cell was labeled with biocytin-streptavidin using patch pipettes.
Figure 15C:
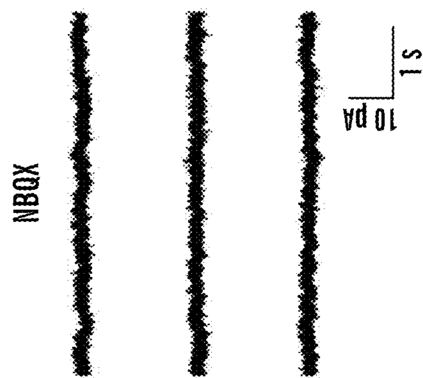
Figure 15B:
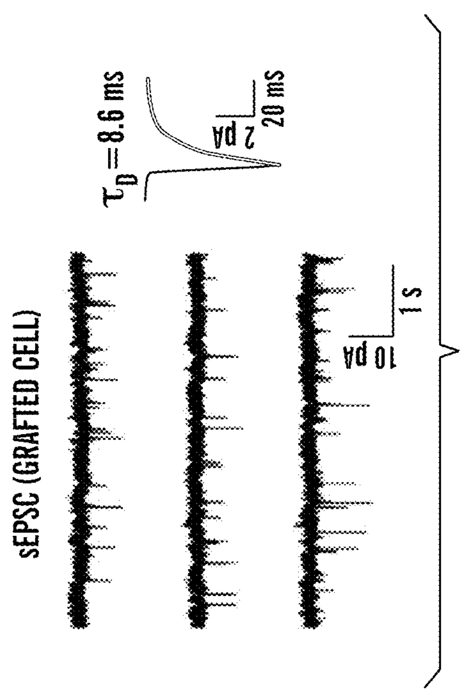
Figure 15D:
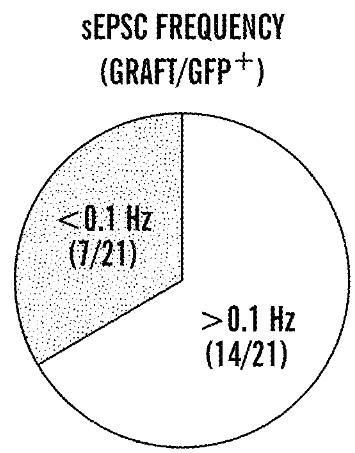
Figure 15E:
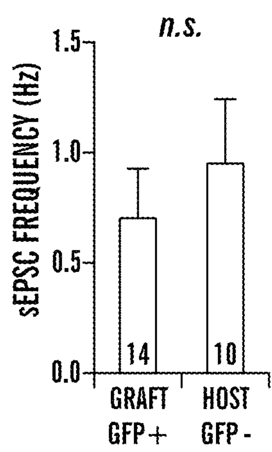
Figure 15F:
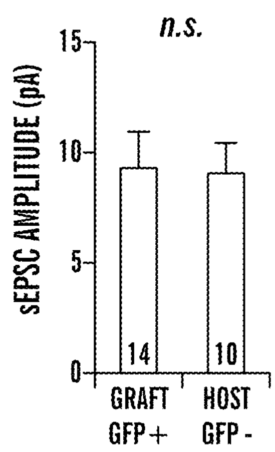
Figure 15G:
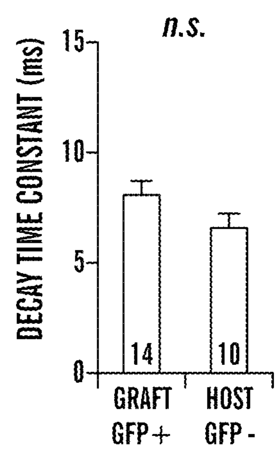

We then investigated whether grafted human mGIN possessed functional postsynaptic mechanisms allowing synaptic transmission from host neurons. Using confocal microscopic imaging, we observed postsynaptic dendritic spines in biocytin-labeled grafted cells, suggesting that they may receive excitatory synaptic inputs (FIG. 15*b*). Consistently, in acute hippocampal slices, two thirds of 21 GFP+ mGIN showed spontaneous postsynaptic currents at −85 mV in voltage-clamp mode at a frequency >0.1 Hz (FIG. 15*b* and FIG. 15*b*). Moreover, these currents were inhibited completely by NBQX, an AMPA/kainite-type glutamate receptor antagonist (FIG. 15C), indicating that they were mediated by excitatory neurotransmitter glutamate. There were no significant differences in biophysical properties of spontaneous postsynaptic activities between grafted human mGIN and host hippocampal interneurons (FIGS. 15*e* to 15*g*, and data not shown). These results suggest that most human mGIN transplanted into the hippocampus, have functional postsynaptic machinery, receiving excitatory synaptic inputs from host glutamatergic neurons. Immunocytochemistry analysis also showed that many postsynaptic PSD95+ puncta on GFP+ grafted cells were juxtaposed with presynaptic synaptophysin puncta (data not shown, 2.18±0.56 PSD95+ puncta/10 μm GFP+ dendrite (n=22 dendrite segments)), suggesting the formation of host glutamatergic synapses onto transplanted human mGIN. Further confirmation of functional synapse formation between host and transplanted neurons was obtained from ultrastructural analysis by Transmission Electron Microscopy (TEM). Examination of hippocampal areas in brain slices immunostained with diaminobenzidine (DAB) for human cytoplasm (human cytoplasm+) showed excitatory synaptic connections with host neurons (data not shown). These combined electrophysiological and ultrastructural data demonstrate functional synaptic integration of grafted mGIN into host parenchyma.

Activation of human mGIN induces GABA-mediated inhibitory postsynaptic responses in host hippocampal neurons.

Figure 16A:
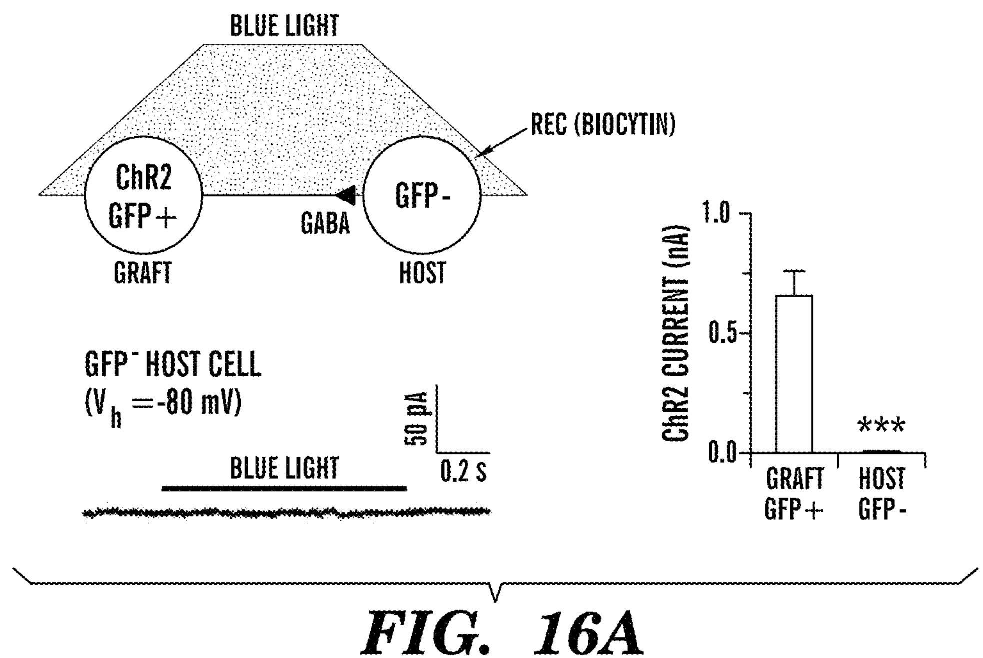
FIGS. 16*a* to 16*h*. Optogenetic stimulations of transplanted human mGIN induce GABAergic postsynaptic responses in host hippocampal neurons. Microscopic images were taken showing both a GFP+ grafted human MGE cell and a GFP-host pyramidal neuron in the CA3 of the hippocampus (Data not shown). These cells were labeled with biocytin-Streptavidin using recording pipettes (red). The grafted cell sends out projections towards the host pyramidal neuron. Microscopic images showed the soma and dendrites of the same GFP-pyramidal neuron as in the left image. Projections from grafted human mGIN are shown in the middle panel were observed (green, ChR2-GFP, data not shown).
Figure 16B:
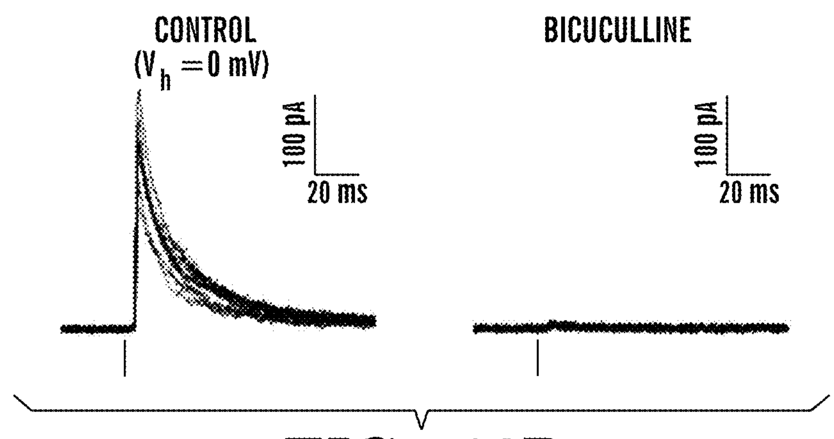
Figure 16C:
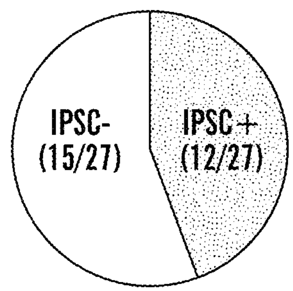
Figure 16C:
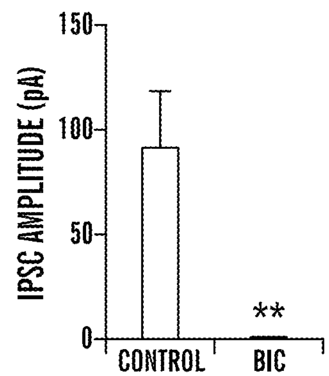
Figure 16C:
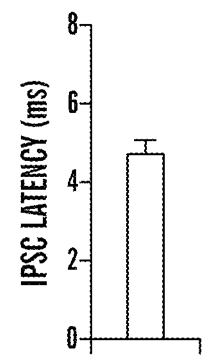
Figure 16D:
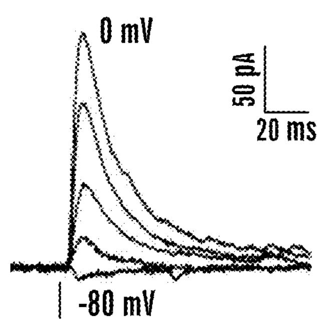
Figure 16D:
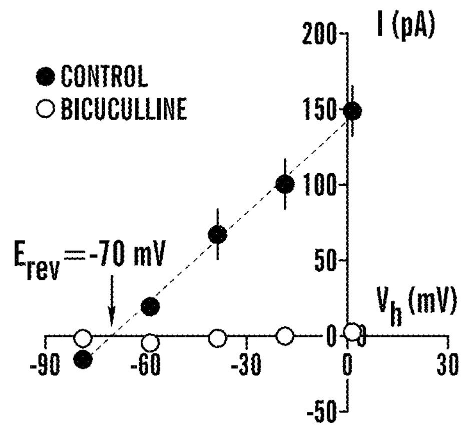
Figure 16E:
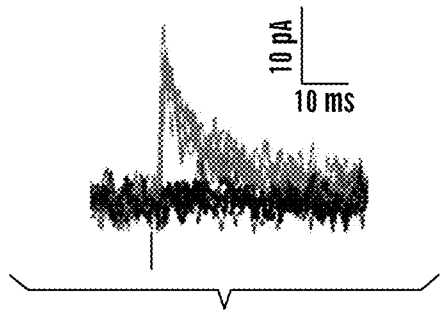
Figure 16F:
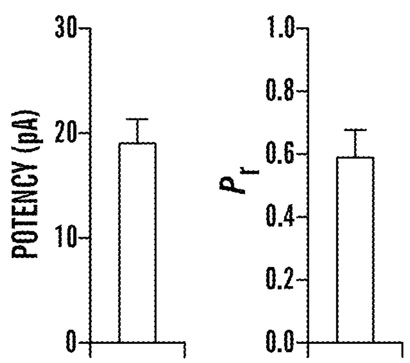
Figure 16G:
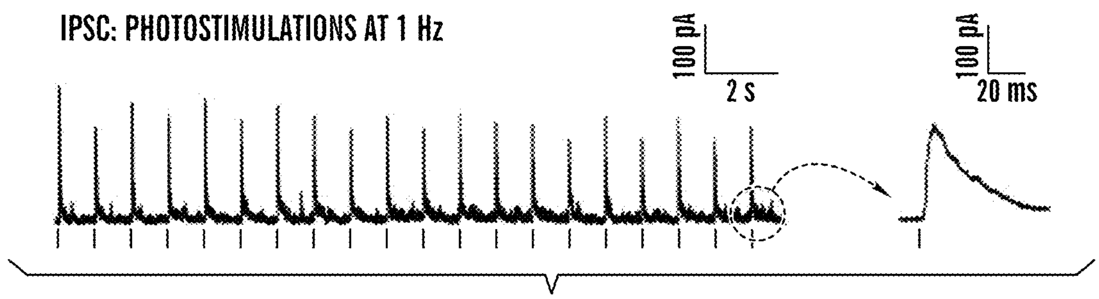
Figure 16H:
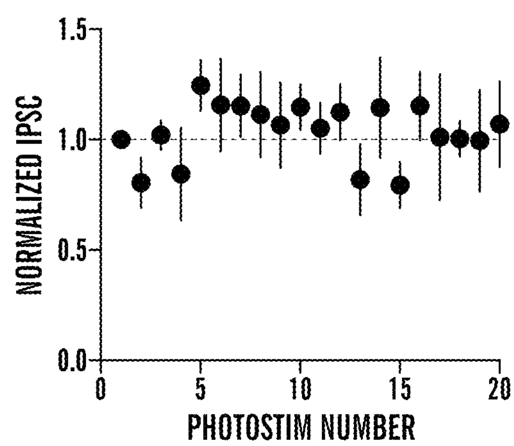
Figure 17A:
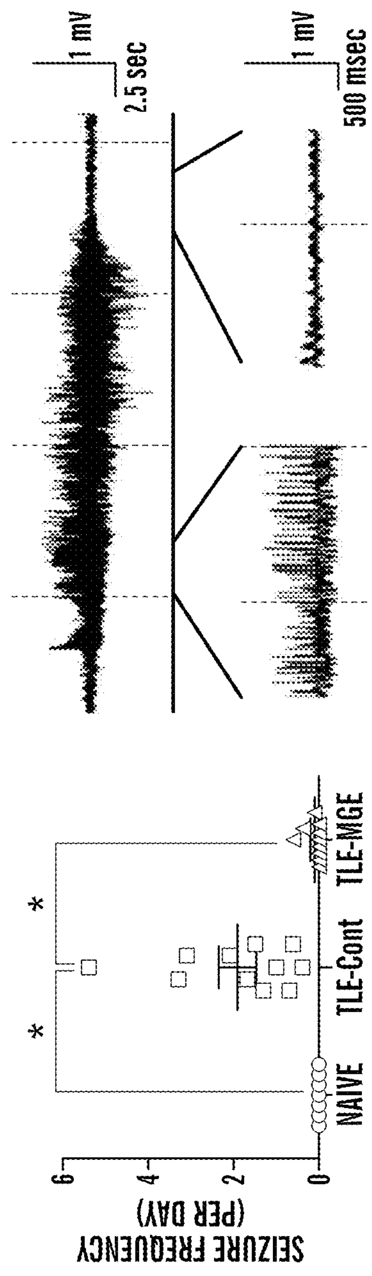
Figure 17B:
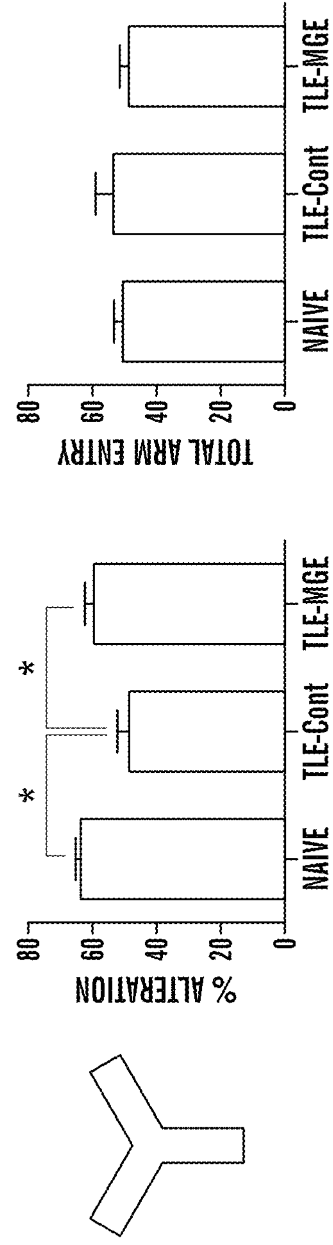
Figure 17C:
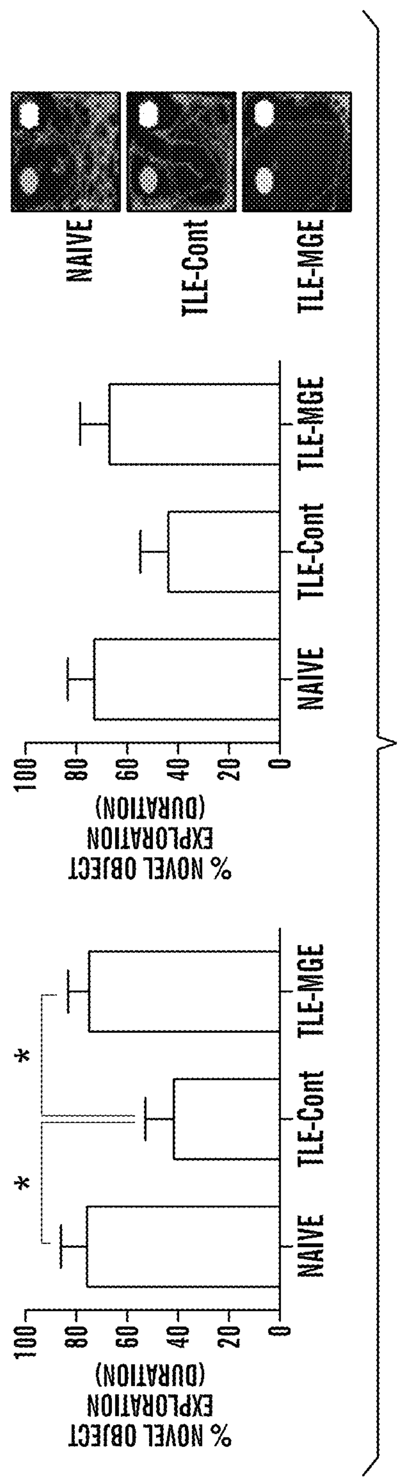
Figure 17D:
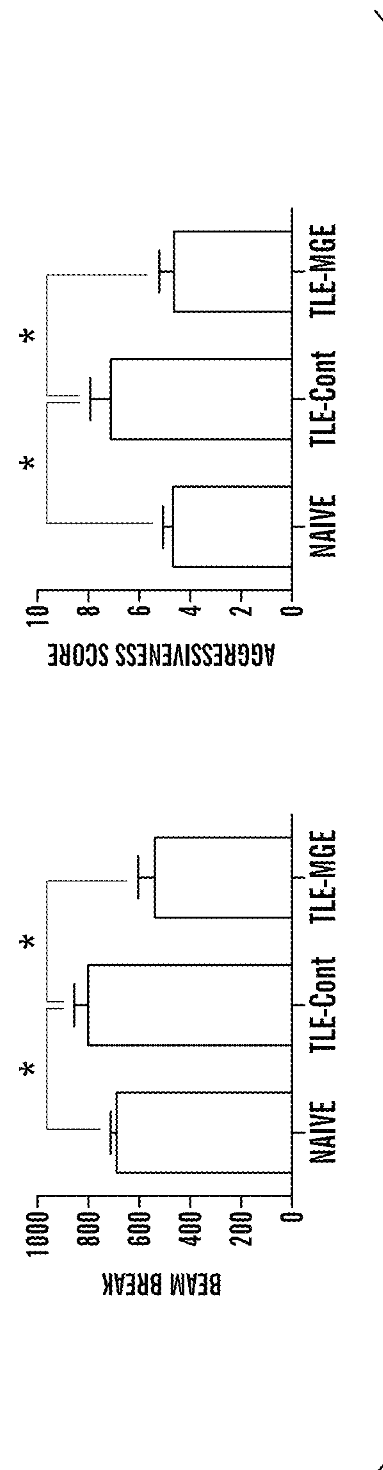

We next investigated whether grafted human mGIN also have functional presynaptic machinery to release GABA and induce inhibitory postsynaptic responses in host hippocampal neurons (FIG. 16*a*). To this end, we used optogenetic approaches to selectively stimulate ChR2-expressing transplanted cells in hippocampal slices (FIG. 16*c*). Blue light illumination induced ChR2-mediated inward current and AP firings in GFP+ grafted cells (FIG. 13*c*), whereas the same photostimulation did not induce such currents in any GFP− cells tested (FIG. 16*c*), suggesting that grafted cells can be selectively activated in acute brain slices with this approach. Under these conditions, short pulses of photostimulation, activating ChR2-expressing grafted cells, induced postsynaptic responses in 44% of total 27 GFP+ cells (FIGS. 16*b* and 16*c*). The recorded postsynaptic currents showed a short synaptic delay, indicating monosynaptic origin (Cho et al., 2013). Furthermore, these synaptic responses were inhibited completely by bicuculline, a GABAA receptor antagonist (FIGS. 16*b* and 16*c*), suggesting that they were mediated by inhibitory neurotransmitter GABA. The current-voltage relationship revealed the reversal potential of these currents at −70±3 mV (FIG. 16*d*), consistent with the estimated reversal potential of chloride ion (−65 mV under our experimental conditions). In some GFP− cells, photostimulation induced probabilistic quantal responses (FIGS. 16*e* and 16*f*), confirming their synaptic nature. Moreover, train photostimulation at 1 Hz induced postsynaptic responses without significant reduction in peak amplitude (FIGS. 16*g* and 16*h*), suggesting that the repetitive activation of grafted mGIN can consistently induce GABAergic responses in GFP− cells. Considering that grafted cells constitutes 30.7+4.7% of total cells at the graft core, where the density of GFP+ cells is highest, the majority of the recorded GFP− cells would be host hippocampal neurons. Thus, our results suggest that the activation of transplanted human MGE-derived cells can generate inhibitory postsynaptic responses in host hippocampal neurons. Imaging studies provided further evidence for the formation of inhibitory synaptic connections onto host neurons by transplanted human mGIN. Fluorescence microscopy showed that many of the presynaptic VGAT+ puncta on GFP+ mGIN were juxtaposed with postsynaptic Gephyrin+ puncta (data not shown). TEM ultrastructural studies also identified symmetric synaptic contacts between presynaptic grafted cells and postsynaptic host neurons (data not shown). Taken together, these results suggest that grafted human mGIN have presynaptic machinery to release GABA and inhibit host hippocampal neurons as well as postsynaptic machinery to receive excitatory inputs from host neurons, being well integrated into the host hippocampal circuitry and regulating host inhibitory balance.

Transplanted maturing human GABAergic interneurons reduce seizure activity in epileptic mice and ameliorate behavioral abnormalities.

Our electrophysiological findings suggest that transplanted human MGE cells integrate into host hippocampal circuitry and may be sufficient to exert anti-epileptic effects by releasing inhibitory neurotransmitter GABA and suppressing hippocampal activity. Therefore, we next investigated the therapeutic potential of transplanted human MGE cells for preventing seizures in our TLE mouse model. Seizure activity of engrafted TLE mice was analyzed 3 months after transplantation by continuous EEG-video monitoring. Vehicle-injected control TLE mice with sham surgery (n=11) showed seizure EEG activity with high-frequency, high-voltage synchronized polyspikes (FIG. 14*a*), having a seizure event frequency of 1.92±0.45 seizures/day. mGIN-grafted TLE mice (n=9), however, showed significantly reduced seizure event frequency of 0.13±0.07 seizure/day; in five animals in this group, seizure activity was eliminated entirely (FIG. 14*a*). Seizure EEG activity was confirmed by simultaneous video recording, which showed clonus and rearing and falling of the mice (Racine stage 3-5; Video. S1). Naïve Nod-Scid mice without pilocarpine injection did not show any seizure EEG activity during the monitoring (n=6). The duration of seizures was not significantly different between control TLE mice and mGIN-grafted TLE mice (39±2.7 sec vs. 42.8±8.7 sec, n=4-10, p=0.6083).

Because epilepsy patients frequently suffer from comorbid cognitive impairment and psychiatric symptoms (Brooks-Kayal et al., 2013), we analyzed the effect of human mGIN transplantation on various behaviors of TLE mice. Previous studies have shown that these animals, similar to TLE patients, show cognitive deficits (Groticke et al., 2007), which could be reversed by engrafting mouse embryonic MGE cells (Hunt et al., 2013). Therefore, for the present experiments we tested whether transplanted mGIN can affect cognitive function of TLE mice in a similar manner. Using a Y maze memory task, TLE mice (n=10) showed significant deficits in short-term working memory compared to naïve mice (n=9). This deficit was dramatically reduced after mGIN transplantation (n=8); there was no significant difference in total arm entry among test groups (FIG. 14*b*). As an independent measure of learning and memory, a novel object recognition test was performed. One hour after a 3-minute training session using 2 identical objects, one of the objects was replaced with a novel object, and the time spent to explore the novel object, expressed as the percentage of the total time spent to explore either object, was analyzed. Vehicle-injected control TLE mice (n=11) showed significantly decreased time exploring the novel object compared to the naïve mice (n=8), whereas this deficit was reversed after mGIN transplantation (n=8; FIG. 14*c*). The percentage of the number of visits (frequency) to the novel object compared to total number of visits to either object showed a similar trend, though it did not reach significance.

In addition to cognitive deficits, hyperactivity and aggressiveness have been reported in the pilocarpine-induced rodent model of TLE (Muller et al., 2009; Rice et al., 1998). The present experiments demonstrated that control TLE mice (n=11) displayed significantly higher locomotor activity compared to the naïve mice (n=14) as measured using a photobeam activity system. Animals engrafted with human mGIN demonstrated a significant attenuation of this abnormality (n=8; FIG. 14*d*). Pilocarpine-induced TLE mice also showed increased agitation and aggressive behavior even during routine handling. The hypervigilance and aggressiveness displayed by vehicle-injected control TLE mice (n=11) was normalized to levels comparable to naïve mice (n=15) after transplantation (FIG. 14*e* and data not shown).

While fetal MGE cell transplantation has demonstrated proof-of-principle for cell-based therapy of epilepsy (Hattiangady et al., 2008; Hunt et al., 2013), clinical application is limited by the lack of standardized and reliable cell sources as well as ethical controversies associated with using fetal cells. Human PSC technology offers the potential to provide cell sources that are well-characterized, quality-controlled, and virtually unlimited in supply, as long as efficacious progenies can be proficiently derived. We have utilized optimized differentiation of human PSCs into MGE cells (Kim et al., 2014), and report here previously unknown functional efficacy of mGIN to reduce epileptic activity and comorbid behavioral abnormalities in the epileptic brain even before they attain full maturity. Considering full electrophysiological maturation of human GABAergic interneurons could take years (Le Magueresse and Monyer, 2013; Nicholas et al., 2013), our findings using human mGIN provide a major step towards developing an efficient and novel cell-based therapy for treating intractable epilepsy.

Figure 20:
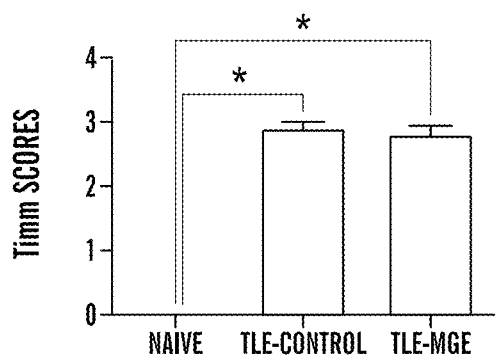
FIG. 20 shows a graph indicating that mGIN transplantation does not affect Mossy fiber sprouting. Hippocampal brain sections from naïve Nod-Scid mice, TLE control mice and transplanted TLE mice were stained using anti-ZnT3 antibody, to analyze mossy fiber sprouting. Quantification of Mossy fiber sprouting (n=7).
Figure 21:
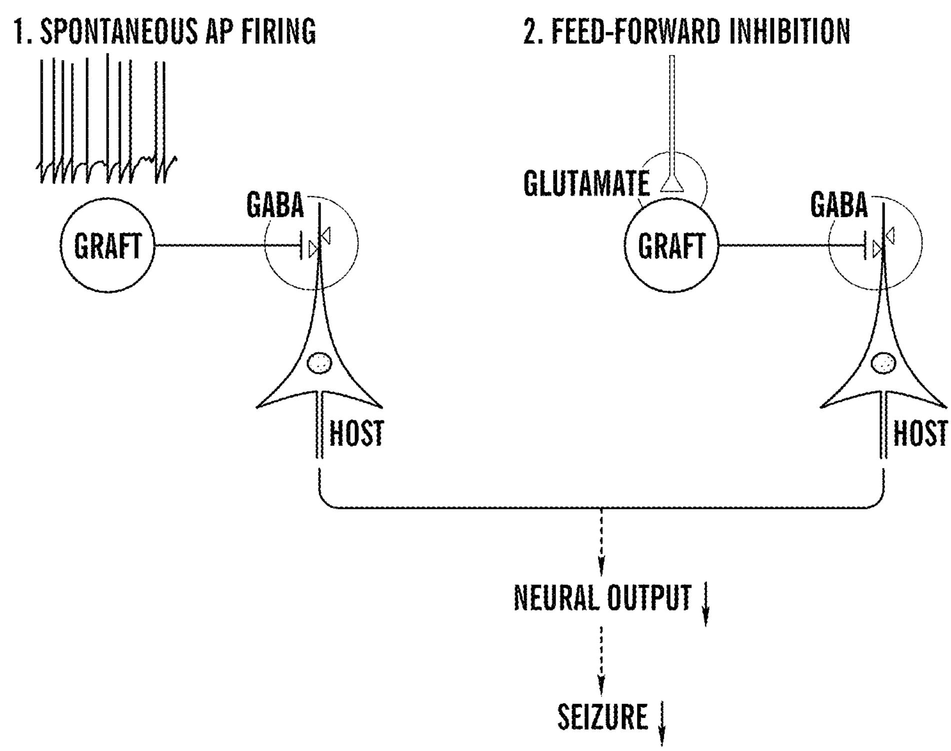
FIG. 21 shows a schematic of the mechanisms of anti-epileptic effects of transplanted human PSC-derived mGIN. Transplanted human mGIN (graft) fire action potentials (AP) spontaneously (1) and receive excitatory synaptic inputs from host glutamatergic neurons (2). Grafted human mGIN release inhibitory neurotransmitter GABA in an activity-dependent manner. Therefore, the activation of transplanted mGIN, either by spontaneous activity or by excitatory synaptic drive, increases inhibitory synaptic responses in host hippocampal neurons (host), suppressing exaggerated neural activity in the epileptic brain.

We have demonstrated that PSC-derived human mGIN migrate extensively within the epileptic hippocampus, integrate into host circuitry and reduces seizure activity and other behavioral abnormalities. The primary mechanisms of the functional effects of grafted mGIN are suggested by our electrophysiological studies (FIG. 21). Although they are not fully mature, approximately half of transplanted human MGE cells fire spontaneous action potentials (AP) at ~2 Hz, indicating that they are tonically active even without extrinsic synaptic inputs. Moreover, transplanted human mGIN fully integrate into the hippocampal circuitry, receiving excitatory synaptic inputs from host glutamatergic neurons and therefore activated by host signals. In turn, our optogenetic studies revealed that grafted human mGIN release inhibitory neurotransmitter GABA in an activity-dependent manner. Therefore, the activation of transplanted mGIN, either by spontaneous activity or by excitatory synaptic drive, would increase inhibitory synaptic responses in host hippocampal neurons, shifting excitation toward inhibition and suppressing exaggerated neural activity in the epileptic brain. Consistent with previous work (Hunt et al., 2013), we did not observe significant changes in mossy fiber sprouting by human MGE transplantation compared to control TLE mice (FIG. 20), suggesting that regulation of inhibitory balance by grafted cells may be sufficient to exert the anti-epileptic effects observed in this study.

Cell therapy for epilepsy offers a number of advantages over conventional therapies. Distinct cell types can be precisely engrafted into brain substructures (Bjarkam et al., 2010), averting the acute and long-term systemic adverse effects seen with AEDs. Further, neural grafts, with their ability to integrate within the host circuitry, would circumvent the need for daily dosing and sluggish titration required with AED administration. A self-regulating therapeutic system of mGIN grafts would eliminate the need of carrying devices to monitor and control seizures. Temporal lobectomy has been used as a last-resort intervention for intractable epilepsy, but is associated with surgical morbidity and permanent dysfunction. High-precision stereotactic engraftment of stem cells, however, is less invasive and leaves functional neural tissue undisturbed.

Here we have demonstrated the biology and utility of human PSC-derived mGIN to ameliorate the symptoms of a prevalent and debilitating neuropsychiatric disease. Before transition into the clinic setting, the question of 'dosing' of MGE cell grafts will need to be addressed. Interestingly, it has been reported that an increase in inhibition reaches a plateau with relatively low numbers of transplanted interneurons (Southwell et al., 2010). This suggests that larger numbers of interneurons are unlikely to result in adverse effects, but at the same time, smaller, less intrusive deposits of cells may produce an optimal response. In addition, further evaluation of long-term graft survival and safety should be assessed before undertaking clinical applications. Porcine human simulation neurosurgery is presently underway to establish such criteria prior to human trials (Cunningham et al., unpublished data). In addition, isolation and purification of cortical interneuron populations using appropriate cell surface markers will facilitate the generation of quality-controlled cell sources for human trials. With prudent preclinical testing, this technology holds promise as a therapeutic approach for TLE as well as other intractable diseases of the central nervous system.

TABLE 2

Antibody list used in the experiments for Example 2.

| Antibody | Species | Dilution | Source |
|---|---|---|---|
| β-tubulin | Rabbit | 1/2000 | Covance |
| β-tubulin | Mouse | 1/2000 | Covance |
| Calbindin | Rabbit | 1/10000 | Swant |
| Calretinin | Goat | 1/5000 | Swant |
| GABA | Rabbit | 1/1000 | Sigma |
| Lhx6 | Rabbit | 1/1000 | Gift from Dr. Pachnis |
| NCAM | Mouse | 1/1000 | SCBT |
| Nestin | Mouse | 1/1000 | Millipore |
| Neuropeptide Y | Sheep | 1/5000 | Millipore |
| Nkx2.1 (TTF1) | Rabbit | 1/2000 | Epitomics |
| Human Nucleus | Mouse | 1/1000 | Millipore |
| Olig2 | Rabbit | 1/500 | Millipore |
| Parvalbumin | Mouse | 1/5000 | Millipore |
| PSD-95 | Rabbit | 1/1000 | Cell Signaling |
| PSD-95 | Mouse | 1/1000 | Neuro Mab |
| Somatostatin | Rat | 1/5000 | Millipore |
| Synaptophysin | Rabbit | 1/2000 | Pierce |
| Synaptophysin | Mouse | 1/500 | Abcam |
| ENCAM | Rat | 1/1000 | BD |
| NeuN | Mouse | 1/500 | Chemicon |
| VGAT | Rabbit | 1/1000 | Synaptic Systems |
| Gephyrin | Mouse | 1/1000 | Synaptic Systems |
| Human Cytoplasm | Mouse | 1/500 | Stem Cells Inc |
| Ki67 | Mouse | 1/1000 | Millipore |
| Sox6 | Rabbit | 1/1000 | Millipore |
| Somatostatin | Goat | 1/1000 | SCBT |
| GFAP | Rabbit | 1/1000 | Dako |
| CoupTFII | Mouse | 1/1000 | Persus Proteomics |
| SSEA4 | Mouse | 1/1000 | SCBT |
| Cy3-Human Nucleus | Mouse | 1/1000 | Millipore |
| ZnT3 | Rabbit | 1/1000 | Gift from Dr. Palmiter |
| VIP | Rabbit | 1/1000 | ImmunoStar |

TABLE 3

Primer list of Example 2.

| Outside primers | | |
|---|---|---|
| GAD67 | Forward | ATACCTCTTCCAGCCAGAC (SEQ ID NO: 2) |
| | Reverse | GCTCGCCATTGAAAACCATC (SEQ ID NO: 3) |
| Parvalbumin | Forward | ACCTGTCTGCTAAAGAAACC (SEQ ID NO: 4) |
| | Reverse | GGGGATGGGGGAGTAAAAAATAAC (SEQ ID NO: 5) |

TABLE 3-continued

| Primer list of Example 2. | | |
|---|---|---|
| Somatostatin | Forward | CAACCAGACGGAGAATGATG (SEQ ID NO: 6) |
| | Reverse | GCTGAAGACTTGGAGGATTAG (SEQ ID NO: 7) |
| Neuropeptide Y | Forward | TAGGTAACAAGCGACTGGGG (SEQ ID NO: 8) |
| | Reverse | GGGCTGAAAATAGGAAAAGGC (SEQ ID NO: 9) |
| Calretinin | Forward | AAGGCAAGGAAAGGCTCTGG (SEQ ID NO: 10) |
| | Reverse | CCGTTCAAGTCAAACATCCG (SEQ ID NO: 11) |
| Vasoactive intestinal peptide | Forward | TCTTCTCACAGACTTCGGC (SEQ ID NO: 12) |
| | Reverse | CATTTGTTTTCTAAGGCGGG (SEQ ID NO: 13) |
| Sox6 | | ATACAAACCCCGACCGAAACGCAC (SEQ ID NO: 14) |
| | Reverse | CCGCCATCTGTCTTCATAC (SEQ ID NO: 15) |
| GAD65 | Forward | AACACCACTTTGTCTCTGAG (SEQ ID NO: 16) |
| | Reverse | GGTAGTTTGGCACACCTAAC (SEQ ID NO: 17) |
| Nested primers | | |
| GAD67 | Forward | GCAGTATGATGTCTCCTACG (SEQ ID NO: 18) |
| | Reverse | GTATTCAGCCAGTTCCAGG (SEQ ID NO: 19) |
| Parvalbumin | Forward | TGCTGGAGACAAAGATGGGGAC (SEQ ID NO: 20) |
| | Reverse | ATTGGGTGTTCAGGGCAGAGAG (SEQ ID NO: 21) |
| Somatostatin | Forward | GCAGGATGAAATGAGGCTTG (SEQ ID NO: 22) |
| Reverse | | CAGGATGTGAAAGTCTTCCAG (SEQ ID NO: 23) |
| Neuropeptide Y | Forward | GCTGCGACACTACATCAAC (SEQ ID NO: 24) |
| Reverse | | CTCATTTCCCATCACCACATTG (SEQ ID NO: 25) |
| Calretinin | Forward | TCCTGCCAACCGAAGAGAAC (SEQ ID NO: 26) |
| | Reverse | TAGCCACTCCTGTCTGTGTC (SEQ ID NO: 27) |
| Vasoactive intestinal peptide | Forward | CTCTTTACAGGGCACCTTC (SEQ ID NO: 28) |
| | Reverse | GGTCTTCTGAGATGTTACTGC (SEQ ID NO: 29) |
| Sox6 | Forward | AGCAACTGATGAGGTCTCG (SEQ ID NO: 30) |
| | Reverse | CACCAGGATACACAACACC (SEQ ID NO: 31) |
| GAD65 | Forward | AAATCGTAGGTGTTGGCTC (SEQ ID NO: 32) |
| | Reverse | GATACCCAGTTTGAGGTTCC (SEQ ID NO: 33) |

REFERENCES EXAMPLE 2

Baraban, S. C., Southwell, D. G., Estrada, R. C., Jones, D. L., Sebe, J. Y., Alfaro-Cervello, C., Garcia-Verdugo, J. M., Rubenstein, J. L., and Alvarez-Buylla, A. (2009). Reduction of seizures by transplantation of cortical GABAergic interneuron precursors into Kv1.1 mutant mice. Proc Natl Acad Sci USA 106, 15472-15477.

Bjarkam, C. R., Glud, A. N., Margolin, L., Reinhart, K., Franklin, R., Deding, D., Ettrup, K. S., Fitting, L. M., Nielsen, M. S., Sorensen, J. C., et al. (2010). Safety and function of a new clinical intracerebral microinjection instrument for stem cells and therapeutics examined in the Gottingen minipig. Stereotactic and functional neurosurgery 88, 56-63.

Brooks-Kayal, A. R., Bath, K. G., Berg, A. T., Galanopoulou, A. S., Holmes, G. L., Jensen, F. E., Kanner, A. M., O'Brien, T. J., Whittemore, V. H., Winawer, M. R., et al. (2013). Issues related to symptomatic and disease-modifying treatments affecting cognitive and neuropsychiatric comorbidities of epilepsy. Epilepsia 54 Suppl 4, 44-60.

Chen, K. G., Mallon, B. S., McKay, R. D., and Robey, P. G. (2014). Human pluripotent stem cell culture: considerations for maintenance, expansion, and therapeutics. Cell Stem Cell 14, 13-26.

Christoph, C. H. (2008). Temporal lobe resection-does the prospect of seizure freedom outweigh the cognitive risks? Nat Clin Pract Neurol 4, 66-67.

Chung, S., Moon, J.-I., Leung, A., Aldrich, D., Lukianov, S., Kitayama, Y., Park, S., Li, Y., Bolshakov, V. Y., Lamonerie, T., et al. (2011). ES cell-derived renewable and functional midbrain dopaminergic progenitors. Proceedings of the National Academy of Sciences 108, 9703-9708.

Cossart, R., Dinocourt, C., Hirsch, J. C., Merchan-Perez, A., De Felipe, J., Ben-Ari, Y., Esclapez, M., and Bernard, C. (2001). Dendritic but not somatic GABAergic inhibition is decreased in experimental epilepsy. Nature neuroscience 4, 52-62.

Cramer, J. A., Mintzer, S., Wheless, J., and Mattson, R. H. (2010). Adverse effects of antiepileptic drugs: a brief overview of important issues. Expert Rev Neurother 10, 885-891.

Curia, G., Longo, D., Biagini, G., Jones, R. S., and Avoli, M. (2008). The pilocarpine model of temporal lobe epilepsy. J Neurosci Methods 172, 143-157.

de Lanerolle, N. C., Kim, J. H., Robbins, R. J., and Spencer, D. D. (1989). Hippocampal interneuron loss and plasticity in human temporal lobe epilepsy. Brain Res 495, 387-395.

Doischer, D., Hosp, J. A., Yanagawa, Y., Obata, K., Jonas, P., Vida, I., and Bartos, M. (2008). Postnatal differentiation of basket cells from slow to fast signaling devices. J Neurosci 28, 12956-12968.

Engel, J. (2001). A Proposed Diagnostic Scheme for People with Epileptic Seizures and with Epilepsy: Report of the ILAE Task Force on Classification and Terminology. Epilepsia 42, 796-803.

Engel, J. (2002). Epilepsy in the world today: medical point of view. Epilepsia 43 Suppl 6, 12-13.

Fine, A., Meldrum, B. S., and Patel, S. (1990). Modulation of experimentally induced epilepsy by intracerebral grafts of fetal GABAergic neurons. Neuropsychologia 28, 627-634.

Groticke, I., Hoffmann, K., and Loscher, W. (2007). Behavioral alterations in the pilocarpine model of temporal lobe epilepsy in mice. Exp Neurol 207, 329-349.

Hattiangady, B., Rao, M. S., and Shetty, A. K. (2008). Grafting of striatal precursor cells into hippocampus shortly after status epilepticus restrains chronic temporal lobe epilepsy. Exp Neurol 212, 468-481.

Hirsch, J. C., Agassandian, C., Merchan-Perez, A., Ben-Ari, Y., DeFelipe, J., Esclapez, M., and Bernard, C. (1999). Deficit of quantal release of GABA in experimental models of temporal lobe epilepsy. Nature neuroscience 2, 499-500.

Hunt, R. F., Girskis, K. M., Rubenstein, J. L., Alvarez-Buylla, A., and Baraban, S. C. (2013). GABA progenitors grafted into the adult epileptic brain control seizures and abnormal behavior. Nature neuroscience 16, 692-697.

Jensen, F. E. (2014). Epilepsy in 2013: Progress across the spectrum of epilepsy research. Nat Rev Neurol 10, 63-64.

Kim, T.-G., Yao, R., Monnell, T., Cho, J.-H., Vasudevan, A., Koh, A., Peeyush, K. T., Moon, M., Datta, D., Bolshakov, V. Y., et al. (2014). Efficient Specification of Interneurons from Human Pluripotent Stem Cells by Dorsoventral and Rostrocaudal Modulation. STEM CELLS 32, 1789-1804.

Kobayashi, M., and Buckmaster, P. S. (2003). Reduced inhibition of dentate granule cells in a model of temporal lobe epilepsy. J Neurosci 23, 2440-2452.

Le Magueresse, C., and Monyer, H. (2013). GABAergic Interneurons Shape the Functional Maturation of the Cortex. Neuron 77, 388-405.

Lindvall, O., and Bjorklund, A. (1992). Intracerebral grafting of inhibitory neurons. A new strategy for seizure suppression in the central nervous system. Advances in neurology 57, 561-569.

Loscher, W., Ebert, U., Lehmann, H., Rosenthal, C., and Nikkhah, G. (1998). Seizure suppression in kindling epilepsy by grafts of fetal GABAergic neurons in rat substantia nigra. J Neurosci Res 51, 196-209.

Maisano, X., Litvina, E., Tagliatela, S., Aaron, G. B., Grabel, L. B., and Naegele, J. R. (2012). Differentiation and functional incorporation of embryonic stem cell-derived GABAergic interneurons in the dentate gyrus of mice with temporal lobe epilepsy. J Neurosci 32, 46-61.

Mallon, B. S., Chenoweth, J. G., Johnson, K. R., Hamilton, R. S., Tesar, P. J., Yavatkar, A. S., Tyson, L. J., Park, K., Chen, K. G., Fann, Y. C., et al. (2013). StemCellDB: the human pluripotent stem cell database at the National Institutes of Health. Stem cell research 10, 57-66.

Marco, P., Sola, R. G., Pulido, P., Alijarde, M. T., Sanchez, A., Ramon y Cajal, S., and DeFelipe, J. (1996) Inhibitory neurons in the human epileptogenic temporal neocortex. An immunocytochemical study. Brain 119 (Pt 4), 1327-1347.

Mazzuferi, M., Kumar, G., Rospo, C., and Kaminski, R. M. (2012). Rapid epileptogenesis in the mouse pilocarpine model: video-EEG, pharmacokinetic and histopathological characterization. Exp Neurol 238, 156-167.

Muller, C. J., Groticke, I., Bankstahl, M., and Loscher, W. (2009). Behavioral and cognitive alterations, spontaneous seizures, and neuropathology developing after a pilocarpine-induced status epilepticus in C57BL/6 mice. Exp Neurol 219, 284-297.

Nicholas, C. R., Chen, J., Tang, Y., Southwell, D. G., Chalmers, N., Vogt, D., Arnold, C. M., Chen, Y. J., Stanley, E. G., Elefanty, A. G., et al. (2013). Functional Maturation of hPSC-Derived Forebrain Interneurons Requires an Extended Timeline and Mimics Human Neural Development. Cell Stem Cell 12, 573-586.

Okaty, B. W., Miller, M. N., Sugino, K., Hempel, C. M., and Nelson, S. B. (2009). Transcriptional and electrophysiological maturation of neocortical fast-spiking GABAergic interneurons. J Neurosci 29, 7040-7052.

Rice, A. C., Floyd, C. L., Lyeth, B. G., Hamm, R. J., and DeLorenzo, R. J. (1998). Status epilepticus causes long-term NMDA receptor-dependent behavioral changes and cognitive deficits. Epilepsia 39, 1148-1157.

Shibley, H., and Smith, B. N. (2002). Pilocarpine-induced status epilepticus results in mossy fiber sprouting and spontaneous seizures in C57BL/6 and CD-1 mice. Epilepsy Res 49, 109-120.

Southwell, D. G., Froemke, R. C., Alvarez-Buylla, A., Stryker, M. P., and Gandhi, S. P. (2010). Cortical plasticity induced by inhibitory neuron transplantation. Science (New York, N.Y.) 327, 1145-1148.

Spreafico, R., Battaglia, G., Arcelli, P., Andermann, F., Dubeau, F., Palmini, A., Olivier, A., Villemure, J. G., Tampieri, D., Avanzini, G., et al. (1998). Cortical dysplasia: an immunocytochemical study of three patients. Neurology 50, 27-36.

Walia, K. S., Khan, E. A., Ko, D. H., Raza, S. S., and Khan, Y. N. (2004). Side effects of antiepileptics—a review. Pain practice: the official journal of World Institute of Pain 4, 194-203.

Wieser, H. G. (2004). ILAE Commission Report. Mesial temporal lobe epilepsy with hippocampal sclerosis. Epilepsia 45, 695.

Yu, D. X., Marchetto, M. C., and Gage, F. H. (2013). Therapeutic translation of aspics for treating neurological disease. Cell Stem Cell 12, 678-688.

| Sequences |
|---|

FGF8 homosapiens protein (SEQ ID NO: 01)

```
  1 maedgdpfak livetdtfgs rvrvrgaetg lyicmnkkgk liaksngkgk dcvfteivle
 61 nnytalqnak yegwymaftr kgrprkgskt rqhqrevhfm krlprghhtt eqslrfefln
121 yppftrslrg sqrtwapepr
```

FGF8 *homosapiens* protein Nucleic acid: Human fibroblast growth factor 8 (FGF8) gene, exon 3 and complete cds. ACCESSION U47011

(SEQ ID NO: 43)

```
   1 ctcgagctcc ccacttcctg ggcttctggg gctggggtct tagcatcttc tcccaggcct
  61 cccctccccc ataggtggct gccctggggc cagggaaccg aagtcctggg ggggtgagag
 121 gggcaggtgg ggagacgggt ggccagactg gtgggcagga ggccagagca ggccaggctc
 181 tgggcccctc tctctgtctt tctgcgttgg ggcccagccc tccgtagaca accatgtgtc
 241 actgctgcct gggaaggaca ggaagttgcc gggtgggctg cgagttgtga gggattagag
 301 agcgggtgcc caggcagggg ggtggggctg cggctcctgc ccacctcgcc atctgctggg
 361 gtgcccacct gctgtctggg gccgctcgcc ctctgcctct gctggggggg ctctgtaacg
 421 tggtgtctgg ctcccctacc tgcagagcaa cggcaaaggc aaggactgcg tcttcacgga
 481 gattgtgctg gagaacaact acacagcgct gcagaatgcc aagtacgagg gctggtacat
 541 ggccttcacc cgcaagggcc ggccccgcaa gggctccaag acgcggcagc accagcgtga
 601 ggtccacttc atgaagcggc tgccccgggg ccaccacacc accgagcaga gcctgcgctt
 661 cgagttcctc aactacccgc ccttcacgcg cagcctgcgc ggcagccaga ggacttgggc
 721 ccccgagccc cgatagtgct gcctggccct ccccacaatg ccagaccgca gagaggctca
 781 tcctgtaggg cacccaaaac tcaagcaaga tgagctgtgc gctgctctgc aggctgggga
 841 ggtgctgggg gagccctggg ttccggttgt tgatattgtt tgctgttggg tttttgctgt
 901 tttttttttt tttttttttt ttaaaacaaa agagaggctc tatttttgta ttccacttgg
 961 ctgtggtgtc tgtcttctta actctcagaa agctccatta gtggcctaga ctgggattcc
1021 ggctgggggt ttgcgggggt ggggggcttt ctctagcctg tgctgctgag gccccagtac
1081 ctccagggcc agttggctgg gcagccaggg actccactgc acccccaggt ggggcaggga
1141 ggaaaggact gtgacatagg gcagtcctct tagaagtggg tatcagactg gtggctatta
1201 aatgattgaa atatttattt aacttgcata ttaaaaatgt gtgctggaga gtgagtcctg
1261 ccggggtcag cccctccctc caaccttgcc ccagctggtg ggcggctggg agacgcagat
1321 gaccaggtgc cagctctgac cacagcctcc ctccagccta aagacacctg cctgtcaacc
1381 atccccatca ctgtcacttg aggggttttc ctgcaaggac agaagcaggg aaaggggcaa
1441 gaagaggctc ttagctagtc cttggagctc tcagatgtgt acctcctagc actttacaga
1501 ggtcattgct aacacttccc caggccacct cagggccaga aataatggat gtgctagggc
1561 tagagctgta atcatggatt taatcctctt aaaaagtgct tctctgagtg cctaggtcca
1621 tgtgggagac aggttggaga ttccagaact tgctctttct gagactcagg ctccagaaaa
1681 tgaaagaaaa gagcagctgc cagggtccaa ggtgggggca tattggaggg ggaccaccaa
1741 gactggtgtt gacaatggtg atgtgggaca agtgttaacc ttgggtgata tggtgagata
1801 gctgtgggca gaaagcactg agctgaggtg cggcgaggag cctggggaac tgtcttccag
1861 gaagaggctg cccacctcgg aggatgggct ggcgggagag gagctgggca ccggatggca
1921 ccagaaggga agctcatagg cctagcgcag aactaaaggc agtcatagcc ttggggagaa
1981 gcaggaggcc gtatgtggag ggagggaggg ctgctgtggg agtggtggag caggtcatgg
2041 tgtgggcaga gaagggaatg ggcaagggtg caggtgtgtg tttgcgtgtg gactggtgag
2101 actggtgtcc tgccacaccg agggagagcc caggccccac ggcagtttcc tgagtgcaga
2161 gctggcccag gcttcatcgc tgaggcctcc cattagggct gctcctgctt ccttccttgt
2221 ggatgccctg ggctggtccc acagcccagc tactgagcca gtctaga
```

Sequence of NkX2.1 mRNA NCBI Reference Sequence: NM_001079668.2

(SEQ ID NO: 44)

```
   1 ctgacagaca cgtagaccaa cagtgcggcc ccagggttcg tccccagact cgctcgctca
  61 tttgttggcg actggggctc agcgcagcga agcccgatgt ggtccggagg cagtgggaag
 121 gcgcggggct gggaggccgc ggcgggaggg aggagcagcc ccggcaggct cagccgccgc
 181 cgaatcatgt cgatgagtcc aaagcacacg actccgttct cagtgtctga catcttgagt
 241 cccctggagg aaagctacaa gaaagtgggc atggagggcg gcggcctcgg ggctccgctg
 301 gcggcgtaca ggcagggcca ggcggcaccg ccaacagcgg ccatgcagca gcacgccgtg
 361 gggcaccacg gcgccgtcac cgccgcctac cacatgacgg cggcgggggt gccccagctc
 421 tcgcactccg ccgtgggggg ctactgcaac ggcaacctgg gcaacatgag cgagctgccg
 481 ccgtaccagg acaccatgag gaacagcgcc tctggccccg gatggtacgg cgccaaccca
 541 gacccgcgct tccccgccat ctcccgcttc atgggcccgg cgagcggcat gaacatgagc
 601 ggcatgggcg gcctgggctc gctgggggac gtgagcaaga acatggcccc gctgccaagc
 661 gcgccgcgca ggaagcgccg ggtgctcttc tcgcaggcgc aggtgtacga gctggagcga
 721 cgcttcaagc aacagaagta cctgtcggcg ccggagcgcg agcacctggc cagcatgatc
 781 cacctgacgc ccacgcaggt caagatctgg ttccagaacc accgctacaa aatgaagcgc
 841 caggccaagg acaaggcggc gcagcagcaa ctgcagcagg acagcggcgg cggcgggggc
 901 ggcgggggca ccgggtgccc gcagcagcaa caggctcagc agcagtcgcc gcgacgcgtg
 961 gcggtgccgg tcctggtgaa agacggcaaa ccgtgccagg cgggtgcccc cgcgccgggc
1021 gccgccagcc tacaaggcca cgcgcagcag caggcgcagc accaggcgca ggccgcgcag
1081 gcggcggcag cggccatctc cgtgggcagc ggtggcgccg gccttggcgc acacccgggc
1141 caccagccag gcagcgcagg ccagtctccg gacctggcgc accacgccgc cagcccccgcg
1201 gcgctgcagg gccaggtatc cagcctgtcc cacctgaact cctcgggctc ggactacggc
1261 accatgtcct gctccacctt gctatacggt cggacctggt gagaggacgc cgggccggcc
1321 ctagcccagc gctctgcctc accgcttccc tcctgcccgc cacacagacc accatccacc
1381 gctgctccac gcgcttcgac ttttcttaac aacctggccg cgtttagacc aaggaacaaa
1441 aaaaccacaa aggccaaact gctggacgtc tttctttttt tccccccccta aaatttgtgg
1501 gtttttttttt ttaaaaaaag aaaatgaaaa acaaccaagc gcatccaatc tcaaggaatc
1561 tttaagcaga gaagggcata aaacagcttt ggggtgtctt tttttggtga ttcaaatggg
1621 ttttccacgc tagggcgggg cacagattgg agagggctct gtgctgacat ggctctggac
1681 tctaaagacc aaacttcact ctgggcacac tctgccagca aagaggactc gcttgtaaat
```

-continued

| Sequences |
|---|
| 1741 accaggattt tttttttttt ttgaagggag gacgggagct ggggagagga aagagtcttc |
| 1801 aacataaccc acttgtcact gacacaaagg aagtgccccc tccccggcac cctctggccg |
| 1861 cctaggctca gcggcgaccg ccctccgcga aaatagtttg tttaatgtga acttgtagct |
| 1921 gtaaaacgct gtcaaaagtt ggactaaatg cctagttttt agtaatctgt acattttgtt |
| 1981 gtaaaaagaa aaaccactcc cagtccccag cccttcacat tttttatggg cattgacaaa |
| 2041 tctgtgtata ttatttggca gtttggtatt tgcggcgtca gtcttttttct gttgtaactt |
| 2101 atgtagatat ttggcttaaa tatagttcct aagaagcttc taataaatta tacaaattaa |
| 2161 aaagattctt tttctgatta aaaaaaaaaa aaaaaaa. |

REFERENCES

The references cited throughout the specification and Examples are incorporated herein in their entirety by reference.

The invention claimed is:

1. A method for the generation of a population of cells comprising Sox6 expressing medial ganglionic eminence (MGE) cells from pluripotent stem cells comprising the steps:

a) contacting a population of pluripotent stem cells with a Wnt inhibitor from day 0 to day 7 of neural induction;

b) contacting a population of pluripotent stem cells with a SMAD inhibitor from day 0 to day 14 of neural induction;

c) contacting the population of pluripotent stem cells with an activator of sonic hedgehog (SHH) from day 0 to day 21 of neural induction;

d) contacting the population of pluripotent stem cells with exogenous fibroblast growth factor 8 (FGF8) protein from day 8 to day 21 of neural induction; and e) determining one or more cells from the population of cells expresses Sox6, thereby generating a population of cells comprising Sox6 expressing MGE cells.

2. The method of claim 1, wherein the activator of sonic hedgehog comprises one or more of smoothened agonist (SAG), sonic hedgehog, pumorphamine, and Hh-Agl.5.

3. The method of claim 1, wherein the inhibitor of SMAD comprises one or more of LDN193189 and SB431542.

4. The method of claim 1, wherein the pluripotent stem cells are human cells.

5. The method of claim 1, wherein the pluripotent stem cells are embryonic stem cells.

6. The method of claim 1, wherein the pluripotent stem cells are induced pluripotent stem cells.

7. The method of claim 1, wherein the pluripotent stem cells are cultured as embryoid bodies.

8. The method of claim 1, wherein the pluripotent stem cells are cultured in suspension.

9. The method of claim 8, wherein the pluripotent stem cells are cultured in KSR media for at least a part of the method.

10. The method of claim 1, wherein the pluripotent stem cells are cultured as adherent cells.

11. The method of claim 1, wherein the WNT inhibitor comprises one or more of C I-7, IWP analogs, IWR analogs, XAV939, 53AH, Wnt-C59, IWP2, IWP4, ICG001, IWR-1-endo, Wnt-C59, LGK-974, FH535, WIK14, and IWP-L.

12. The method of claim 1, wherein step (a) comprises contacting the population of pluripotent stem cells with IWP2.

13. The method of claim 1, wherein the population of pluripotent stem cells of step (b) is contacted with a second SMAD inhibitor from day 0 to day 7 of neural induction.

14. The method of claim 1, wherein at least 75% of the cells from the population of cells express Sox6.

15. The method of claim 14, wherein the Sox6-expressing cells co-express FoxG1.

16. The method of claim 1, further comprising step (f) enriching FoxG1-expressing cells by selecting Sox6-expressing cells from the population of cells.

17. The method of claim 16, wherein the WNT inhibitor comprises one or more of C I-7, IWP analogs, IWR analogs, XAV939, 53AH, Wnt-C59, IWP2, IWP4, ICG001, IWR-1-endo, Wnt-C59, LGK-974, FH535, WIK14, and IWP-L.

18. The method of claim 16, wherein the inhibitor of SMAD comprises one or more of LDN193189 and SB431542.

19. The method of claim 16, wherein the activator of sonic hedgehog comprises one or more of smoothened agonist (SAG), sonic hedgehog, pumorphamine, and Hh-Agl.5.

* * * * *